United States Patent
Kim et al.

(10) Patent No.: US 9,750,615 B2
(45) Date of Patent: *Sep. 5, 2017

(54) PROSTHETIC INTERVERTEBRAL DISCS HAVING END PLATES AND FIBERS BETWEEN THOSE END PLATES

(75) Inventors: Daniel H. Kim, Mountain View, CA (US); Thomas A. Afzal, Menlo Park, CA (US); Michael L. Reo, Redwood City, CA (US); Uriel Hiram Chee, Santa Cruz, CA (US); In Haeng Cho, Seoul (KR); Kunwoo Lee, Seoul (KR); Curtis W. Frank, Cupertino, CA (US); Sung Kyu Ha, Kyunggi-do (KR)

(73) Assignee: SPINAL KINETICS, INC., Sunnyvale, CA (US)

( * ) Notice: Subject to any disclaimer, the term of this patent is extended or adjusted under 35 U.S.C. 154(b) by 668 days.

This patent is subject to a terminal disclaimer.

(21) Appl. No.: 11/968,183

(22) Filed: Jan. 1, 2008

(65) Prior Publication Data
US 2008/0103599 A1 May 1, 2008

Related U.S. Application Data

(63) Continuation of application No. 10/903,276, filed on Jul. 30, 2004, now Pat. No. 7,905,921, which is a (Continued)

(51) Int. Cl.
*A61F 2/44* (2006.01)
*A61F 2/46* (2006.01)
(Continued)

(52) U.S. Cl.
CPC ............ *A61F 2/4425* (2013.01); *A61F 2/442* (2013.01); *A61F 2/4611* (2013.01); *A61B 17/86* (2013.01);
(Continued)

(58) Field of Classification Search
CPC .................................................. A61F 2002/443
(Continued)

(56) References Cited

U.S. PATENT DOCUMENTS 3,867,728 A 2/1975 Stubstad
4,309,777 A 1/1982 Patil
(Continued)

FOREIGN PATENT DOCUMENTS

FR 2842724 A1 * 1/2004 ............. A61B 17/70

OTHER PUBLICATIONS

Hudgins, Robert, "*Development and Characterization of a Prosthetic Intevertebral Disc*," Thesis presented to the Academic Faculty, Georgia Institute of Technology (Nov. 1998).
(Continued)

*Primary Examiner* — Jan Christopher Merene
(74) *Attorney, Agent, or Firm* — E. Thomas Wheatloch

(57) ABSTRACT

Prosthetic intervertebral discs and methods for using the same are described. The subject prosthetic discs include upper and lower endplates separated by a compressible core member. The prosthetic discs described herein include one-piece, two-piece, three-piece, and four-piece structures. The subject prosthetic discs exhibit stiffness in the vertical direction, torsional stiffness, bending stiffness in the sagittal plane, and bending stiffness in the front plane, where the degree of these features can be controlled independently by adjusting the components of the discs. The interface mechanism between the endplates and the core members of several embodiments of the described prosthetic discs enables a very easy surgical operation for implantation.

29 Claims, 41 Drawing Sheets

Related U.S. Application Data continuation-in-part of application No. 10/632,538, filed on Aug. 1, 2003, now Pat. No. 7,153,325.

(51) Int. Cl.
  *A61B 17/86* (2006.01)
  *A61F 2/30* (2006.01)

(52) U.S. Cl.
  CPC ....... *A61F 2/30742* (2013.01); *A61F 2/30767* (2013.01); *A61F 2/30965* (2013.01); *A61F 2002/305* (2013.01); *A61F 2002/3052* (2013.01); *A61F 2002/30133* (2013.01); *A61F 2002/30383* (2013.01); *A61F 2002/30462* (2013.01); *A61F 2002/30523* (2013.01); *A61F 2002/30563* (2013.01); *A61F 2002/30566* (2013.01); *A61F 2002/30578* (2013.01); *A61F 2002/30596* (2013.01); *A61F 2002/30604* (2013.01); *A61F 2002/30733* (2013.01); *A61F 2002/30841* (2013.01); *A61F 2002/30884* (2013.01); *A61F 2002/30904* (2013.01); *A61F 2002/448* (2013.01); *A61F 2002/4495* (2013.01); *A61F 2002/4622* (2013.01); *A61F 2002/4627* (2013.01); *A61F 2002/4628* (2013.01); *A61F 2220/0025* (2013.01); *A61F 2220/0075* (2013.01); *A61F 2230/0015* (2013.01); *A61F 2310/00017* (2013.01); *A61F 2310/00023* (2013.01); *A61F 2310/00029* (2013.01); *A61F 2310/00161* (2013.01); *A61F 2310/00179* (2013.01); *A61L 2430/38* (2013.01)

(58) Field of Classification Search
  USPC ............ 623/17.11–17.16; 606/246, 249, 279
  See application file for complete search history.

(56) References Cited

U.S. PATENT DOCUMENTS

| | | | |
|---|---|---|---|
| 4,623,574 A | 11/1986 | Harpell et al. | |
| 4,759,769 A | 7/1988 | Hedman et al. | |
| 4,911,718 A | 3/1990 | Lee et al. | |
| 4,932,969 A | 6/1990 | Frey et al. | |
| 5,002,576 A | 3/1991 | Fuhrmann et al. | |
| 5,039,519 A | 8/1991 | Inoue et al. | |
| 5,071,437 A | 12/1991 | Steffee | |
| 5,171,281 A | 12/1992 | Parsons et al. | |
| 5,221,431 A | 6/1993 | Choe et al. | |
| 5,221,432 A | 6/1993 | Choe et al. | |
| 5,314,477 A | 5/1994 | Marnay | |
| 5,370,697 A | 12/1994 | Baumgartner | |
| 5,456,722 A | 10/1995 | McLeod et al. | |
| 5,458,642 A | 10/1995 | Beer et al. | |
| 5,545,229 A | 8/1996 | Parsons et al. | |
| 5,609,634 A | 3/1997 | Voydeville | |
| 5,827,328 A | 10/1998 | Buttermann | |
| 6,063,121 A | 5/2000 | Xavier et al. | |
| 6,113,638 A | 9/2000 | Williams et al. | |
| 6,156,067 A | 12/2000 | Bryan et al. | |
| 6,258,125 B1 | 7/2001 | Paul et al. | |
| 6,264,695 B1 | 7/2001 | Stoy | |
| 6,402,785 B1 | 6/2002 | Zdeblick et al. | |
| 6,419,704 B1 | 7/2002 | Ferree | |
| 6,419,706 B1 | 7/2002 | Graf | |
| 6,436,137 B2 | 8/2002 | Wang et al. | |
| 6,447,543 B1 | 9/2002 | Studer et al. | |
| 6,527,803 B1 | 3/2003 | Crozet et al. | |
| 6,527,804 B1 | 3/2003 | Gauchet et al. | |
| 6,533,818 B1 | 3/2003 | Weber et al. | |
| 6,582,466 B1 | 6/2003 | Gauchet | |
| 6,582,468 B1 | 6/2003 | Gauchet | |
| 6,626,943 B2 | 9/2003 | Eberlin et al. | |
| 6,626,944 B1 | 9/2003 | Taylor | |
| 6,645,248 B2 | 11/2003 | Casutt | |
| 6,656,224 B2 | 12/2003 | Middleton | |
| 6,682,562 B2 | 1/2004 | Viart et al. | |
| 6,692,495 B1 | 2/2004 | Zacouto | |
| 6,726,721 B2 | 4/2004 | Stoy et al. | |
| 6,733,532 B1 | 5/2004 | Gauchet et al. | |
| 6,733,533 B1 | 5/2004 | Lozier | |
| 6,733,535 B2 | 5/2004 | Michelson | |
| 6,746,485 B1 | 6/2004 | Zucherman et al. | |
| 6,749,635 B1 | 6/2004 | Bryan | |
| 6,827,740 B1 | 12/2004 | Michelson | |
| 6,827,743 B2 | 12/2004 | Eisermann et al. | |
| 7,025,787 B2 | 4/2006 | Bryan et al. | |
| 7,060,097 B2 | 6/2006 | Fraser et al. | |
| 7,074,240 B2 | 7/2006 | Pisharodi | |
| 7,147,665 B1 | 12/2006 | Bryan | |
| 7,153,325 B2 * | 12/2006 | Kim et al. | ................ 623/17.15 |
| 7,156,848 B2 * | 1/2007 | Ferree | ............ 606/261 |
| 7,166,130 B2 | 1/2007 | Ferree et al. | |
| 7,220,282 B2 | 5/2007 | Kuslich | |
| 7,229,441 B2 | 6/2007 | Trieu et al. | |
| 7,291,150 B2 | 11/2007 | Graf | |
| 7,309,357 B2 | 12/2007 | Kim et al. | |
| 7,563,284 B2 | 7/2009 | Coppes et al. | |
| 7,905,921 B2 * | 3/2011 | Kim et al. | ................ 623/17.16 |
| 2002/0026244 A1 | 2/2002 | Trieu | |
| 2002/0111687 A1 | 8/2002 | Ralph et al. | |
| 2002/0128714 A1 | 9/2002 | Manasas et al. | |
| 2003/0028251 A1 | 2/2003 | Mathews | |
| 2003/0045940 A1 * | 3/2003 | Eberlein et al. | ............ 623/17.16 |
| 2003/0204271 A1 * | 10/2003 | Ferree | ............ 623/61 |
| 2004/0006343 A1 | 1/2004 | Sevrain | |
| 2004/0143332 A1 | 7/2004 | Krueger et al. | |
| 2005/0021146 A1 | 1/2005 | de Villiers et al. | |
| 2005/0060036 A1 | 3/2005 | Schultz et al. | |
| 2005/0149120 A1 * | 7/2005 | Collier et al. | ................ 606/232 |
| 2005/0228375 A1 * | 10/2005 | Mazda et al. | ................ 606/61 |
| 2006/0129239 A1 | 6/2006 | Kwak | |
| 2007/0032875 A1 | 2/2007 | Blacklock et al. | |
| 2007/0168033 A1 | 7/2007 | Kim et al. | |

OTHER PUBLICATIONS

Takahata et al. "Bone Ingrowth Fixation of Artificial Intervertebral Disc Consisting of Bioceramic-coated Three-dimensional Fabric," Spine, vol. 28, No. 7, pp. 637-644.
U.S. Appl. No. 60/403,356, filed Aug. 15, 2002.
U.S. Appl. No. 60/403,402, filed Aug. 15, 2002.
Spinal Kinetics, Inc.'s Preliminary Invalidity Contentions (USDC, Case No. 5:09-cv-01201, *Synthes USA et al.* v. *Spinal Kinetics, Inc.*, Sep. 8, 2009).
Spinal Kinetics, Inc.'s Preliminary Invalidity Contentions—Exhibit 1 (chart comparing claims of U.S. Pat. No. 7,429,270 to Stubstad U.S. Pat. No. 3,867,728).
Spinal Kinetics, Inc.'s Preliminary Invalidity Contentions—Exhibit 2 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).
Spinal Kinetics, Inc.'s Preliminary Invalidity Contentions—Exhibit 3 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).
Spinal Kinetics, Inc.'s Preliminary Invalidity Contentions—Exhibit 4 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).
Spinal Kinetics, Inc.'s Preliminary Invalidity Contentions—Exhibit 5 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions—Exhibit 6 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).

(56) References Cited

OTHER PUBLICATIONS

Spinal Kinetics, Inc.'s Preliminary Invalidity Contentions—Exhibit 7 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).
Spinal Kinetics, Inc.'s Preliminary Invalidity Contentions—Exhibit 8 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Robert Hudgins, Georgia Inst. of Tech., Nov. 1998).
Spinal Kinetics, Inc.'s Preliminary Invalidity Contentions—Exhibit 9 (chart comparing claims of U.S. Pat. No. 7,429,270 to Stubstad U.S. Pat. No. 3,867,728 in view of Baumgartner U.S. Pat. No. 5,370,697).
Spinal Kinetics, Inc.'s Preliminary Invalidity Contentions—Exhibit 10 (chart comparing claims of U.S. Pat. No. 7,429,270 to Baumgartner U.S. Pat. No. 5,370,697 in view of Stubstad U.S. Pat. No. 3,867,728 and Steffe U.S. Pat. No. 4,071,437).
Spinal Kinetics, Inc.'s Preliminary Invalidity Contentions—Exhibit 11 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions—Exhibit 12 (chart comparing claims of U.S. Pat. No. 7,429,270 to Stubstad U.S. Pat. No. 3,867,728 in view of Development and Characterization of a Prosthetic Intervertebral Disc, Robert Hudgins, Georgia Inst. of Tech., Nov. 1998).
Spinal Kinetics, Inc.'s Preliminary Invalidity Contentions [Amended] (USDC, Case No. 5:09-cv-01201, *Synthes USA et al.* v. *Spinal Kinetics, Inc.*, Dec. 28, 2009).
Spinal Kinetics, Inc.'s Preliminary Invalidity Contentions [Amended]—Exhibit 1 (chart comparing claims of U.S. Pat. No. 7,429,270 to Stubstad U.S. Pat. No. 3,867,728).
Spinal Kinetics, Inc.'s Preliminary Invalidity Contentions [Amended]—Exhibit 2 (chart comparing claims of U.S. Pat. No. 7,429,270 to Coppes U.S. Pat. No. 7,563,284).
Spinal Kinetics, Inc.'s Preliminary Invalidity Contentions [Amended]—Exhibit 3 (chart comparing claims of U.S. Pat. No. 7,429,270 to Coppes U.S. Pat. No. 7,563,284 in combination with Stubstad U.S. Pat. No. 3,867,728).
Spinal Kinetics, Inc.'s Preliminary Invalidity Contentions [Amended]—Exhibit 4 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 5,071,437).
Spinal Kinetics, Inc.'s Preliminary Invalidity Contentions [Amended]—Exhibit 5 (chart comparing claims of U.S. Pat. No. 7,429,270 to Baumgartner U.S. Pat. No. 5,370,697 in view of Stubstad U.S. Pat. No. 3,867,728 and Parsons U.S. Pat. No. 5,171,281).
Spinal Kinetics, Inc.'s Preliminary Invalidity Contentions [Amended]—Exhibit 6 (chart comparing claims of U.S. Pat. No. 7,429,270 to Baumgartner U.S. Pat. No. 5,370,697 in view of Stubstad U.S. Pat. No. 3,867,728 and Eberlein U.S. Pat. No. 6,626,943).
Spinal Kinetics, Inc.'s Preliminary Invalidity Contentions [Amended]—Exhibit 7 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions [Amended]—Exhibit 8 (chart comparing claims of U.S. Pat. No. 7,429,270 to Baumgartner U.S. Pat. No. 5,370,697 in view of Stubstad U.S. Pat. No. 3,867,728 and Frey U.S. Pat. No. 4,932,969).
Spinal Kinetics, Inc.'s Preliminary Invalidity Contentions [Amended]—Exhibit 9 (chart comparing claims of U.S. Pat. No. 7,429,270 to Baumgartner U.S. Pat. No. 5,370,697 in view of Stubstad U.S. Pat. No. 3,867,728 and Gauchet U.S. Pat. No. 6,733,532).
Spinal Kinetics, Inc.'s Preliminary Invalidity Contentions [Amended]—Exhibit 10 (chart comparing claims of U.S. Pat. No. 7,429,270 to Baumgartner U.S. Pat. No. 5,370,697 in view of Stubstad U.S. Pat. No. 3,867,728 and Development and Characterization of a Prosthetic Intervertebral Disc, Hudgins, Georgia Inst. of Tech., Nov. 1998).
Spinal Kinetics, Inc.'s Preliminary Invalidity Contentions [Amended]—Exhibit 11 (chart comparing claims of U.S. Pat. No. 7,429,270 to Stubstad U.S. Pat. No. 3,867,728 in view of Baumgartner U.S. Pat. No. 5,370,697).
Spinal Kinetics, Inc.'s Preliminary Invalidity Contentions [Amended]—Exhibit 12 (chart comparing claims of U.S. Pat. No. 7,429,270 to Baumgartner U.S. Pat. No. 5,370,697 in view of Stubstad U.S. Pat. No. 3,867,728 and Steffee U.S. Pat. No. 4,071,437).
Spinal Kinetics, Inc.'s Preliminary Invalidity Contentions [Amended]—Exhibit 13 (chart comparing claims of U.S. Pat. No. 7,429,270 to Baumgartner U.S. Pat. No. 5,370,697 in view of Stubstad U.S. Pat. No. 3,867,728 and Casutt U.S. Pat. No. 6,645,248).
Spinal Kinetics, Inc.'s Preliminary Invalidity Contentions [Amended]—Exhibit 14 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions (USDC, Case No. 5:09-cv-01201, *Synthes USA et al.* v. *Spinal Kinetics, Inc.*, Sep. 30, 2010).
Spinal Kinetics, Inc.'s Second Amended Preliminary Invalidity Contentions—Exhibit 1 (chart comparing claims of U.S. Pat. No. 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 2 (chart comparing claims of U.S. Pat. No. 7,429,270 to Neuentwicklung eines lumbalen bewegungserhaltenden Bandscheibenimplantates, Feb. 25, 2002).
Spinal Kinetics, Inc.'s Second Amended Preliminary Invalidity Contentions—Exhibit 3 (chart comparing claims of U.S. Pat. No. 7,429,270 to Stubstad U.S. Pat. No. 3,867,728).
Spinal Kinetics, Inc.'s Second Amended Preliminary Invalidity Contentions—Exhibit 4 (chart comparing claims of U.S. Pat. No. 7,429,270 to Baumgartner PCT/CH2003/00247).
Spinal Kinetics, Inc.'s Second Amended Preliminary Invalidity Contentions—Exhibit 5 (chart comparing claims of U.S. Pat. No. 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 6 (chart comparing claims of U.S. Pat. No. 7,429,270 to Neuentwicklung eines Implantates für den totalen Bandschiebenersatz, Vorgelegt von: Adrian Burri und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 7 (chart comparing claims of U.S. Pat. No. 7,429,270 to Stubstad U.S. Pat. No. 3,867,728 in view of Eberlein U.S. Pat. No. 6,626,943).
Spinal Kinetics, Inc.'s Second Amended Preliminary Invalidity Contentions—Exhibit 8 (chart comparing claims of U.S. Pat. No. 7,429,270 to Stubstad U.S. Pat. No. 3,867,728 in view of Kim U.S. Pat. No. 7,153,325).
Spinal Kinetics, Inc.'s Second Amended Preliminary Invalidity Contentions—Exhibit 9 (chart comparing claims of U.S. Pat. No. 7,429,270 to Stubstad U.S. Pat. No. 3,867,728 in view of Optimal Design of Synthetic Intervertebral Disc Prosthesis Considering Nonlinear Mechanical Behavior, Kweon et al., Dec. 20, 2001).

(56) References Cited

OTHER PUBLICATIONS

Spinal Kinetics, Inc.'s Second Amended Preliminary Invalidity Contentions—Exhibit 10 (chart comparing claims of U.S. Pat. No. 7,429,270 to Stubstad U.S. Pat. No. 3,867,728 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 11 (chart comparing claims of U.S. Pat. No. 7,429,270 to Coppes U.S. Pat. No. 7,563,284 to Stubstad U.S. Pat. No. 3,867,728).

Spinal Kinetics, Inc.'s Second Amended Preliminary Invalidity Contentions—Exhibit 12 (chart comparing claims of U.S. Pat. No. 7,429,270 to Coppes U.S. Pat. No. 7,563,284 in view of Eberlein U.S. Pat. No. 6,626,943).

Spinal Kinetics, Inc.'s Second Amended Preliminary Invalidity Contentions—Exhibit 13 (chart comparing claims of U.S. Pat. No. 7,429,270 to Coppes U.S. Pat. No. 7,563,284 in view of Kim U.S. Pat. No. 7,153,325).

Spinal Kinetics, Inc.'s Second Amended Preliminary Invalidity Contentions—Exhibit 14 (chart comparing claims of U.S. Pat. No. 7,429,270 to Coppes U.S. Pat. No. 7,563,284 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 15 (chart comparing claims of U.S. Pat. No. 7,429,270 to Coppes U.S. Pat. No. 7,563,284 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 16 (chart comparing claims of U.S. Pat. No. 7,429,270 to Baumgartner U.S. Pat. No. 5,370,697 in view of Stubstad U.S. Pat. No. 3,867,728).

Spinal Kinetics, Inc.'s Second Amended Preliminary Invalidity Contentions—Exhibit 17 (chart comparing claims of U.S. Pat. No. 7,429,270 to Baumgartner U.S. Pat. No. 5,370,697 in view of Eberlein U.S. Pat. No. 6,626,943).

Spinal Kinetics, Inc.'s Second Amended Preliminary Invalidity Contentions—Exhibit 18 (chart comparing claims of U.S. Pat. No. 7,429,270 to Baumgartner U.S. Pat. No. 5,370,697 in view of Kim U.S. Pat. No. 7,153,325).

Spinal Kinetics, Inc.'s Second Amended Preliminary Invalidity Contentions—Exhibit 19 (chart comparing claims of U.S. Pat. No. 7,429,270 to Baumgartner U.S. Pat. No. 5,370,697 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 20 (chart comparing claims of U.S. Pat. No. 7,429,270 to Baumgartner U.S. Pat. No. 5,370,697 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 21 (chart comparing claims of U.S. Pat. No. 7,429,270 to Gauchet U.S. Pat. No. 6,733,532 in view of Stubstad U.S. Pat. No. 3,867,728).

Spinal Kinetics, Inc.'s Second Amended Preliminary Invalidity Contentions—Exhibit 22 (chart comparing claims of U.S. Pat. No. 7,429,270 to Gauchet U.S. Pat. No. 6,733,532 in view of Eberlein U.S. Pat. No. 6,626,943).

Spinal Kinetics, Inc.'s Second Amended Preliminary Invalidity Contentions—Exhibit 23 (chart comparing claims of U.S. Pat. No. 7,429,270 to Gauchet U.S. Pat. No. 6,733,532 in view of Kim U.S. Pat. No. 7,153,325).

Spinal Kinetics, Inc.'s Second Amended Preliminary Invalidity Contentions—Exhibit 24 (chart comparing claims of U.S. Pat. No. 7,429,270 to Gauchet U.S. Pat. No. 6,733,532 in view of Optimal Design of Synthetic Intervertebral Disc Prosthesis Considering Nonlinear Mechanical Behavior, Kweon et al., Dec. 20, 2001).

Spinal Kinetics, Inc.'s Second Amended Preliminary Invalidity Contentions—Exhibit 25 (chart comparing claims of U.S. Pat. No. 7,429,270 to Gauchet U.S. Pat. No. 6,733,532 in view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 26 (chart comparing claims of U.S. Pat. No. 7,429,270 to Baumgartner U.S. Pat. No. 5,370,697 in view of Stubstad U.S. Pat. No. 3,867,728).

Spinal Kinetics, Inc.'s Second Amended Preliminary Invalidity Contentions—Exhibit 27 (chart comparing claims of U.S. Pat. No. 7,429,270 to Coppes U.S. Pat. No. 7,563,284 in view of Stubstad U.S. Pat. No. 3,867,728).

Spinal Kinetics, Inc.'s Second Amended Preliminary Invalidity Contentions—Exhibit 28 (chart comparing claims of U.S. Pat. No. 7,429,270 to Baumgartner U.S. Pat. No. 5,370,697 in view of Stubstad U.S. Pat. No. 3,867,728 in further view of Development and Characterization of a Prosthetic Intervertebral Disc, Hudgins, Georgia Inst. of Tech., Nov. 1998).

Spinal Kinetics, Inc.'s Second Amended Preliminary Invalidity Contentions—Exhibit 29 (chart comparing claims of U.S. Pat. No. 7,429,270 to Coppes U.S. Pat. No. 7,563,284 in view of Stubstad U.S. Pat. No. 3,867,728 further in view of Development and Characterization of a Prosthetic Intervertebral Disc, Hudgins, Georgia Inst. of Tech., Nov. 1998).

Burri et al., Neuentwicklung eines Implantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002).

English Translation of Burri et al., Neuentwicklung eines Implantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002), entitled Mechanical Engineering and Process Engineering at the Swiss Fedearl Institute of Technology Zurich (ETH Zurich) Feb. 2002.

Burri et al., Neuentwicklung eines lumbalen bewegungserhaltenden Bandscheibenimplantates, Feb. 25, 2002.

English Translation of Burri et al., Neuentwicklung eines lumbalen bewegungserhaltenden Bandscheibenimplantates, Feb. 25, 2002.

Hudgins, Development and Characterization of a Prosthetic Intervertebral Disc, Hudgins, Georgia Inst. of Tech., Nov. 1998.

Kweon et al., Optimal Design of Synthetic Intervertebral Disc Prosthesis Considering Nonlinear Mechanical Behavior, Dec. 20, 2001.

\* cited by examiner

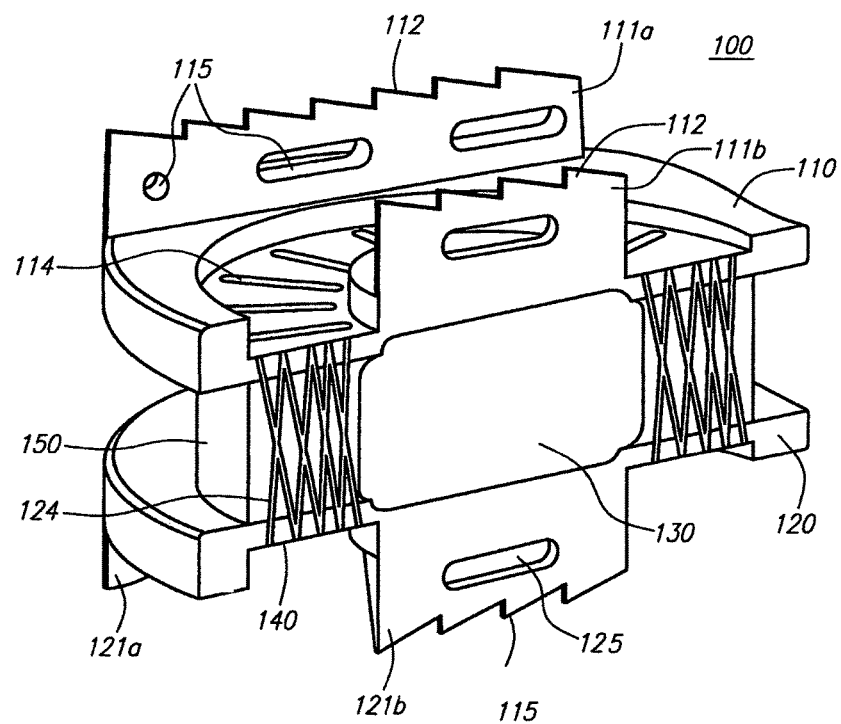
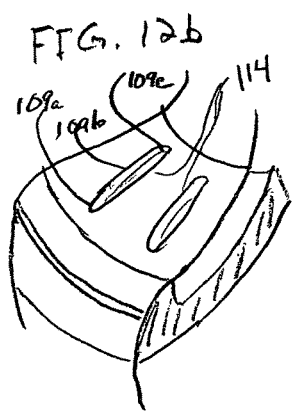
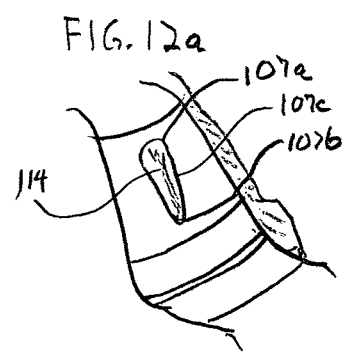
FIG. 12
FIG. 12b
FIG. 12a

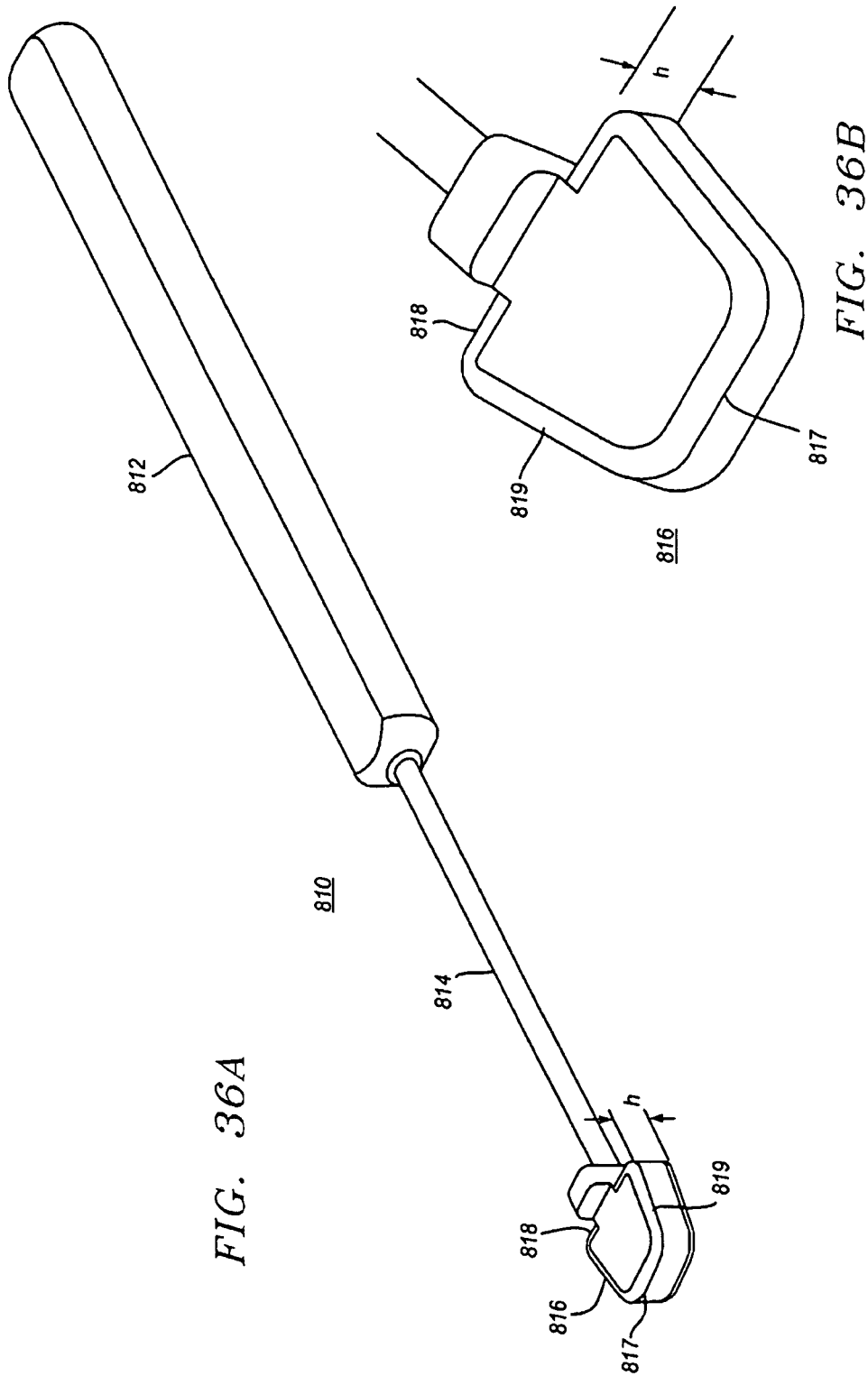

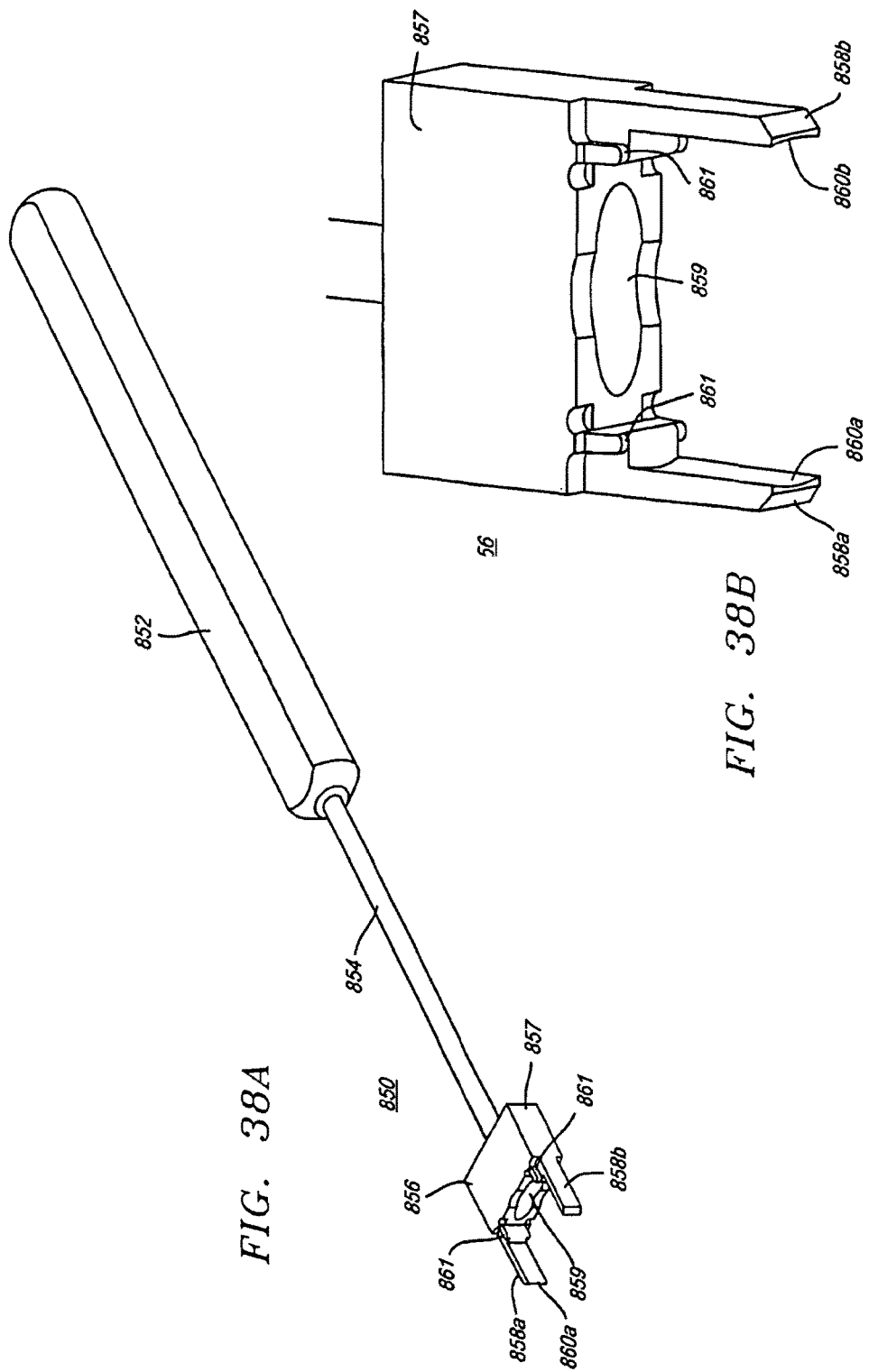

PROSTHETIC INTERVERTEBRAL DISCS HAVING END PLATES AND FIBERS BETWEEN THOSE END PLATES

RELATED APPLICATIONS

This application is a continuation of application Ser. No. 10/903,276, filed Jul. 30, 2004, now U.S. Pat. No. 7,905,921, which in turn, is a continuation-in-part of application Ser. No. 10/632,538, filed Aug. 1, 2003, now U.S. Pat. No. 7,153,325, which prior applications are incorporated by reference.

BACKGROUND OF THE INVENTION

The intervertebral disc is an anatomically and functionally complex joint. The intervertebral disc is composed of three component structures: (1) the nucleus pulposus; (2) the annulus fibrosus; and (3) the vertebral endplates. The biomedical composition and anatomical arrangements within these component structures are related to the biomechanical function of the disc.

The spinal disc may be displaced or damaged due to trauma or a disease process. If displacement or damage occurs, the nucleus pulposus may herniate and protrude into the vertebral canal or intervertebral foramen. Such deformation is known as herniated or slipped disc. A herniated or slipped disc may press upon the spinal nerve that exits the vertebral canal through the partially obstructed foramen, causing pain or paralysis in the area of its distribution.

To alleviate this condition, it may be necessary to remove the involved disc surgically and fuse the two adjacent vertebra. In this procedure, a spacer is inserted in the place originally occupied by the disc and it is secured between the neighboring vertebrae by the screws and plates/rods attached to the vertebra. Despite the excellent short-term results of such a "spinal fusion" for traumatic and degenerative spinal disorders, long-term studies have shown that alteration of the biomechanical environment leads to degenerative changes at adjacent mobile segments. The adjacent discs have increased motion and stress due to the increased stiffness of the fused segment. In the long term, this change in the mechanics of the motion of the spine causes these adjacent discs to degenerate.

To circumvent this problem, an artificial intervertebral disc replacement has been proposed as an alternative approach to spinal fusion. Although various types of artificial intervertebral discs have been developed to restore the normal kinematics and load-sharing properties of the natural intervertebral disc, they can be grouped into two categories, i.e., ball and socket joint type discs and elastic rubber type discs.

Artificial discs of ball and socket type are usually composed of metal plates, one to be attached to the upper vertebra and the other to be attached to the lower vertebra, and a polyethylene core working as a ball. The metal plates have concave areas to house the polyethylene core. The ball and socket type allows free rotation between the vertebrae between which the disc is installed and thus has no load sharing capability against the bending. Artificial discs of this type have a very high stiffness in the vertical direction, they cannot replicate the normal compressive stiffness of the natural disc. Also, the lack of load bearing capability in these types of discs causes adjacent discs to take up the extra loads resulting in the eventual degeneration of the adjacent discs.

In elastic rubber type artificial discs, an elastomeric polymer is embedded between metal plates and these metal plates are fixed to the upper and the lower vertebrae. The elastomeric polymer is bonded to the metal plates by having the interface surface of the metal plates be rough and porous. This type of disc can absorb a shock in the vertical direction and has a load bearing capability. However, this structure has a problem in the interface between the elastomeric polymer and the metal plates. Even though the interface surfaces of the metal plates are treated for better bonding, polymeric debris may nonetheless be generated after long term usage. Furthermore, the elastomer tends to rupture after a long usage because of its insufficient shear-fatigue strength.

Because of the above described disadvantages associated with either the ball/socket or elastic rubber type discs, there is a continued need for the development of new prosthetic devices.

RELEVANT LITERATURE

U.S. Pat. Nos. 3,867,728; 4,911,718; 5,039,549; 5,171,281; 5,221,431; 5,221,432; 5,370,697; 5,545,229; 5,674,296; 6,162,252; 6,264,695; 6,533,818; 6,582,466; 6,582,468; 6,626,943; 6,645,248. Also of interest are published U.S. Patent Application Nos. 2002/0107575, 2003/0040800, 2003/0045939, and 2003/0045940. See also Masahiko Takahata, et al. "Bone Ingrowth Fixation of Artificial Intervertebral Disc Consisting of Bioceramic-Coated Three-dimensional Fabric," SPINE, Vol. 28, No. 7, pp. 637-44 (2003).

SUMMARY OF THE INVENTION

Prosthetic intervertebral discs and methods for using such discs are provided. The subject prosthetic discs include an upper endplate, a lower endplate, and a compressible core member disposed between the two endplates.

In one embodiment, the subject prosthetic discs are characterized by including top and bottom endplates separated by a fibrous compressible element that includes an annular region and a nuclear region. The two plates are held together by at least one fiber wound around at least one region of the top endplate and at least one region of the bottom endplate. The subject discs may be employed with separate vertebral body fixation elements, or they may include integrated vertebral body fixation elements. Also provided are kits and systems that include the subject prosthetic discs.

In other embodiments, the prosthetic disc comprises an integrated, single-piece structure. In another embodiment, the prosthetic disc comprises a two-piece structure including a lower endplate and a separable upper endplate assembly that incorporates the core member. The two-piece structure may be a constrained structure, wherein the upper endplate assembly is attached to the lower endplate in a manner that prevents relative rotation, or a partially or semi-constrained structure or an unconstrained structure, wherein the upper endplate assembly is attached to the lower endplate in a manner that allows relative rotation. In yet another, embodiment, the prosthetic disc comprises a three-piece structure including upper and lower endplates and a separable core member that is captured between the upper and lower endplates by a retaining mechanism. Finally, in yet another embodiment, the prosthetic disc comprises a four-piece structure including upper and lower endplates and two separable core assemblies which, together, form a core member.

Several optional core materials and structures may be incorporated in each of the prosthetic disc embodiments described herein. For example, the core member may be formed of a relatively compliant material, such as polyurethane or silicone, and is typically fabricated by injection molding. In other examples, the core member may be formed by layers of fabric woven from fibers. In still further examples, the core member may comprise a combination of these materials, such as a fiber-reinforced polyurethane or silicone. As an additional option, one or more spring members may be placed between the upper and lower endplates in combination with the core member, such as in a coaxial relationship in which the core member has a generally cylindrical or toroidal shape and a spring is located at its center.

In the various embodiments, the disc structures are held together by at least one fiber wound around at least one region of the upper endplate and at least one region of the lower endplate. The fibers are generally high tenacity fibers with a high modulus of elasticity. The elastic properties of the fibers, as well as factors such as the number of fibers used, the thickness of the fibers, the number of layers of fiber windings, the tension applied to each layer, and the crossing pattern of the fiber windings enable the prosthetic disc structure to mimic the functional characteristics and biomechanics of a normal-functioning, natural disc.

Apparatus and methods for implanting prosthetic intervertebral discs are also provided. In a first embodiment, the apparatus includes three implantation tools used to prepare the two adjacent vertebral bodies for implantation and then to implant the prosthetic disc. A first tool, a spacer, is adapted to be inserted between and to separate the two adjacent vertebral bodies to create sufficient space for implanting the prosthetic disc. A second tool, a chisel, includes one or more wedge-shaped cutting blades located on its upper and/or lower surfaces that are adapted to create grooves in the inward facing surfaces of the two adjacent vertebral bodies. A third tool, a holder, includes an engagement mechanism adapted to hold the prosthetic disc in place while it is being implanted, and to release the disc once it has been implanted.

In another embodiment, the implantation apparatus includes a guide member that engages the lower endplate and that remains in place during a portion of the disc implantation process. A lower pusher member slidably engages the guide member and is used to advance the lower endplate into place between two adjacent vertebrae of a patient's spine. An upper pusher member is preferably coupled to the lower pusher member and is used to advance a first chisel into place opposed to the lower endplate between the two adjacent vertebrae. Once in place, an upward force is applied to the upper pusher member to cause the first chisel to engage the upper vertebral body and to create one or more grooves on its lower surface. A downward force is also applied to the lower pusher member to cause the lower endplate to engage the lower vertebral body and to become implanted. The upper pusher member and first chisel are then removed, as is the lower pusher member. Preferably, a second chisel is then advanced along the guide member and is used to provide additional preparation of the upper vertebral body. After the completion of the preparation by the first chisel and, preferably, the second chisel, the upper endplate and core members of the prosthetic disc are implanted using an upper endplate holder that is advanced along the guide member. After implantation, the upper endplate holder and guide member are removed.

Apparatus and methods for implanting prosthetic intervertebral discs using minimally invasive surgical procedures are also provided. In one embodiment, the apparatus includes a pair of cannulas that are inserted posteriorly, side-by-side, to gain access to the spinal column at the disc space. A pair of prosthetic discs are implanted by way of the cannulas to be located between two vertebral bodies in the spinal column. In another embodiment, a single, selectively expandable disc is employed. In an unexpanded state, the disc has a relatively small profile to facilitate delivery of it to the disc space. Once operatively positioned, it can then be selectively expanded to an appropriate size to adequately occupy the disc space. Implantation of the single disc involves use of a single cannula and an articulating chisel or a chisel otherwise configured to establish a curved or right angle disc delivery path so that the disc is substantially centrally positioned in the disc space. Preferably, the prosthetic discs have sizes and structures particularly adapted for implantation by the minimally invasive procedure.

Other and additional devices, apparatus, structures, and methods are described by reference to the drawings and detailed descriptions below.

BRIEF DESCRIPTION OF THE DRAWINGS

The Figures contained herein are not necessarily drawn to scale, with some components and features being exaggerated for clarity.

FIG. 3C illustrates the manner in which the 2D fabrics in FIG. 3B are stitched together.

FIG. 4A provides a three-dimensional top view of a prosthetic disc according to an embodiment of the present invention in which the fixation elements are integral to the disc, while

FIG. 12 provides a cross-sectional view of a prosthetic disc having a one-piece structure. FIGS. 12*a* and 12*b* show variations of slots in endplates.

FIG. 36A provides a perspective view of a spacer.

FIG. 36B provides a perspective view of the head portion of the spacer shown in FIG. 36A.

FIG. 38A provides a perspective view of a holder.

FIG. 38B provides a perspective view of the head portion of the holder shown in FIG. 38A.

DESCRIPTIONS OF THE PREFERRED EMBODIMENTS

Figure 1A:
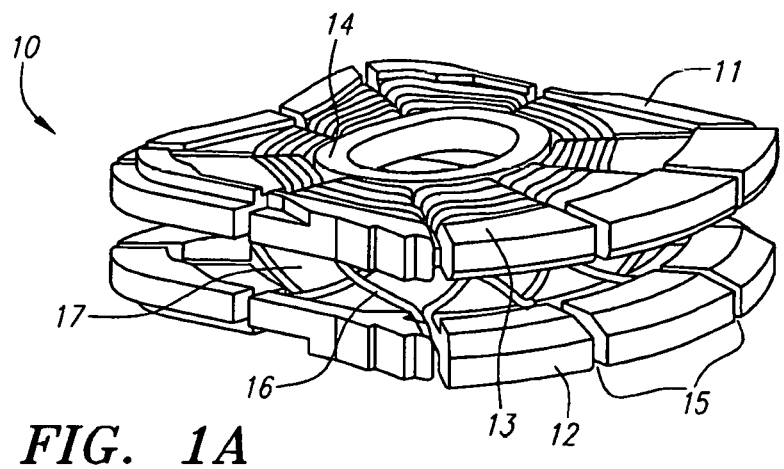
FIGS. 1A and 1B provide a three dimensional view of two different prosthetic discs according to the subject invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

Prosthetic intervertebral discs, methods of using such discs, apparatus for implanting such discs, and methods for implanting such discs are described herein. It is to be understood that the prosthetic intervertebral discs, implantation apparatus, and methods are not limited to the particular embodiments described, as these may, of course, vary. It is also to be understood that the terminology used herein is for the purpose of describing particular embodiments only, and is not intended to be limiting, since the scope of the present inventions will be limited only by the appended claims.

The following description includes three Parts. Part A contains a description of a first set of embodiments of the subject prosthetic intervertebral discs, a review of representative methods for using the prosthetic discs, and a review of systems and kits that include the subject prosthetic discs. The embodiments described in Part A are those illustrated in FIGS. 1-11. Part B contains a description of a second set of embodiments of the subject prosthetic intervertebral discs, methods for using the discs, and apparatus and methods for implanting the discs. The embodiments described in Part B are those illustrated in FIGS. 12-54. Each of the descriptions contained in Parts A and B will be understood to be complete and comprehensive in its own right, as well as describing structures, features, and methods that are suitable for use with those described in the other Part. Part C includes additional information about the descriptions contained herein.

Part A

I. Prosthetic Intervertebral Disc

As summarized above, the subject invention is directed to a prosthetic intervertebral disc. By prosthetic intervertebral disc is meant an artificial or manmade device that is configured or shaped so that it can be employed as a replacement for an intervertebral disc in the spine of a vertebrate organism, e.g., a mammal, such as a human. The subject prosthetic intervertebral disc has dimensions that permit it to substantially occupy the space between two adjacent vertebral bodies that is present when the naturally occurring disc between the two adjacent bodies is removed, i.e., a void disc space. By substantially occupy is meant that it occupies at least about 75% by volume, such as at least about 80% by volume or more. The subject discs may have a roughly bean shaped structure analogous to naturally occurring intervertebral body discs which they are designed to replace. In many embodiments the length of the disc ranges from about 15 mm to about 50 mm, such as from about 18 mm to about 46 mm, the width of the disc ranges from about 12 mm to about 30 mm, such as from about 14 mm to about 25 mm and the height of the disc ranges from about 3 mm to about 13 mm, such as from about 5 mm to about 12 mm.

The subject discs are characterized in that they include both an upper (or top) and lower (or bottom) endplate, where the upper and lower endplates are separated from each other by a fibrous compressible element, where the combination structure of the endplates and fibrous compressible element provides a prosthetic disc that functionally closely mimics real disc. A feature of the subject prosthetic discs is that the top and bottom endplates are held together by at least one fiber, e.g., of the fibrous compressible element, wound around at least one portion of each of the top and bottom endplates. As such, the two endplates (or planar substrates)

are held to each other by one or more fibers that are wrapped around at least one domain/portion/area of the upper endplate and lower endplate such that the plates are joined to each other.

Figure 1B:
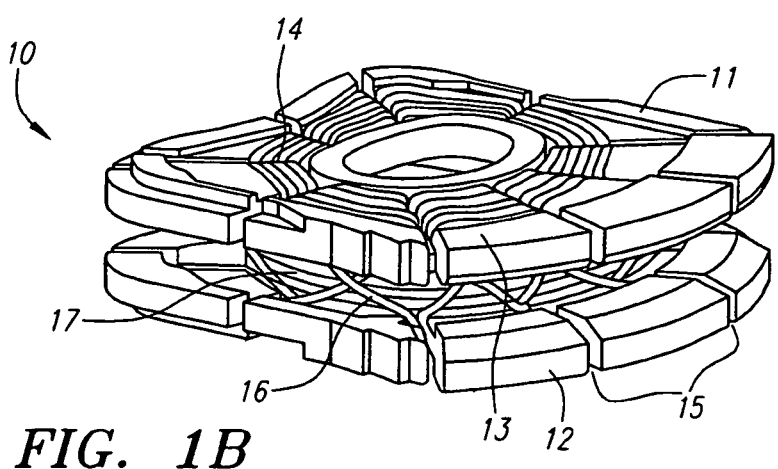

Two different representative intervertebral discs are shown in FIGS. 1A and 1B. As can be seen in FIGS. 1A and 1B, prosthetic discs 10 each include a top endplate 11 and a lower endplate 12. Top and bottom endplates 11 and 12 are planar substrates, where these plates typically have a length from about 12 mm to about 45 mm, such as from about 13 mm to about 44 mm, a width of from about 11 mm to about 28 mm, such as from about 12 mm to about 25 mm and a thickness of from about 0.5 mm to about 4 mm, such as from about 1 mm to about 3 mm. The top and bottom endplates are fabricated from a physiologically acceptable material that provides for the requisite mechanical properties, where representative materials from which the endplates may be fabricated are known to those of skill in the art and include, but are not limited to: titanium, titanium alloys, stainless steel, cobalt/chromium, etc.; plastics such as polyethylene with ultra high molar mass (molecular weight) (UHMW-PE), polyether ether ketone (PEEK), etc.; ceramics; graphite; etc. As shown in FIGS. 1A and 1B, separating the top and bottom endplates is a fibrous compressible element 17. The thickness of the fibrous compressible element may vary, but ranges in many embodiments from about 2 mm to about 10 mm, including from about 3 mm to about 8 mm.

The disc is further characterized in that it includes an annular region 13 (i.e., annulus), which is the region, domain or area that extends around the periphery of the disc, and a nuclear region (i.e., nucleus) 14, which is the region, domain or area in the center of the disc and surrounded by the annulus.

While in the broadest sense the plates may include a single region around which a fiber is wound in order to hold the plates together, in many embodiments the plates have a plurality of such regions. As shown in FIGS. 1A and 1B, endplates 11 and 12 include a plurality of slots 15 through which fibers, e.g., of the fibrous compressible element, may be passed through or wound, as shown. In many embodiments, the number of different slots present in the periphery of the device ranges from about 4 to about 36, such as from about 5 to about 25. As shown in FIGS. 1A and 1B, at least one fiber 16 of the fibrous compressible element is wrapped around a region of the top and bottom plates, e.g., by being passed through slots in the top and bottom plates, in order to hold the plates together.

The fibrous compressible elements, 17, are typically made up of one or more fibers, where the fibers are generally high tenacity fibers with a high modulus of elasticity. By high tenacity fibers is meant fibers that can withstand a longitudinal stress without tearing asunder of at least about 50 MPa, such as at least about 250 MPa. As the fibers have a high modulus of elasticity, their modulus of elasticity is typically at least about 100 MPa, usually at least about 500 MPa. The fibers are generally elongate fibers having a diameter that ranges from about 3 mm to about 8 mm, such as about 4 mm to about 7 mm, where the length of each individual fiber making up the fibrous component may range from about 1 m to about 20 m, such as from about 2 m to about 15 m.

The fibers making up the fibrous compressible elements may be fabricated from any suitable material, where representative materials of interest include, but are not limited to: polyester (e.g., Dacron), polyethylene, polyaramid, carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibrous compressible elements made up of one or more fibers wound around one or more regions of the top or bottom plates may make up a variety of different configurations. For example, the fibers may be wound in a pattern that has an oblique orientation to simulate the annulus of intact disc, where a representative oblique fiber configuration or orientation is shown in FIG. 1A. The number of layers of fiber winding may be varied to achieve similar mechanical properties to an intact disk. Where desired, compliancy of the structure may be reduced by including a horizontal winding configuration, as shown in FIG. 1B.

Figure 2:
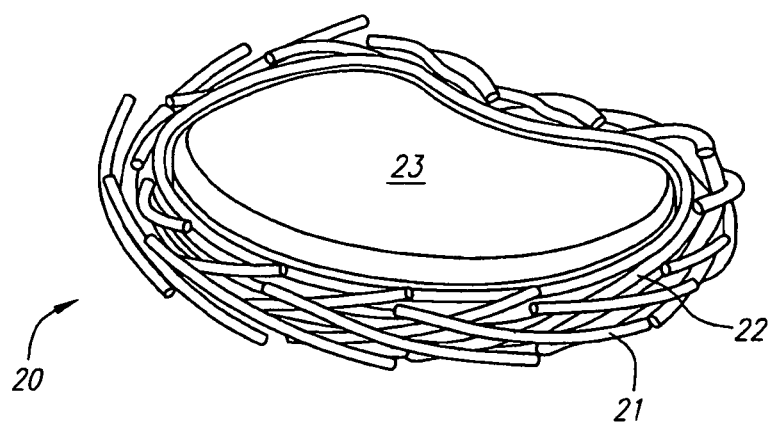
FIG. 2 provides a three-dimensional view of a fibrous compressible element that includes a polymeric nucleus and a fibrous annulus according to one embodiment of the subject invention.

In certain embodiments, the fibrous compressible element 20 has a fibrous component 21 limited to the annular region of the disc 22, e.g., to the region along the periphery of the disc. FIG. 2 provides a representation of this embodiment, where the fibrous component is limited solely to the annular region of the disc and includes both oblique and horizontal windings. Also shown is a separate polymeric component 23 present in the nucleus. The fiber windings of the various layers of fiber may be at varying angles from each other where the particular angle for each layer may be selected to provide a configuration that best mimics the natural disc. Additionally, the tension placed on the fibers of each layer may be the same or varied.

Figure 3A:
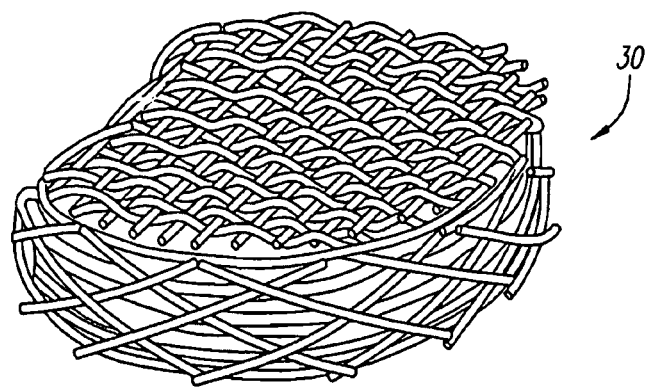
FIGS. 3A to 3C provide different views of a fibrous component of the fibrous compressible elements according to an embodiment of the subject invention.
Figure 3B:
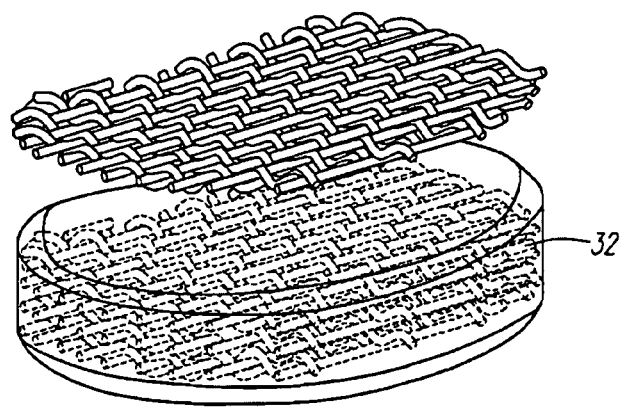
Figure 3C:
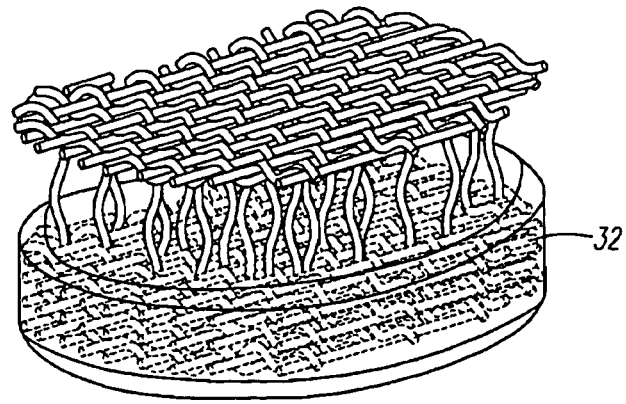

In yet other embodiments the fibrous component of the fibrous compressible element may extend beyond the annular region of the disc into at least about a portion, if not all, of the nucleus. FIG. 3A provides a view of a fibrous component 30 that occupies both the annular and nuclear regions of the disc, where the annular region of the disc is made up of fiber windings that are both oblique and horizontal, as described above, while the nucleus of the disc is occupied by fibers woven into a three-dimensional network that occupies the nuclear space. Instead of a three-dimensional network structure, one may have multiple two dimensional layers' of interwoven fibers stacked on top of each other, as shown in FIG. 3B, where the multiple stacked layers may be stitched to each other, as shown in FIG. 3C. By adjusting one or more parameters of the fibrous component, such as the density of the fibers, number of layers, frequency of stitching, the wrapping angle of each fiber layer, and the like, the mechanical properties of the fibrous component can be tailored as desired, e.g., to mimic the mechanical properties of a natural intervertebral disc. Also shown in FIGS. 3B and 3C is the outline of a polymeric component 32 in which the fibrous component 30 is embedded.

In certain embodiments, the fibrous compressible element further includes one or more polymeric components. The polymeric component(s), when present, may be fabricated from a variety of different physiologically acceptable materials. Representative materials of interest include, but are not limited to: elastomeric materials, such as polysiloxane, polyurethane, poly(ethylene propylene) copolymer, polyvinylchloride, poly(tetrafluoroethylene) and copolymers, hydrogels, and the like.

The polymeric component may be limited to particular domains, e.g., the annular and/or nucleus domains, or extend throughout the entire region of the fibrous compressible elements positioned between the two endplates. As such, in certain embodiments the polymeric component is one that is limited to the nuclear region of the disc, as shown in FIG. 2. In FIG. 2, fibrous compressible element 20 includes a distinct fibrous component 21 that is located in the annular region of the disc 22, while polymeric component 23 is located in the nuclear region of the disc. In other embodiments, the polymeric component is located in both the annular and nuclear regions. In yet other embodiments, the polymeric component may be located solely in the annular region.

Depending on the desired configuration and mechanical properties, the polymeric component may be integrated with the fibrous component, such that at least a portion of the fibers of the fibrous component is embedded in, e.g., complexed with, at least a portion of the polymeric component. In other words, at least a portion of the fibrous component is impregnated with at least a portion of the polymeric component. For example, as shown in FIG. 3B, stacked two-dimensional layers of the fibrous component 30 are present inside the polymeric component 32, such that the fibrous component is impregnated with the polymeric component.

In those configurations where the fibrous and polymeric components are present in a combined format, e.g., as shown in FIG. 3B, the fibers of the fibrous component may be treated to provide for improved bonding with the polymeric component. Representative fiber treatments of interest include, but are not limited to: corona discharge, $O_2$ plasma treatment, oxidation by strong acid ($HNO_3$, $H_2SO_4$). In addition, surface coupling agents may be employed, and/or a monomer mixture of the polymer may be polymerized in presence of the surface-modified fiber to produce the composite fiber/polymeric structure.

As indicated above, the devices may include one or more different polymeric components. In those embodiments where two or more different polymeric components are present, any two given polymeric components are considered different if they differ from each other in terms of at least one aspect, e.g., composition, cross-linking density, and the like. As such, the two or more different polymeric components may be fabricated from the same polymeric molecules, but differ from each other in terms of one or more of: cross-linking density; fillers; etc. For example, the same polymeric material may be present in both the annulus and nucleus of the disc, but the crosslink density of the annulus polymeric component may be higher than that of the nuclear region. In yet other embodiments, polymeric materials that differ from each other with respect to the polymeric molecules from which they are made may be employed.

By selecting particular fibrous component and polymeric component materials and configurations, e.g., from the different representative formats described above, a disc with desired functional characteristics, e.g., that mimics the functional characteristics of the naturally occurring disc, may be produced.

Representative particular combinations of interest include, but are not limited to, the following:
1. Biocompatible polyurethane, such as Ethicon Biomer, reinforced with Dacron poly(ethylene terephthalate) fiber, or Spectra polyethylene fiber, or Kevlar polyaramide fiber, or carbon fiber.
2. Biocompatible polysiloxane modified styrene-ethylene butylene block copolymer sold under C-Flex tradename reinforced with Dacron poly(ethylene terephthalate) fiber, or Spectra polyethylene fiber, or Kevlar polyaramide fiber, or carbon fiber.
3. Biocompatible Silastic silicone rubber, reinforced with Dacron poly(ethylene terephthalate) fiber, or Spectra polyethylene fiber, or Kevlar polyaramide fiber, or carbon fiber.

In using the subject discs, the prosthetic disc is fixed to the vertebral bodies between which it is placed. More specifically, the upper and lower plates of the subject discs are fixed to the vertebral body to which they are adjacent. As such, the subject discs are employed with vertebral body fixation elements during use. In certain embodiments, the vertebral body fixation elements are integral to the disc structure, while in other embodiments the vertebral body fixation elements are separate from the disc structure.

Figure 4A:
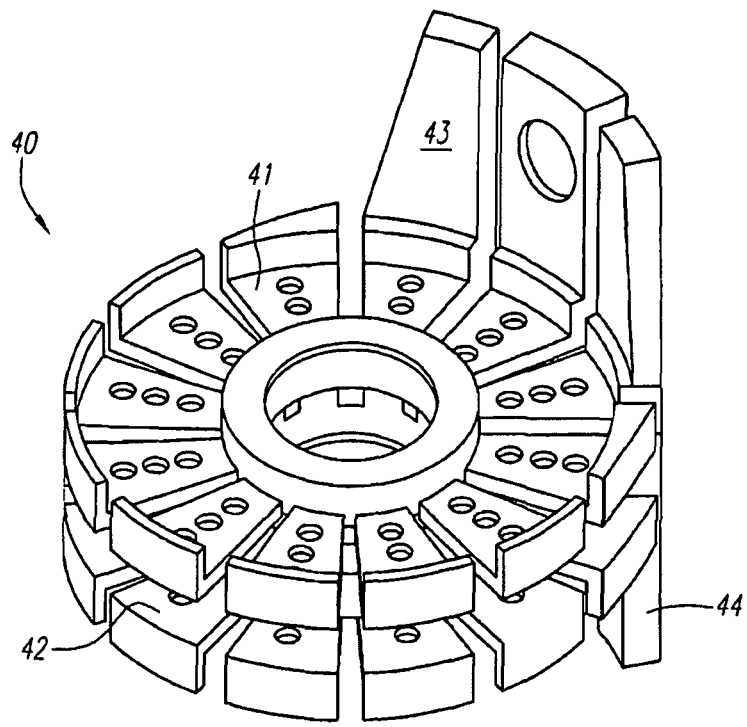
Figure 4B:
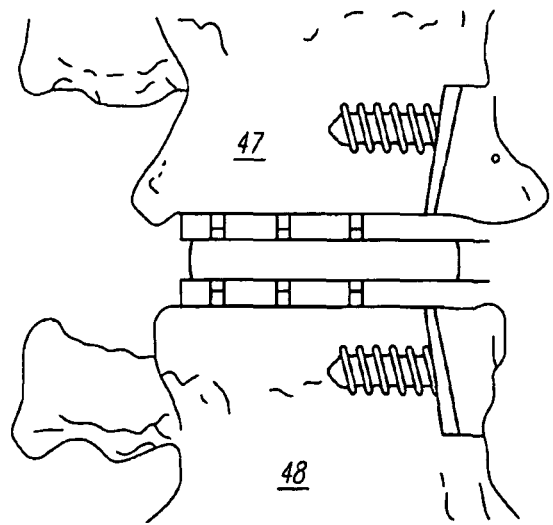
FIG. 4B shows the disc of FIG. 4A implanted with the use of bone screws.

A representative embodiment of those devices where the vertebral body fixation elements are integral with the disc structure is depicted in FIGS. 4A and 4B. FIG. 4A shows device 40 made up of top and bottom endplates 41 and 42. Integrated with top and bottom endplates 41 and 42 are vertebral body fixation elements 43 and 44. The vertebral body fixation elements include holes through which bone screws may be passed for fixation of the disc to upper and lower vertebral bodies 47 and 48 upon implantation, as represented in FIG. 4B.

Figure 7:
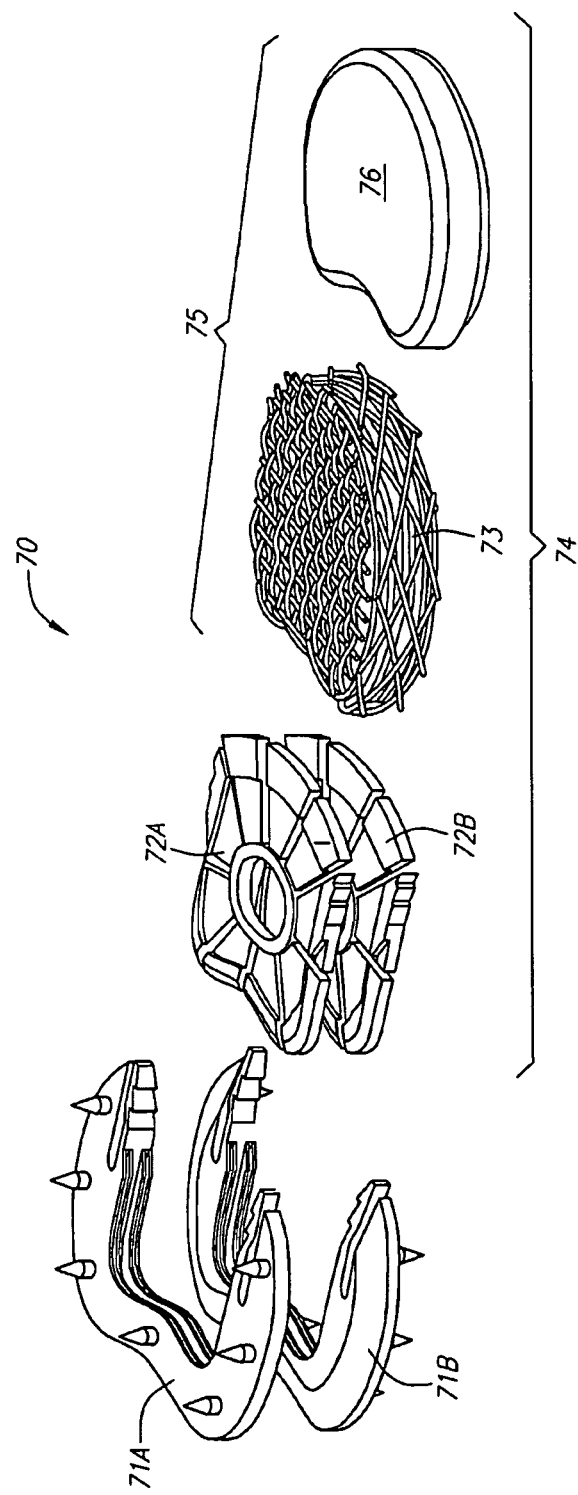
FIG. 7 provides an exploded view of a disc system that includes both an intervertebral disc and vertebral body fixation elements, according to an embodiment of the present invention.

In an alternative embodiment, the disc does not include integrated vertebral body fixation elements, but is designed to mate with separate vertebral body fixation elements, e.g., as depicted in FIG. 7. In other words, the disc is structured to interface with separate vertebral body fixation elements during use. Any convenient separate vertebral body fixation element may be employed in such embodiments, so long as it stably positions the prosthetic disc between two adjacent vertebral bodies.

Figure 5A:
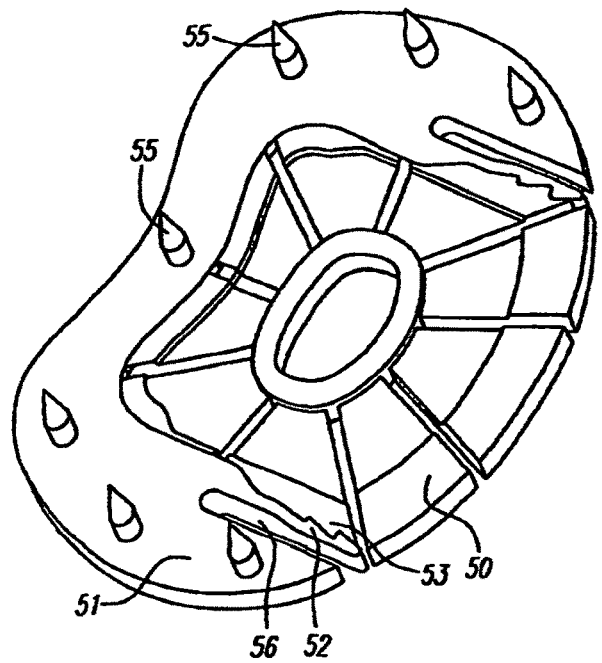
FIGS. 5A to 5C show the mating interface between disc top endplate with an upper vertebral body fixation element according to an embodiment of the subject invention.
Figure 5B:
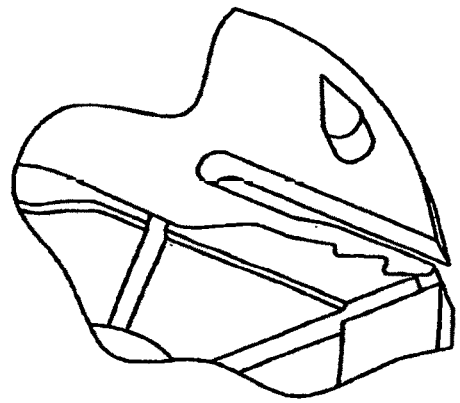
Figure 5C:
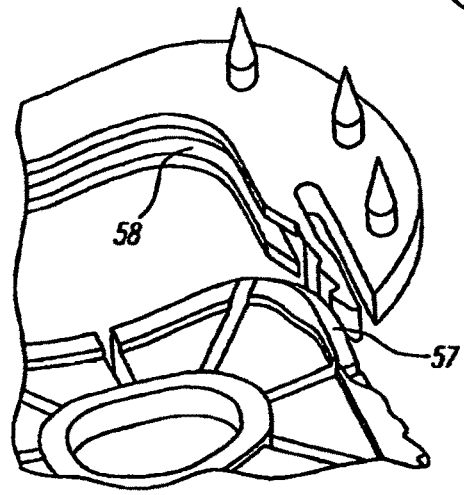

One representative non-integrated vertebral body fixation element according to this embodiment is shown in FIGS. 5A and 5B. FIG. 5A provides a representation of the upper plate 50 of a prosthetic disc mated with a vertebral body fixation element 51, as the structures would appear upon implantation. Vertebral body fixation element 51 is a horseshoe shaped structure having spikes 55 at locations corresponding to the cortical bone of vertebrae and porous coating to enhance bone fixation. The fixation element 51 also has gear teeth 52 such that corresponding gear teeth 53 of the disc upper plate 50 can slide through the gear contact resulting in the right location of prosthetic disc with respect to the fixation element. The gear teeth have a shape such that only inward movement of the upper plate upon implantation is possible. Also present are slots 56 in the spiked fixation elements next to the gear teeth that provide for the elastic deformation of the whole teeth area upon implantation and desirable clearance between mating gear teeth of the disc and fixation element so that incoming gear teeth of the disc can easily slide into the fixation element.

In the embodiment shown in FIG. 5A, as the disc is pushed into the fixation element, the protruded rail 57 on the disc slides along the corresponding concave rail-way 58 on the fixation element until the protruded rail on the most front side is pushed into the corresponding concave rail-way on the fixation element, as shown in FIG. 5B. This rail interface is devised to prevent the upward/downward movement of the top disc endplate and the bottom disc endplate with respect to the corresponding fixation element. This interface between the fixation elements and the top and bottom endplates of the disc enables an easy surgical operation. Specifically, the fixation elements are transferred together to the disc replacement area (disc void space) with an instrument and pushed in the opposite directions toward the vertebrae until they are fixed to the vertebrae, and then the prosthetic disc is transferred by the instrument between the fixation elements and simply pushed inward until the stoppers mate the corresponding stoppers. The prosthetic disc can also be easily removed after long-term use. For its removal, the gear teeth on the fixation element are pushed to reduce the gap of the slot so that the gear engagement between the disc endplate and the fixation element is released.

Figure 6A:
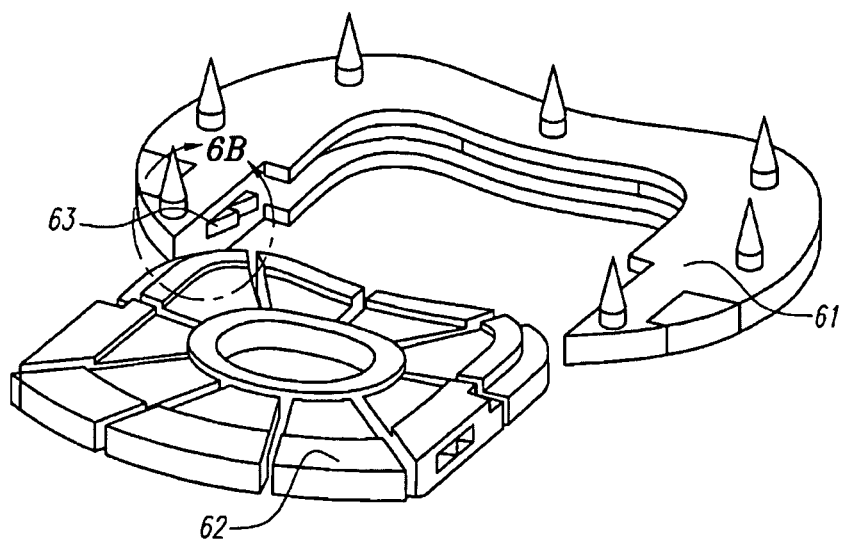
FIGS. 6A and 6B show the mating interface between disc top endplate with an upper vertebral body fixation element according to an alternative embodiment of the subject invention. The top endplate is clamped by a clamping element connected to the upper vertebral body fixation element through a spring.
Figure 6B:
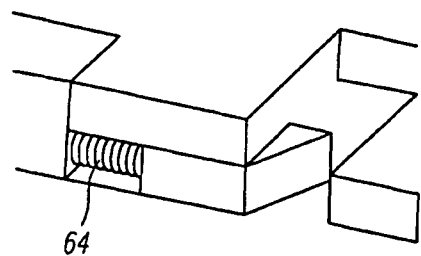

An alternative embodiment is depicted in FIGS. 6A and 6B. In the embodiment shown in FIGS. 6A and 6B, the fixation element 61 and the endplate 62 have a different mating interface from that depicted in FIGS. 5A and 5B. As shown in FIGS. 6A and 6B, the gear teeth in the endplate are brought in contact with the corresponding gear teeth of the clamping element 63 that is attached to the fixation element 61 through a spring 64. In this mechanism, the slots next to the gear teeth shown in the embodiment depicted in FIGS. 5A and 5B are replaced by a spring attached to the fixation element and this spring deformation provides the necessary recess of the clamping element as the disc endplate is pushed in upon implantation. The gear teeth contact between the endplate and the clamping element allows one way sliding. The disc endplates and the fixation elements have the rail interface as in FIGS. 5A and 5B to prevent the vertical movement.

II. Systems

Also provided are systems that include at least one component of the subject prosthetic discs, as described above. The systems of the subject invention typically include all of the elements that may be necessary and/or desired in order to replace an intervertebral disc with a prosthetic disc as described above. As such, at a minimum the subject systems include a prosthetic disc according to the present invention, as described above. In addition, the systems in certain embodiments include a vertebral body fixation element, or components thereof, e.g., the fixation elements shown in FIGS. 5A to 6B, bone screws for securing integrated fixation elements as shown in FIGS. 4A and 4B, and the like. The subject systems may also include special delivery devices, e.g., as described in greater detail below.

One specific representative system of particular interest is depicted in FIG. 7. The system 70 of FIG. 7 is depicted as an exploded view, and includes upper and lower fixation elements 71A and 71B, and disc 74 made up of top and bottom endplates 72A and 72B, as well as the fibrous compressible element 75, made up of both a fibrous component 73 and polymeric component 76 of the prosthetic disc.

III. Methods of Use

Also provided are methods of using the subject prosthetic intervertebral discs and systems thereof. The subject prosthetic intervertebral discs and systems thereof find use in the replacement of damaged or dysfunctional intervertebral discs in vertebrate organisms. Generally the vertebrate organisms are "mammals" or "mammalian," where these terms are used broadly to describe organisms which are within the class Mammalia, including the orders Carnivora (e.g., dogs and cats), Rodentia (e.g., mice, guinea pigs, and rats), Lagomorpha (e.g. rabbits) and Primates (e.g., humans, chimpanzees, and monkeys). In many embodiments, the subjects will be humans.

In general, the devices are employed by first removing the to be replaced disc from the subject or patient according to standard protocols to produce a disc void space. Next, the subject prosthetic disc is implanted or positioned in the disc void space, resulting in replacement of the removed disc with the prosthetic disc. This implantation step may include a vertebral body fixation element implantation substep, a post implantation vertebral body securing step, or other variations, depending on the particular configuration of the prosthetic device being employed. In addition, the implantation step described above may include use of one or more implantation devices (or disc delivery devices) for implanting the system components to the site of implantation.

A representative implantation protocol for implanting the device depicted in FIG. 7 is now provided. First, the spine of a subject is exposed via a retroperitoneal approach after sterile preparation. The intervertebral disc in trauma condition is removed, and the cartilage endplates above and below the disc are also removed to the bony end plates to obtain the bleeding surface for the bone growth into porous cavities in the spiked fixation elements 71A and 72A. The gap resulting from these removals is measured and the proper artificial disk assembly is chosen according to the measurement.

Figure 8:
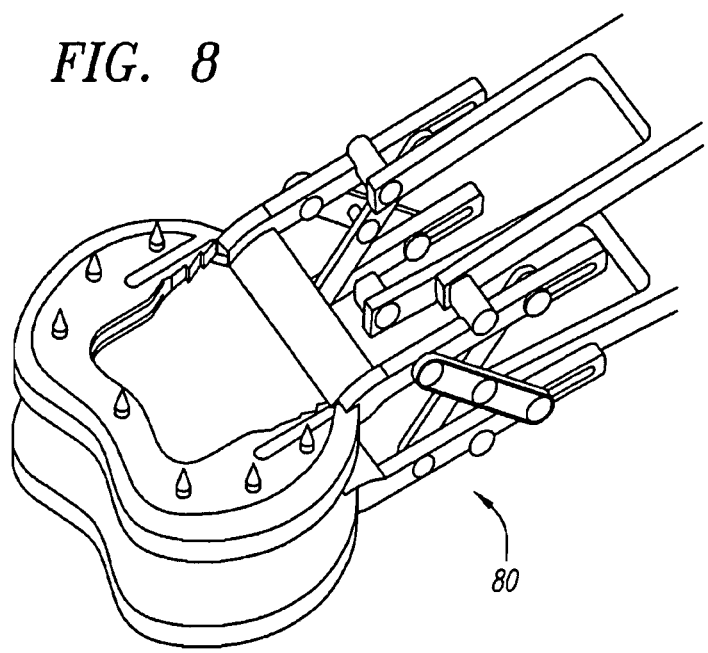
FIGS. 8 and 9 provide views of vertebral body fixation elements being held in an implantation device according to an embodiment of the subject invention.
Figure 9:
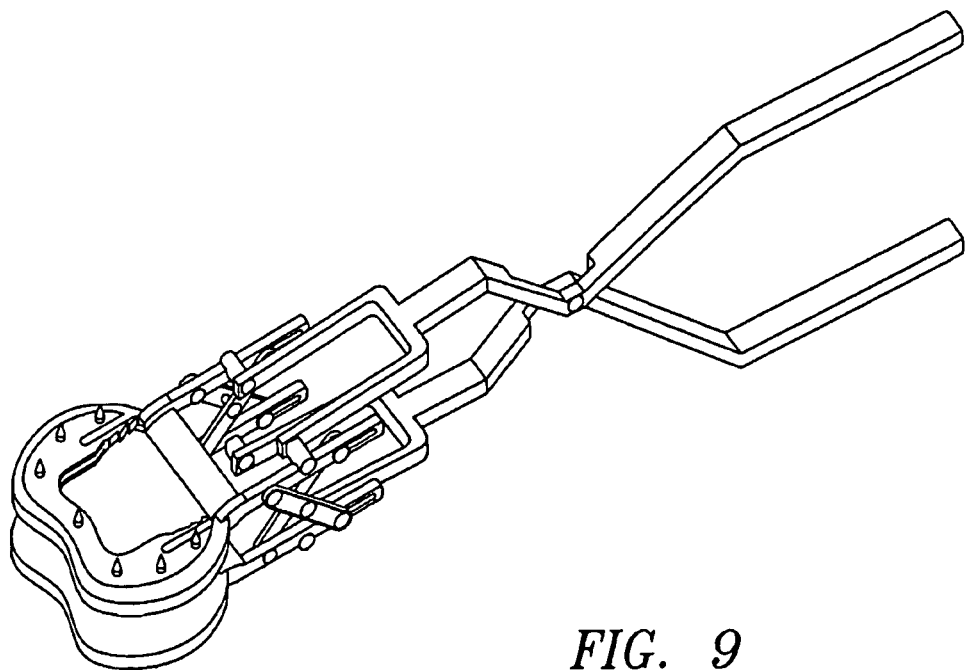

The spiked fixation element plates are loaded onto a delivery instrument 80 as shown in FIGS. 8 and 9 such that relative location and orientation between the upper spiked fixation element plate and the lower spiked fixation element plate are kept at a desired configuration. This configuration can be realized by providing appropriate mating features on the instrument and the corresponding mating features on the spiked plates. One of the possible mating features would be the pocket of the instrument and the corresponding external faces of the spiked plates as shown in FIG. 8. The pocket has the same internal face as the external face of spiked plates but with a slightly smaller size such that the spiked plate fits tightly into the pocket of the instrument. The instrument together with the spiked fixation plates is delivered to the area where the disc was removed and the spiked plates are pushed against the vertebra using the distracting motion of the instrument as shown in FIG. 9.

Figure 10:
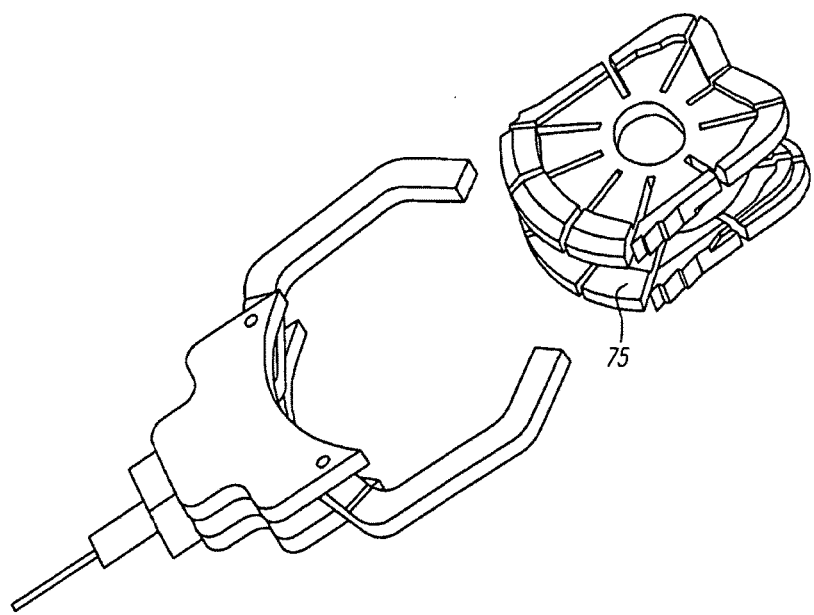
FIG. 10 provides a view of disc implantation device and disc according to an embodiment of the subject invention.

Once the spiked fixation plates are firmly fixed to the vertebra, the prosthetic disc 75 is held by a different tool and inserted into the implanted spiked fixation plates such that its gear teeth go through the matching gear teeth on the spiked fixation plates. FIG. 10 shows the tool holding the disc. The grippers in FIG. 10 hold the fiber area of the disc when it is in grasp position. The disc accommodating the grippers has the circular concave area in contact with the disc and is pushed into the spiked fixation plates through this contact. When the disc is inserted all the way into the spiked plates, the protruded rails on the disc at its most front side are in contact with the female railway of the spiked fixation plates and the disc is secured between the spiked fixation plates and therefore the vertebra.

Figure 11:
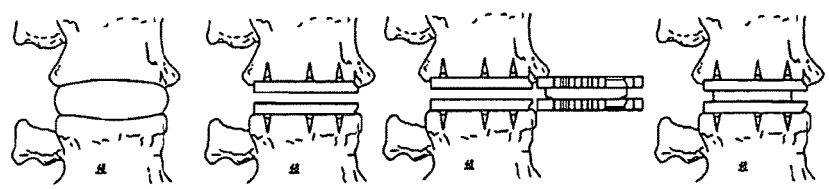
FIG. 11 provides sequential views of a disc being replaced with a prosthetic disc according to a method of the subject invention.

The above-described protocol is depicted in FIG. 11.

The above specifically reviewed protocol is merely representative of the protocols that may be employed for implanting devices according to the subject invention.

IV. Kits

Also provided are kits for use in practicing the subject methods, where the kits typically include one or more of the above prosthetic intervertebral disc devices (e.g., a plurality of such devices in different sizes), and/or components of the subject systems, e.g., fixation elements or components thereof, delivery devices, etc. as described above. The kit may further include other components, e.g., site preparation components, etc., which may find use in practicing the subject methods.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

It is evident from the above discussion and results that the subject invention provides a significantly improved prosthetic intervertebral disc. Significantly, the subject discs closely imitate the mechanical properties of the fully functional natural discs that they are designed to replace. The subject discs exhibit stiffness in the vertical direction, torsional stiffness, bending stiffness in sagittal plane, and bending stiffness in front plane, where the degree of these features can be controlled independently by adjusting the components of the discs, e.g., number of layers of fiber winding, pattern of fiber winding, distribution of impregnated polymer, and the types of impregnated polymers, etc. The fiber reinforced structure of the subject discs prevents the fatigue failure on the inside polymer and the surface treatment on the fiber of certain embodiments eliminates the debris problem, both of which are major disadvantages experienced with certain "rubber-type" artificial disks. The interface mechanism between the fixation plates and the disc plates of certain embodiments of the subject invention, e.g., as shown in FIG. 7, enables a very easy surgical operation. The surgeon simply needs to push the disc inward after fixing the spiked fixation plates onto the vertebrae. Such embodiments also enable easy removal of the disc in case the surgery brings about an ill effect. The gear teeth on the fixation elements are easily pushed from outside such that the gear engagement between the disc endplates and the fixation elements is released and the disc endplates are pulled out from the spiked plates. In view of the above and other benefits and features provided by the subject invention, it is clear that the subject invention represents a significant contribution to the art.

Part B

With reference to the embodiments illustrated in FIGS. 12-54, the subject prosthetic discs include upper and lower endplates separated by a core member. In one embodiment, the prosthetic disc comprises an integrated, single-piece structure. In another embodiment, the prosthetic disc comprises a two-piece structure including a lower endplate, and an upper endplate and the core member. The core may be assembled or integrated with either or the two endplates. The two-piece structure may be a constrained structure, wherein the upper endplate assembly is attached to the lower endplate in a manner that prevents relative rotation. Alternatively, the structure may be a semi-constrained or an unconstrained structure, wherein the upper endplate assembly is attached to the lower endplate in a manner that allows relative rotation. In yet another embodiment, the prosthetic disc comprises a three-piece structure including upper and lower endplates and a separable core member that is captured between the upper and lower endplates by a retaining mechanism. Finally, in yet another embodiment, the prosthetic disc comprises a four-piece structure including upper and lower endplates and two separable core assemblies which, together, form a core member. Those of ordinary skill in the art will recognize that five-piece, six-piece, or other multi-piece structures may be constructed by further division of the core member and/or the upper and lower endplates, or by the provision of additional components to the structure.

The implantation apparatus and methods are adapted to implant the prosthetic discs between two adjacent vertebral bodies of a patient. In a first embodiment, the apparatus includes three implantation tools used to prepare the two adjacent vertebral bodies for implantation and then to implant the prosthetic disc. A first tool, a spacer, is adapted to be inserted between and to separate the two adjacent vertebral bodies to create sufficient space for implanting the prosthetic disc. A second tool, a chisel, includes one or more wedge-shaped cutting blades located on its upper and/or lower surfaces that are adapted to create grooves in the inward facing surfaces of the two adjacent vertebral bodies. A third tool, a holder, includes an engagement mechanism adapted to hold the prosthetic disc in place while it is being implanted, and to release the disc once it has been implanted.

In another embodiment, the implantation apparatus includes a guide member that engages the lower endplate and that remains in place during a portion of the disc implantation process. A lower pusher member slidably engages the guide member and is used to advance the lower endplate into place between two adjacent vertebral bodies of a patient's spine. An upper pusher member is preferably coupled to the lower pusher member and is used to advance a first chisel into place opposed to the lower endplate between the two adjacent vertebral bodies. Once in place, an upward force is applied to the upper pusher member to cause the first chisel to engage the upper vertebral body and to chisel one or more grooves into its lower surface. A downward force is also applied to the lower pusher member to cause the lower endplate to engage the lower vertebral body and to become implanted. The upper pusher member and first chisel are then removed, as is the lower pusher member. Preferably, a second chisel is then advanced along the guide member and is used to provide additional preparation of the upper vertebral body. After the completion of the preparation by the first chisel and, preferably, the second chisel, the upper endplate and core members of the prosthetic disc are implanted using an upper endplate holder that is advanced along the guide member. After implantation, the upper endplate holder and guide member are removed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

I. Prosthetic Intervertebral Discs

The prosthetic intervertebral discs are preferably artificial or manmade devices that are configured or shaped so that they can be employed as replacements for an intervertebral disc in the spine of a vertebrate organism, e.g., a mammal, such as a human. The subject prosthetic intervertebral discs have dimensions that permit them to substantially occupy the space between two adjacent vertebral bodies that is present when the naturally occurring disc between the two adjacent bodies is removed, i.e., a disc void space. By substantially occupy is meant that the prosthetic disc occupies a sufficient volume in the space between two adjacent vertebral bodies that the disc is able to perform some or all of the functions performed by the natural disc for which it serves as a replacement. In certain embodiments, subject prosthetic discs may have a roughly bean shaped structure analogous to naturally occurring intervertebral body discs.

In many embodiments, the length of the prosthetic discs range from about 15 mm to about 50 mm, preferably from about 18 mm to about 46 mm, the width of the prosthetic discs range from about 12 mm to about 30 mm, preferably from about 14 mm to about 25 mm, and the height of the prosthetic discs range from about 3 mm to about 15 mm, preferably from about 5 mm to about 14 mm.

The prosthetic discs include upper and lower endplates separated by a core member. The resulting structure provides a prosthetic disc that functionally closely mimics a natural disc.

A. One-Piece Structure

Representative prosthetic intervertebral discs 100 having one-piece structures are shown in FIGS. 12 through 15. The prosthetic disc includes an upper endplate 110, a lower endplate 120, and a core member 130 retained between the upper endplate 110 and the lower endplate 120. One or more fibers 140 are wound around the upper and lower endplates to attach the endplates to one another. (For clarity, the fibers 140 are not shown in all of the Figures. Nevertheless, fibers 140, as shown, for example, in FIG. 12, are present in and perform similar functions in each of the embodiments described herein.) The fibers 140 preferably are not tightly wound, thereby allowing a degree of axial rotation, bending, flexion, and extension by and between the endplates. The core member 130 may be provided in an uncompressed or a pre-compressed state. An annular capsule 150 is optionally provided in the space between the upper and lower endplates, surrounding the core member 130 and the fibers 140. The upper endplate 110 and lower endplate 120 are generally flat, planar members, and are fabricated from a physiologically acceptable material that provides substantial rigidity. Examples of materials suitable for use in fabricating the upper endplate 110 and lower endplate 120 include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. Optionally, the endplates may be coated with hydroxylapatite, titanium plasma spray, or other coatings to enhance bony ingrowth.

As noted above, the upper and lower endplates typically have a length of from about 12 mm to about 45 mm, preferably from about 13 mm to about 44 mm, a width of from about 11 mm to about 28 mm, preferably from about 12 mm to about 25 mm, and a thickness of from about 0.5 mm to about 4 mm, preferably from about 1 mm to about 3 mm. The sizes of the upper and lower endplates are selected primarily based upon the size of the void between adjacent vertebral bodies to be occupied by the prosthetic disc. Accordingly, while endplate lengths and widths outside of the ranges listed above are possible, they are not typical.

The upper surface of the upper endplate 110 and the lower surface of the lower endplate 120 are preferably each provided with a mechanism for securing the endplate to the respective opposed surfaces of the upper and lower vertebral bodies between which the prosthetic disc is to be installed. For example, in FIG. 12, the upper endplate 110 includes a plurality of anchoring fins 111a-b. The anchoring fins 111a-b are intended to engage mating grooves that are formed on the surfaces of the upper and lower vertebral bodies to thereby secure the endplate to its respective vertebral body. The anchoring fins 111a-b extend generally perpendicularly from the generally planar external surface of the upper endplate 110, i.e., upward from the upper side of the endplate as shown in FIG. 12. In the FIG. 12 embodiment, the upper endplate 110 includes three anchoring fins 111a-c, although only two are shown in the cross-sectional view. A first of the anchoring fins, 111a, is disposed near an external edge of the external surface of the upper endplate and has a length that approximates the width of the upper endplate 110. A second of the anchoring fins, 111b, is disposed at the center of external surface of the upper endplate and has a relatively shorter length, substantially less than the width of the upper endplate 110. Each of the anchoring fins 111a-b has a plurality of serrations 112 located on the top edge of the anchoring fin. The serrations 112 are intended to enhance the ability of the anchoring fin to engage the vertebral body and to thereby secure the upper endplate 110 to the spine.

Similarly, the lower surface of the lower endplate 120 includes a plurality of anchoring fins 121a-b. The anchoring fins 121a-b on the lower surface of the lower endplate 120 are identical in structure and function to the anchoring fins 111a-b on the upper surface of the upper endplate 110, with the exception of their location on the prosthetic disc. The anchoring fins 121a-b on the lower endplate 120 are intended to engage mating grooves formed on the lower vertebral body, whereas the anchoring fins 111a-b on the upper endplate 110 are intended to engage mating grooves on the upper vertebral body. Thus, the prosthetic disc 100 is held in place between the adjacent vertebral bodies.

The anchoring fins 111, 121 may optionally be provided with one or more holes or slots 115, 125. The holes or slots help to promote bony ingrowths that bond the prosthetic disc 100 to the vertebral bodies.

Figure 13A:
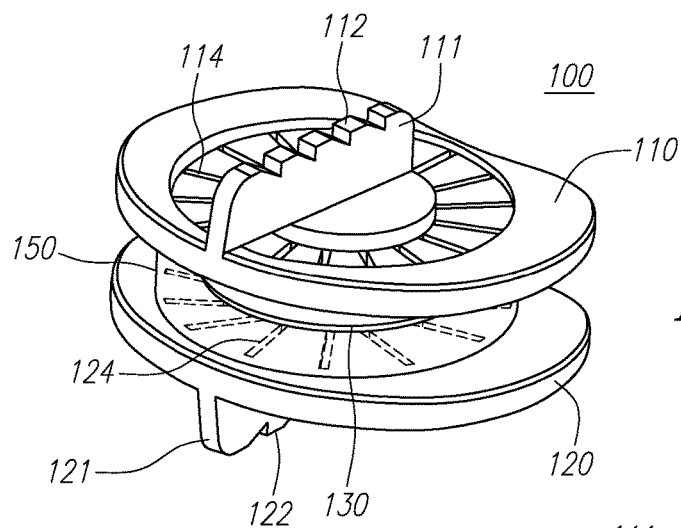
FIG. 13A provides a three-dimensional view of a prosthetic disc having a one-piece structure including a single anchoring fin on each of the upper and lower endplates.
Figure 13B:
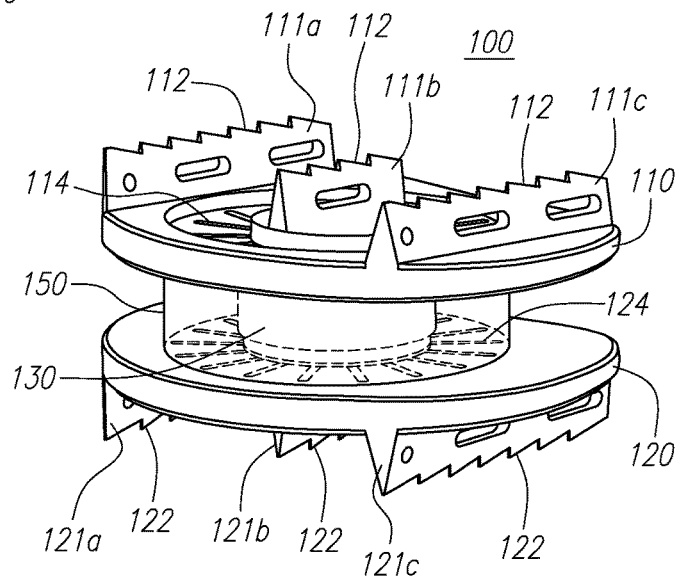
FIG. 13B provides a three-dimensional view of a prosthetic disc having a one-piece structure including three anchoring fins on each of the upper and lower endplates.
Figure 13C:
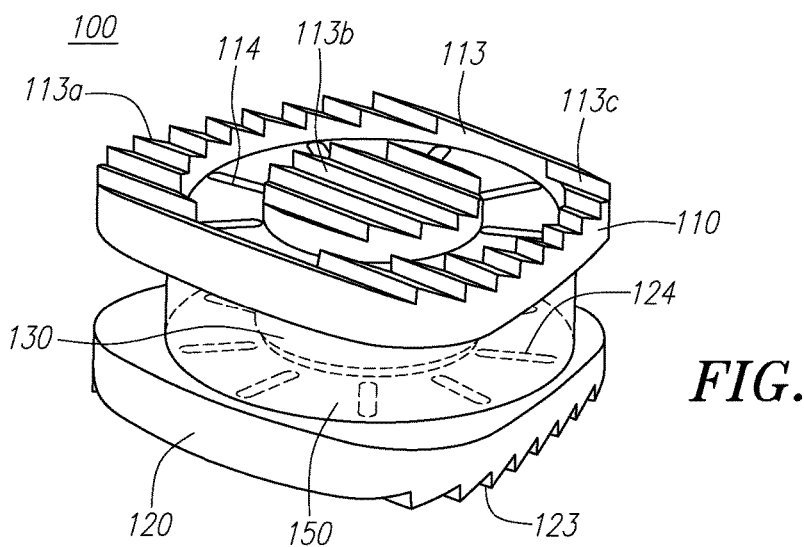
FIG. 13C provides a three-dimensional view of a prosthetic disc having a one-piece structure including a serrated surface on each of the upper and lower endplates.

Turning to FIGS. 13A-C, there are shown several alternative mechanisms for securing the endplates to the respective opposed surfaces of the upper and lower vertebral bodies between which the prosthetic disc is to be installed. In FIG. 13A, each of the upper endplate 110 and lower endplate 120 is provided with a single anchoring fin 111, 121. The anchoring fins 111, 121 are located along a center line of the respective endplates, and each is provided with a plurality of serrations 112, 122 on its upper edge. The single anchoring fins 111, 121 are intended to engage grooves formed on the opposed surface of the upper and lower vertebral bodies, as described above. In FIG. 13B, each of the upper endplate 110 and lower endplate 120 is provided with three anchoring fins 111a-c, 121a-c. The FIG. 13B prosthetic disc is the same as the prosthetic disc shown in FIG. 1, but it is shown in perspective rather than cross-section. Thus, the structure and function of the anchoring fins 111a-c and 121a-c are as described above in relation to FIG. 12. Finally, in FIG. 13C, each of the upper endplate 110 and lower endplate 120 is provided with a plurality of serrations 113, 123 over a portion of the exposed external surface of the respective endplate. The serrations 113, 123 are intended to engage the opposed surfaces of the adjacent vertebral bodies to thereby secure the endplates in place between the vertebral bodies. The serrations 113, 123 may be provided over the entire external surface of each of the upper and lower endplates, or they may be provided over only a portion of those surfaces. For example, in FIG. 13C, the serrations 113 on the upper surface of the upper endplate 110 are provided over three major areas, a first area 113a near a first edge of the upper endplate 110, a second area 113b near the center of the upper endplate 110, and a third area near a second edge of the endplate 113c.

Figure 54:
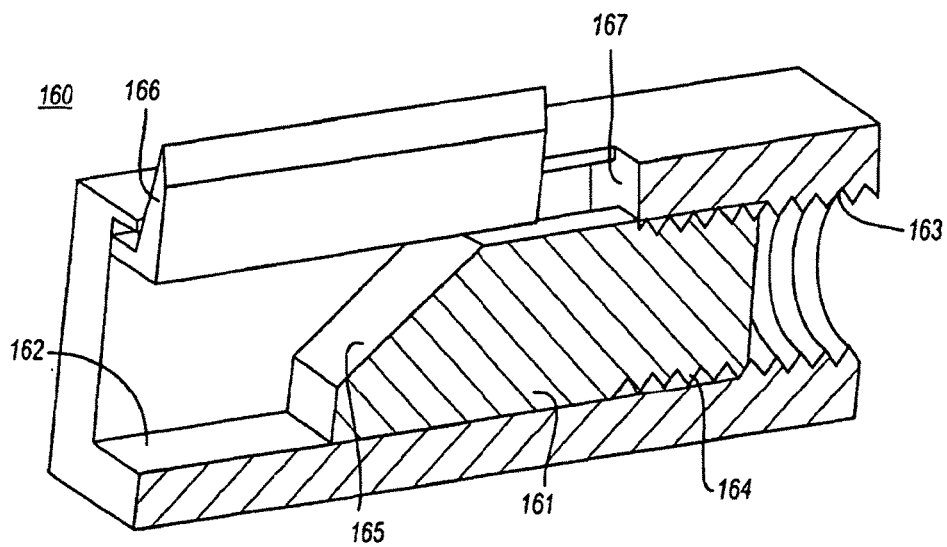
FIG. 54 provides a cross-sectional illustration of a mechanism for deploying and retracting fins and/or spikes located on prosthetic disc endplate.

Turning to FIG. 54, in an optional embodiment, the anchoring fins 111 are selectively retractable and extendable by providing a deployment mechanism 160 that is associated with the upper endplate 110. A similar mechanism may be used on the lower endplate 120. The deployment mechanism includes a slider 161 that slides within a channel 162 formed in the upper endplate 110. The channel 162 includes a threaded region 163, and the slider 161 includes matching threads 164, thereby providing a mechanism for advancing the slider 161 within the channel 162. As the slider 161 is advanced within the channel 162, a tapered region 165 engages the bottom surface of a deployable fin 166. Further advancement of the slider 161 causes the deployable fin 166 to be raised upward within a slot 167 on the upper surface of the upper endplate 110. Reversing the deployment mechanism 160 causes the fin 166 to retract. The deployment mechanism 160 may also be used in conjunction with spikes, serrations, or other anchoring devices. In an alternative embodiment, the threaded slider 161 of the deployment mechanism may be replaced with a dowel pin that is advanced to deploy the fin 166. Other advancement mechanisms are also possible.

Figure 14A:
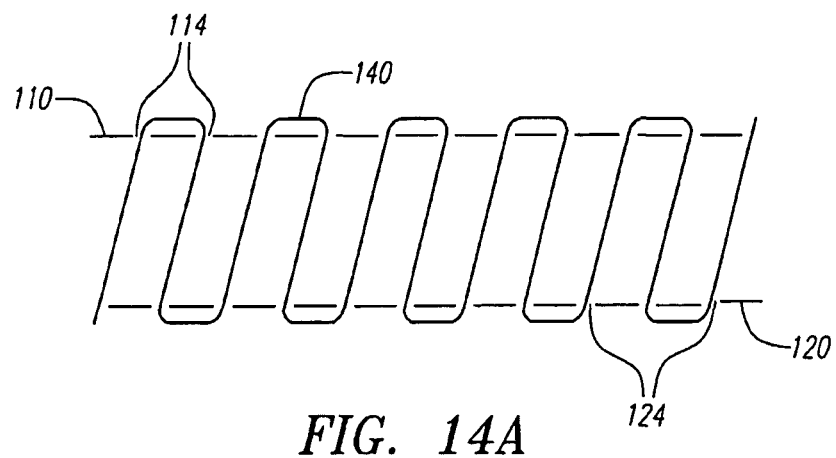
FIGS. 14A and B provide illustrations of uni-directional and bi-directional fiber winding patterns.
Figure 14B:
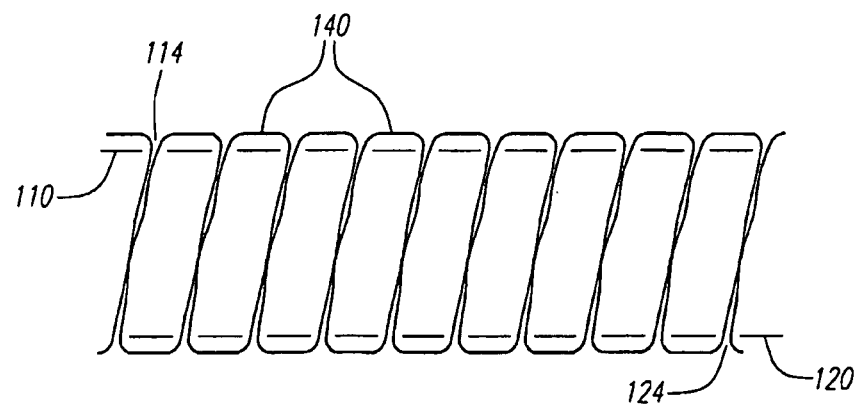

Returning to FIG. 12, the upper endplate 110 contains a plurality of slots 114 through which the fibers 140 may be passed through or wound, as shown. The actual number of slots 114 contained on the endplate is variable. Increasing the number of slots will result in an increase in the circumferential density of the fibers holding the endplates together. In addition, the shape of the slots may be selected so as to provide a variable width along the length of the slot. For example, as shown in FIG. 12a, the width of the slots 114 may taper—e.g., in a tapered section 107c—from a wider inner end 107a to a narrow outer end 107b, or vice versa. FIG. 12b shows a slot 114 having a first part 109a, second part 109b, and third part 109c. Additionally, the fibers may be wound multiple times within the same slot, thereby increasing the radial density of the fibers. In each case, this improves the wear resistance and increases the torsional and flexural stiffness of the prosthetic disc, thereby further approximating natural disc stiffness. In addition, the fibers 140 may be passed through or wound on each slot, or only on selected slots, as needed. Two exemplary winding patterns are shown in FIGS. 14A and 14B. In FIG. 14A, the fibers 140 are wound in a uni-directional manner, which closely mimics natural annular fibers found in a natural disc. In FIG. 14B, the fibers 140 are wound bi-directionally. Other winding patterns, either single or multi-directional, are also possible.

As described above, the purpose of the fibers 140 is to hold the upper endplate 110 and lower endplate 120 together and to limit the range-of-motion to mimic the range-of-motion of a natural disc. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 140 are generally elongate fibers having a diameter that ranges from about 100 µm to about 500 µm, and preferably about 200 µm to about 400 µm. Optionally, the fibers may be injection molded with an elastomer to encapsulate the fibers, thereby providing protection from tissue ingrowth and improving torsional and flexural stiffness, or the fibers may be coated with one or more other materials to improve fiber stiffness and wear. Additionally, the core may be injected with a wetting agent such as saline to wet the fibers and facilitate the mimicking of the viscoelastic properties of a natural disc.

The fibers 140 may be fabricated from any suitable material. Examples of suitable materials include polyester (e.g., Dacron), polyethylene, polyaramid, poly-paraphenylene terephthalamide (e.g., Kevlar), carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers 140 may be terminated on an endplate by tying a knot in the fiber on the superior surface of an endplate. Alternatively, the fibers 140 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

The core member 130 is intended to provide support to and to maintain the relative spacing between the upper endplate 110 and lower endplate 120. The core member 130 is made of a relatively compliant material, for example, polyurethane or silicone, and is typically fabricated by injection molding. A preferred construction for the core member includes a nucleus formed of a hydrogel and an elastomer reinforced fiber annulus. For example, the nucleus, the central portion of the core member 130, may comprise a hydrogel material such as a water absorbing polyurethane, polyvinyl alcohol (PVA), polyethylene oxide (PEO), polyvinylpyrrolidone (PVP), polyacrylamide, silicone, or PEO based polyurethane. The annulus may comprise an elastomer, such as silicone, polyurethane or polyester (e.g., Hytrel), reinforced with a fiber, such as polyethylene (e.g., ultra high molecular weight polyethylene, UHMWPE), polyethylene terephthalate, or poly-paraphenylene terephthalamide (e.g., Kevlar).

The shape of the core member 130 is typically generally cylindrical or bean-shaped, although the shape (as well as the materials making up the core member and the core member size) may be varied to obtain desired physical or performance properties. For example, the core member 130 shape, size, and materials will directly affect the degree of flexion, extension, lateral bending, and axial rotation of the prosthetic disc.

Figure 15A:
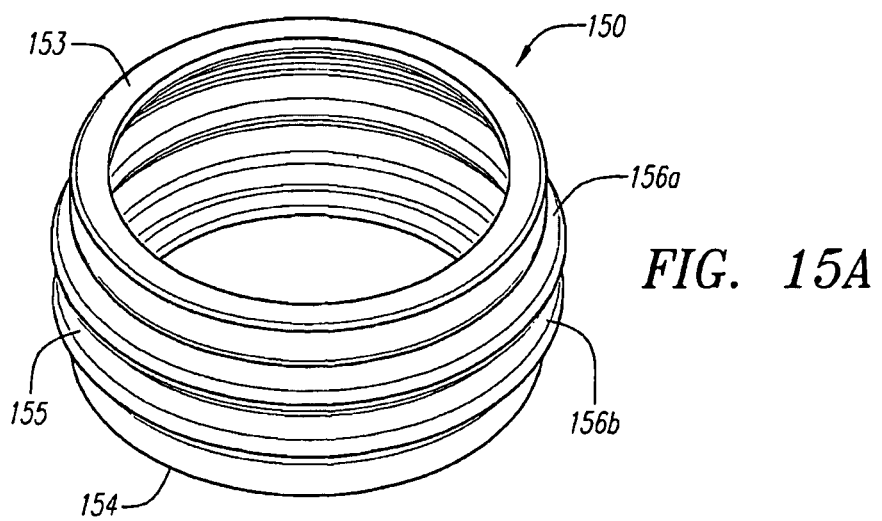
FIGS. 15A-C provide illustrations of an annular capsule.
Figure 15B:
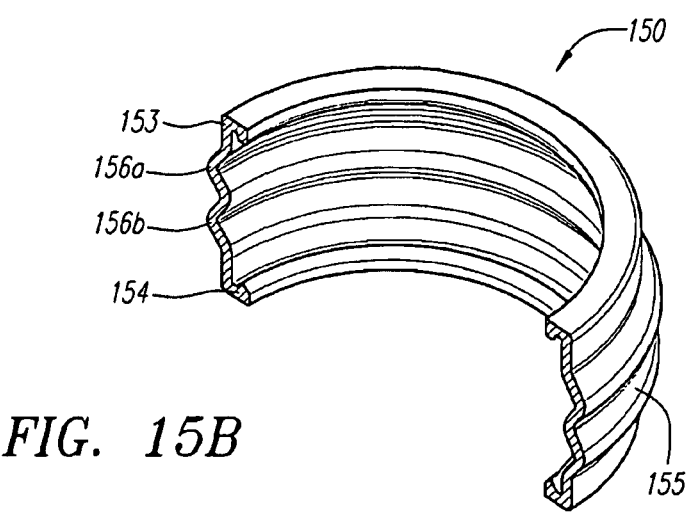
Figure 15C:
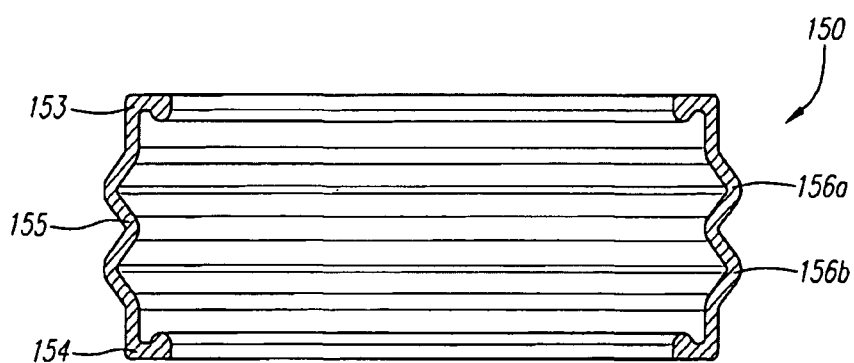

The annular capsule 150 is preferably made of polyurethane or silicone and may be fabricated by injection molding, two-part component mixing, or dipping the endplate-core-fiber assembly into a polymer solution. A preferred annular capsule 150 is shown in FIGS. 15A-C. As shown, the annular capsule is generally cylindrical, having an upper circular edge 153, a lower circular edge 154, and a generally cylindrical body 155. In the embodiment shown in the Figures, the body 155 has two bellows 156a-b formed therein. Alternative embodiments have no bellows, one bellow, or three or more bellows. A function of the annular capsule is to act as a barrier that keeps the disc materials (e.g., fiber strands) within the body of the disc, and that keeps natural in-growth outside the disc.

Figure 13D:
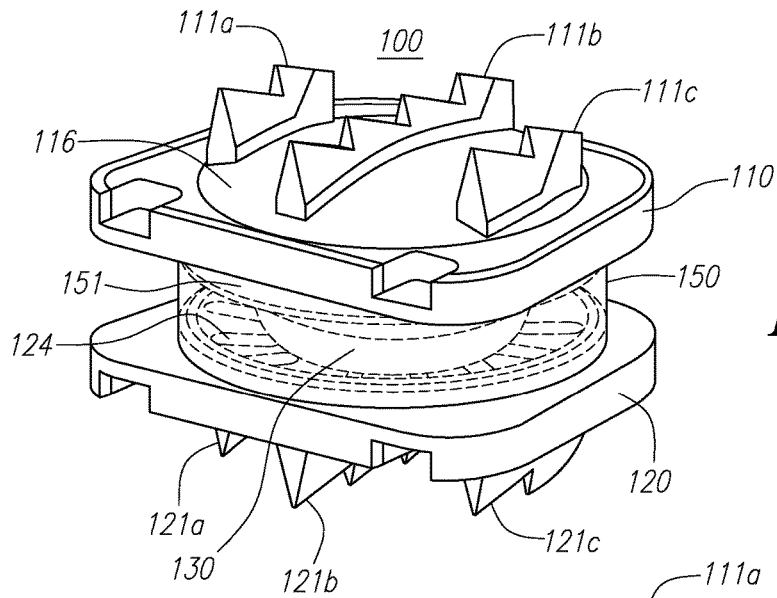
FIG. 13D provides a three-dimensional view of a prosthetic disc having a one-piece structure including a superior dome.
Figure 13E:
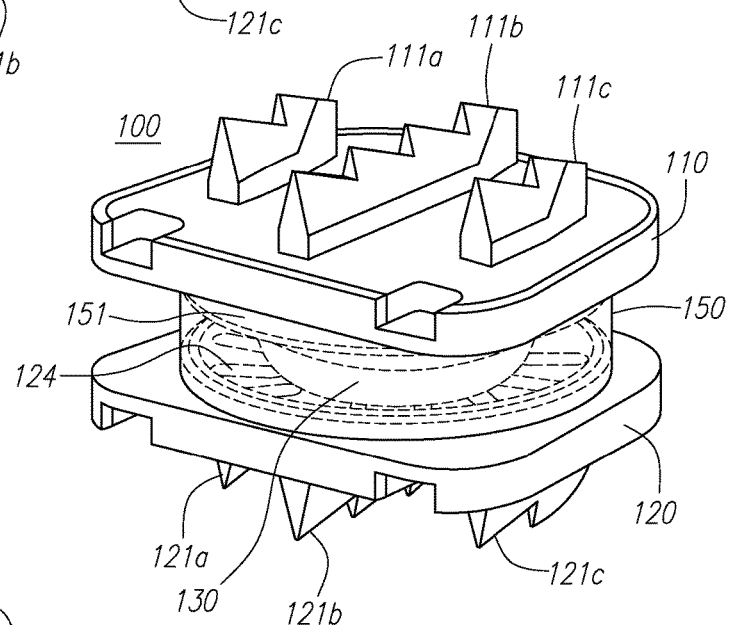
FIG. 13E provides a three-dimensional view of the prosthetic disc having a one-piece structure of FIG. 13D, having no superior dome.
Figure 13F:
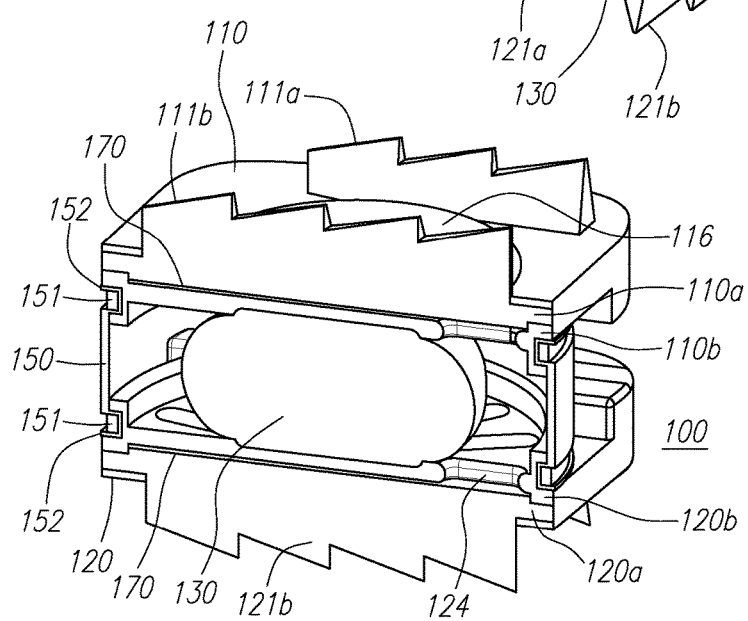
FIG. 13F provides a three-dimensional cross-sectional view of the prosthetic disc having a one-piece structure shown in FIG. 13D.

Additional examples of the one-piece structure embodiment of the prosthetic disc are illustrated in FIGS. 13D-F. Each of these embodiments includes an upper endplate 110, lower endplate 120, and a core member 130, as described above. The upper endplate 110 includes an outer portion 110*a* and an inner portion 110*b*, and the lower endplate also includes an outer portion 120*a* and an inner portion 120*b*. The inner and outer portions of each of the endplates are bonded to each other by methods known to those of skill in the art. Each of the endplates 110, 120 also includes anchoring fins 111*a-c*, 121*a-c* on the upper surface of the upper endplate 110 and the lower surface of the lower endplate 120, as also described above. Additionally, with reference to FIG. 13D, a superior dome 116 is provided on the upper surface of the upper endplate 110. The superior dome 116 is a generally convex portion that extends upward from the upper surface of the upper endplate 110. The superior dome 116 is optional, and functions by filling space between the upper endplate 110 and the vertebral body upon implantation to help approximate the upper endplate 110 to the natural anatomy. The size and shape of the superior dome 116 may be varied according to need. As shown in FIG. 13D, the superior dome 116 is generally convex and has a maximum height (distance above the generally flat upper surface portion of the upper endplate) of approximately one-half the height of the anchoring fin 111*b*. The superior dome 116 may be centered in the middle of the upper endplate 110, as shown in FIG. 2D, or it may be shifted to one side or another, depending on need.

With particular reference to FIG. 13F, a polymer film 170 is sandwiched between the outer portion 10*a* and inner portion 10*b* of the upper endplate 110, and another polymer film 170 is sandwiched between the outer portion 120*a* and inner portion 120*b* of the lower endplate 120. The polymer films 170 are adapted to tightly adhere, either mechanically or chemically, to the fibers 140 wound through the slots 114, 124 formed in the upper endplate 110 and lower endplate 120.

FIGS. 13D-F provide additional detail concerning the annular capsule 150. As shown there, the annular capsule 150 seals the interior space between the upper and lower endplates. The annular capsule 150 is retained on the disc by a pair of retaining rings 151 that engage a mating pair of external facing grooves 152 on the upper and lower endplates. (See FIG. 13F). Although the retaining rings may be of any suitable cross-section (e.g., round, triangular, square, etc.), the examples shown in FIG. 13F have a rectangular cross-section. The rectangular shape is believed to provide relatively better gasket retention and is more easily manufactured.

Figure 13G:
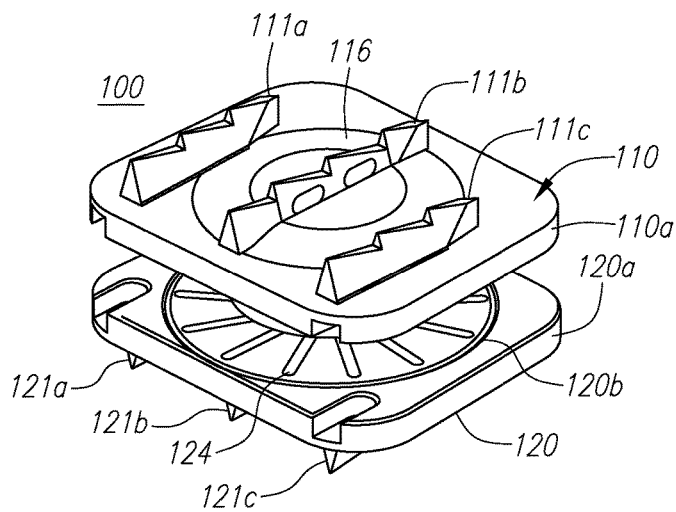
FIG. 13G provides a three-dimensional view of a prosthetic disc having a one-piece structure design without a gasket retaining ring.
Figure 13H:
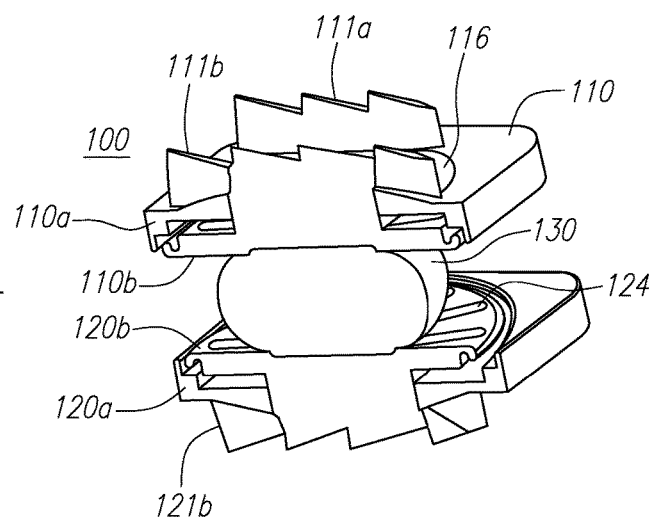
FIG. 13H provides a three-dimensional cross-sectional view of the prosthetic disc having a one-piece structure shown in FIG. 2G.

FIGS. 13G and 13H illustrate still further examples of the one-piece structure embodiment of the prosthetic disc. In the examples shown there, the upper endplate 110 includes an outer portion 110*a* and an inner portion 110*b*. Similarly, the lower endplate 120 includes an outer portion 120*a* and an inner portion 120*b*. The two portions 110*a-b*, 120*a-b* of each of the upper and lower endplates mate together to form the integrated upper endplate 110 and lower endplate 120. Preferably, the two portions 110*a-b*, 120*a-b* of the upper and lower endplates 110, 120 are joined together by welding, e.g., laser welding or some similar process. An advantage that may be obtained with this structure is the ability to retain the annular capsule 150 (not shown in FIGS. 13G-H) without the need for a separate retaining ring. For example, the upper edge of the annular capsule may be captured and retained between the outer portion 110*a* and inner portion 110*b* of the upper endplate 110 when they are attached to one another. Similarly, the lower edge of the annular capsule may be captured and retained between the outer portion 120*a* and inner portion 120*b* of the lower endplate 120 when those components are attached to one another. In this manner, the annular capsule is held in place between the upper and lower endplates by the compression forces retaining the upper and lower edges of the annular capsule.

Figure 13I:
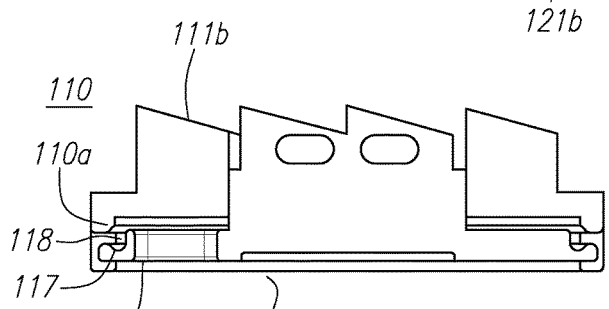
FIG. 13I provides a cross-sectional view of an upper endplate of a prosthetic disc having a one-piece structure design without a gasket retaining ring.
Figure 13J:
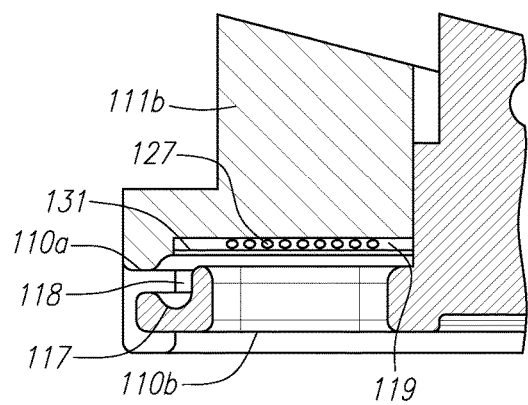
FIG. 13J provides an inset view of a portion of the upper endplate shown in FIG. 2I.

An optional structure for retaining the annular capsule 150 is illustrated in FIGS. 13I-J. There, an upper endplate 110 is shown including an outer portion 110*a* and an inner portion 110*b*. The upper surface of the inner portion 110*b* of the upper endplate 110 is provided with an annular groove 117 that extends about the periphery of the inner portion 110*b*. The annular groove 117 cooperates with the bottom surface of the outer portion 110*a* of the upper endplate 110 to create an annular space 118. A similar structure, not shown in the drawings, may be provided on the lower endplate 120. The annular capsule 150 (not shown in FIGS. 13I-J) may advantageously be formed having a bead, i.e., a ball-like termination about its upper and lower edge, (also not shown in the drawings), that occupies the annular space 118 formed on the upper and lower endplates 110, 120. The cooperation of the annular space 118 with the bead formed on the annular capsule 150 creates a stronger and more secure retaining force for retaining the upper and lower edge of the annular capsule 150 by the upper and lower endplates 110, 120. Alternatively, the annular capsule may be retained by adhesives with or without the endplate compression already described.

Another optional feature of the present invention is the placement of the fibers in a state of tensile fatigue upon fabrication so as to minimize long-term wear. For example, in the embodiment of FIGS. 13I-J, a material 131 such as a metal plate or a polymer film may be positioned within space 119 of upper portion 110*a* of the endplate and between the fibers 127 and the surface of the endplate. The material may initially be in a form, e.g., gel or emulsion, so as to coat and impregnate the fibers. With such material, the fibers are caused to impinge upon the endplate thereby reducing their susceptibility to movement during use of the disc. As an additional optional feature, each of the endplates may be made up of two plates that are selectively rotationally displaceable relative to each other. In this structure, a slight rotation of one of the plates relative to the other has the effect of changing the size and/or shape of the slots formed on the combined endplate. Thus, the user is able to select a desired set of dimensions of the slots.

Figure 13K:
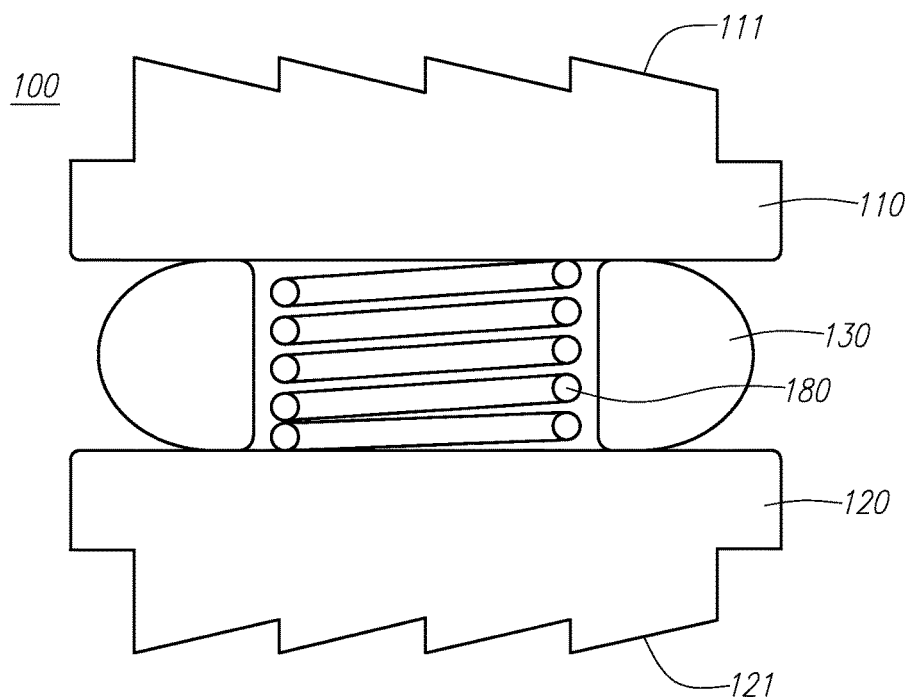
FIG. 13K provides a cross-sectional illustration of a prosthetic disc having a one-piece structure design with a center spring.
Figure 13L:
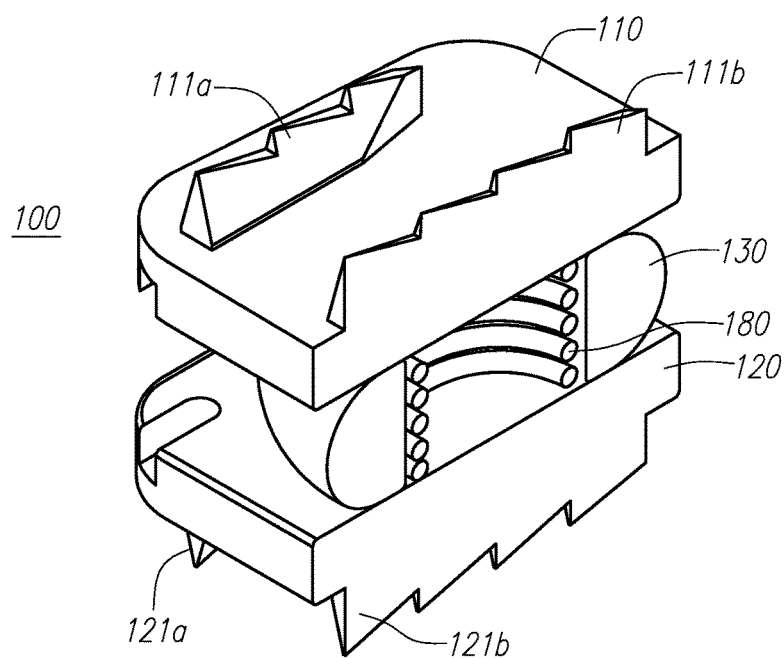
FIG. 13L provides a three-dimensional cross-sectional illustration of the prosthetic disc having a one-piece structure shown in FIG. 13K.

FIGS. 13K-L illustrate another optional feature that may be incorporated in the one-piece structure embodiment of the prosthetic disc. In the examples shown there, a spring 180 is located coaxially with the core member 130 between the upper endplate 110 and lower endplate 120. In this example, the core member 130 is in the form of a toroid, thus having a space at its center. The spring 180 is placed in the space at the center of the core member 130, with each being retained between the upper endplate 110 and lower endplate 120. The spring 180 provides a force biasing the two endplates apart, and having performance characteristics and properties that are different from those provided by the core member 130. Those characteristics may be varied by, for example, selecting a spring 180 having different dimensions, materials, or a different spring constant. In this way, the spring 180 provides an additional mechanism by which the performance of the prosthetic disc may be varied in order to approximate that of a natural disc.

Figure 50A:
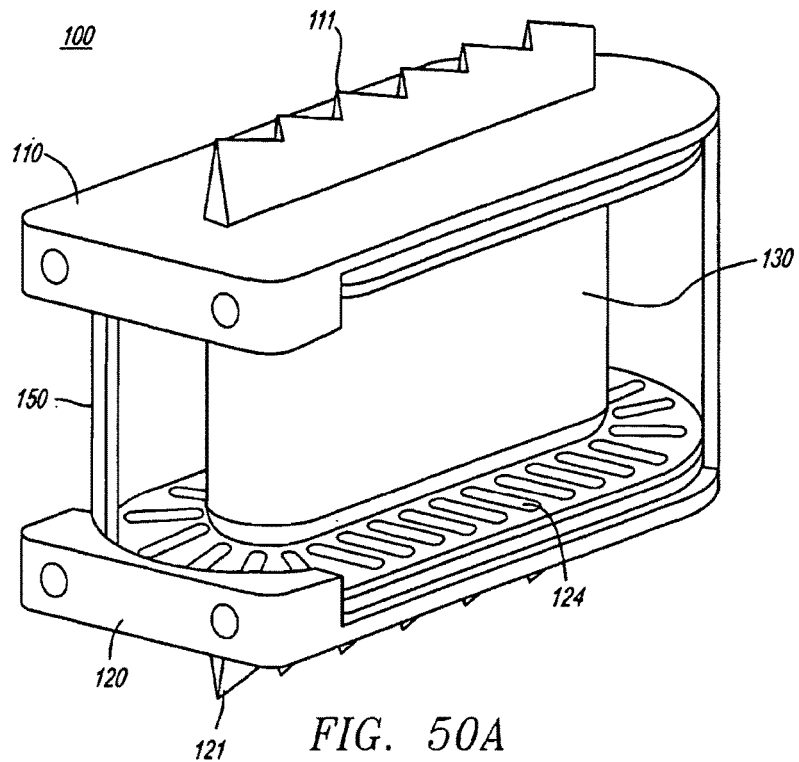
FIG. 50A provides a three-dimensional view of a preferred prosthetic disc for use with a minimally invasive surgical procedure.
Figure 50B:
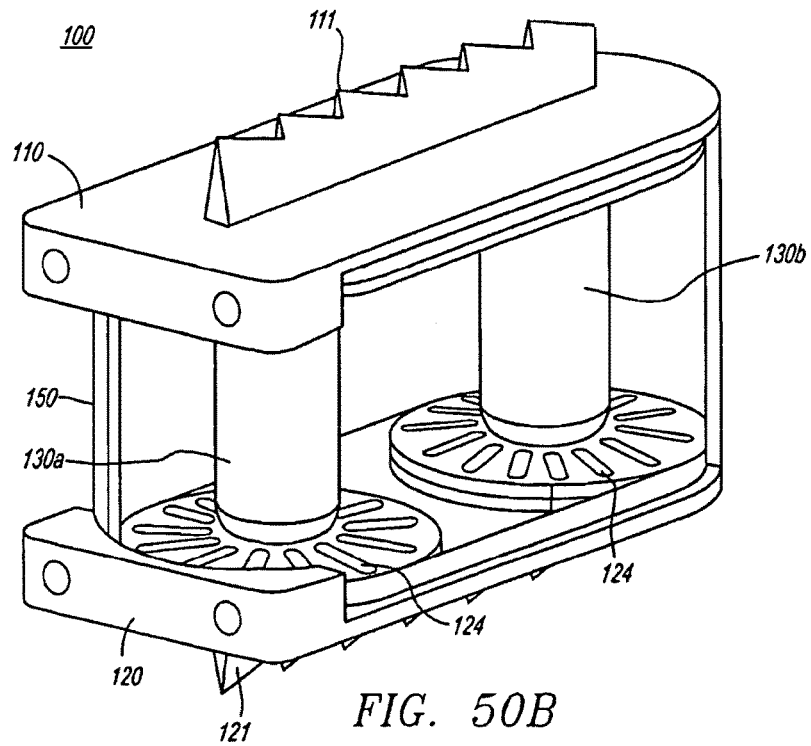
FIG. 50B provides a three-dimensional view of another preferred prosthetic disc for use with a minimally invasive surgical procedure.

Turning to FIGS. 50A-B, additional examples of the one-piece structure embodiment of the prosthetic discs are shown. The discs illustrated in FIGS. 50A-B are particularly adapted in size and shape for implantation by minimally invasive surgical procedures, as described below. Aside from their size and shape, the structures of the examples shown in FIGS. 50A-B are similar to those described above, including an upper endplate 110, lower endplate 120, a core member 130, and an annular capsule 150. Each of the upper and lower endplates 110, 120 is provided with an anchoring fin 111, 121 extending from its surface over most of the length of the endplate. Although not shown in the drawings, these examples also preferably include fibers 140 wound between and connecting the upper endplate 110 to the lower endplate 120.

In the example shown in FIG. 50A, a single elongated core member is provided, whereas the example structure shown in FIG. 50B has a dual core including two generally cylindrical core members 130a, 130b. It is believed that the dual core structure (FIG. 50B) better simulates the performance characteristics of a natural disc. In addition, the dual core structure is believed to provide less stress on the fibers 140 relative to the single core structure (FIG. 50A). Each of the exemplary prosthetic discs shown in FIGS. 50A-B has a greater length than width. Exemplary shapes to provide these relative dimensions include rectangular, oval, bullet-shaped, or others. This shape facilitates implantation of the discs by the minimally invasive procedures described below.

The one-piece structure embodiment of the prosthetic disc is implanted by a surgical procedure. After removing the natural disc, grooves are formed in the superior and inferior vertebrae between which the prosthetic disc is to be implanted. The prosthetic disc is then inserted into the void, while aligning the anchoring fins 111, 121 with the grooves formed on the vertebral bodies. The anchoring fins cause the prosthetic disc to be secured in place between the adjacent vertebral bodies. The prosthetic disc has several advantages over prior art artificial discs, as well as over alternative treatment procedures such as spinal fusion. For example, the prosthetic discs described herein provide compressive compliance similar to that of a natural spinal disc. In addition, the motions in flexion, extension, lateral bending, and axial rotation are also restricted in a manner near or identical to those associated with a natural disc.

B. Two-Piece Structure

Representative prosthetic intervertebral discs 200 having two-piece structures are shown in FIGS. 16 through 20. The components and features included in the two-piece prosthetic discs are very similar to those of the one-piece disc described above. A primary difference between the devices is that the two-piece prosthetic disc contains two separable components, whereas the one-piece prosthetic disc contains a single, integrated structure. In particular, and as described more fully below, the lower endplate of the two-piece prosthetic disc is separated into an inner lower endplate 220a, and an outer lower endplate 220b (see FIGS. 16-20), whereas there is only a single lower endplate 120 in the one-piece disc (see FIGS. 12 and 13A-C).

Turning to FIGS. 16-20, the two-piece prosthetic disc includes two primary, separable components: the outer lower endplate 220b, and an upper subassembly 205. In a first embodiment of the two-piece prosthetic disc, shown in FIGS. 16-18, the upper subassembly 205 is constrained, i.e., it cannot freely rotate in relation to the outer lower endplate 220b. In a second embodiment of the two-piece prosthetic disc, shown in FIGS. 19-20, the upper subassembly 205 is unconstrained, i.e., it can substantially freely rotate in relation to the outer lower endplate 220b.

The upper subassembly includes the inner lower endplate 220a, an upper endplate 210, and a core member 230 retained between the upper endplate 210 and the inner lower endplate 220a. One or more fibers 240 are wound around the upper and inner lower endplates to attach the endplates to one another. The fibers 240 preferably are not tightly wound, thereby allowing a degree of axial rotation, bending, flexion, and extension by and between the endplates. The core member 230 is preferably pre-compressed. An annular capsule 250 is optionally provided in the space between the upper and inner lower endplates, surrounding the core member 230 and the fibers 240. Alternatively, an outer ring or gasket (not shown in the drawings) may optionally be provided in place of the annular capsule 250.

The upper endplate 210 and outer lower endplate 220b are generally flat, planar members, and are fabricated from a physiologically acceptable material that provides substantial rigidity. Examples of materials suitable for use in fabricating the upper endplate 210 and outer lower endplate 220b include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. Optionally, the endplates may be coated with hydroxylapatite, titanium plasma spray, or other coatings to enhance bony ingrowth.

As noted above, the upper and outer lower endplates typically have a length of from about 12 mm to about 45 mm, preferably from about 13 mm to about 44 mm, a width of from about 11 mm to about 28 mm, preferably from about 12 mm to about 25 mm, and a thickness of from about 0.5 mm to about 4 mm, preferably from about 1 mm to about 3 mm. The sizes of the upper and outer lower endplates are selected primarily based upon the size of the void between adjacent vertebral bodies to be occupied by the prosthetic disc. Accordingly, while endplate lengths and widths outside of the ranges listed above are possible, they are not typical.

Figure 16:
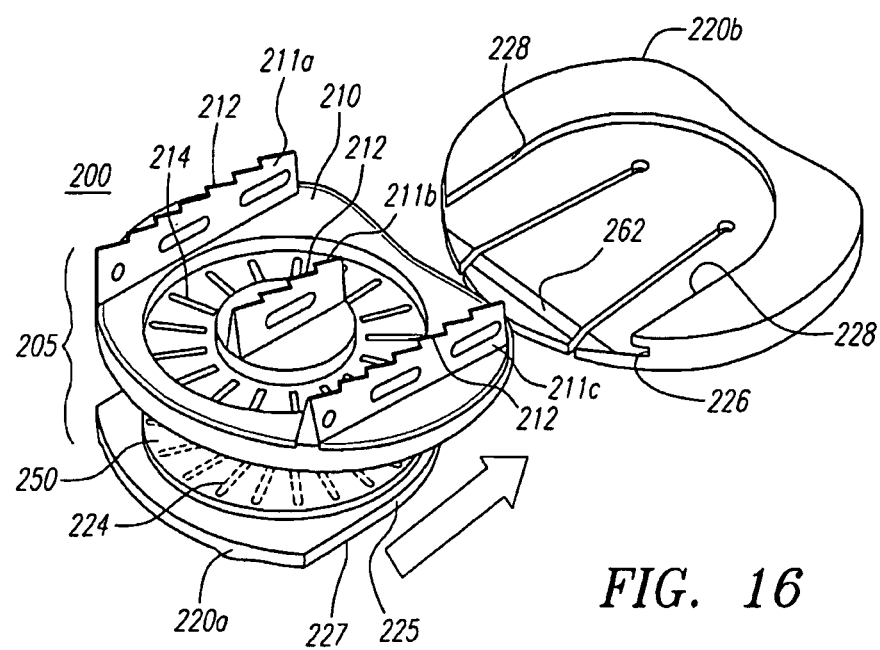
FIG. 16 provides a three-dimensional view of a prosthetic disc having a two-piece structure.
Figure 17:
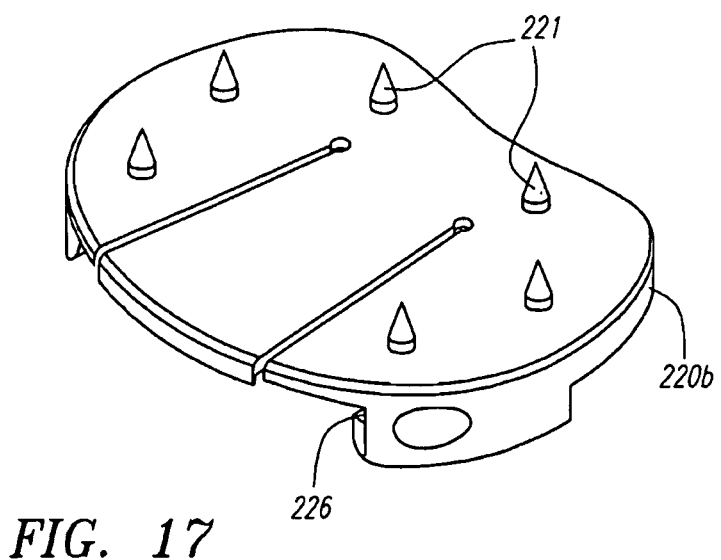
FIG. 17 provides a three-dimensional view of an outer lower endplate of the prosthetic disc shown in FIG. 16.
Figure 18:
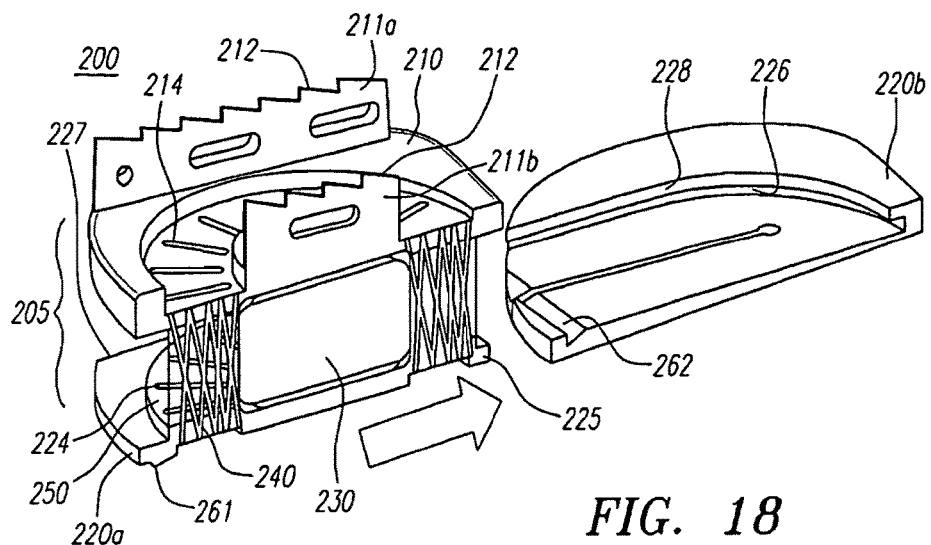
FIG. 18 provides a cross-sectional view of a prosthetic disc having a two-piece constrained structure.

The upper surface of the upper endplate 210 and the lower surface of the outer lower endplate 220b are preferably each provided with a mechanism for securing the endplate to the respective opposed surfaces of the upper and lower vertebral bodies between which the prosthetic disc is to be implanted. For example, as shown in FIGS. 16 and 18-20, the upper endplate 210 includes a plurality of anchoring fins 211a-c. The anchoring fins 211a-c are intended to engage mating grooves that are formed on the surfaces of the upper and lower vertebral bodies to thereby secure the endplate to its respective vertebral body. The anchoring fins 211a-c extend generally perpendicular from the generally planar external surface of the upper endplate 210, i.e., upward from the upper side of the endplate as shown in FIG. 16. In the FIG. 16 embodiment, the upper endplate 210 includes three anchoring fins 211a-c. The first and third of the anchoring fins, 211a and 211c, are disposed near the external edges of the external surface of the upper endplate 210 and have lengths that approximate the width of the upper endplate 210. The second of the anchoring fins, 211b, is disposed at the center of external surface of the upper endplate and has a relatively shorter length, substantially less than the width of the upper endplate 210. Each of the anchoring fins 211a-c has a plurality of serrations 212 located on the top edge of the anchoring fin. The serrations 212 are intended to enhance the ability of the anchoring fin to engage the vertebral body and to thereby secure the upper endplate 210 to the vertebral body.

The lower surface of the outer lower endplate 220b includes a plurality of anchoring spikes 221. The anchoring spikes 221 on the lower surface of the outer lower endplate 220b are intended to engage the surface of the lower vertebral body, while the anchoring fins 211a-c on the upper endplate 210 are intended to engage mating grooves on the upper vertebral body. Thus, the prosthetic disc 200 is held in place between the adjacent vertebral bodies.

Alternatively, the upper endplate 210 and outer lower endplate 220b of the two-piece prosthetic disc may employ one of the alternative securing mechanisms shown in FIGS. 13A-C. As described above, in FIG. 13A, each of the upper endplate 110 and lower endplate 120 is provided with a single anchoring fin 111, 121. The anchoring fins 111, 121 are located along a center line of the respective endplates, and each is provided with a plurality of serrations 112, 122 on its upper edge. The single anchoring fins 111, 121 are intended to engage grooves formed on the opposed surface of the upper and lower vertebral bodies, as described above. In FIG. 13B, each of the upper endplate 110 and lower endplate 120 is provided with three anchoring fins 111a-c, 121a-c. The FIG. 13B prosthetic disc is the same as the prosthetic disc shown in FIG. 12, but it is shown in perspective rather than cross-section. Thus, the structure and function of the anchoring fins 111a-c and 121a-c are as described above in relation to FIG. 12. Finally, in FIG. 13C, each of the upper endplate 110 and lower endplate 120 is provided with a plurality of serrations 113, 123 over a portion of the exposed external surface of the respective endplate. The serrations 113, 123 are intended to engage the opposed surfaces of the adjacent vertebral bodies to thereby secure the endplates in place between the vertebral bodies. The serrations 113, 123 may be provided over the entire external surface of each of the upper and lower endplates, or they may be provided over only a portion of those surfaces. For example, in FIG. 13C, the serrations 113 on the upper surface of the upper endplate 110 are provided over three major areas, a first area 113a near a first edge of the upper endplate 110, a second area 113b near the center of the upper endplate 110, and a third area near a second edge of the endplate 113c.

Turning to FIG. 54, in an optional embodiment, the anchoring fins 111 are selectively retractable and extendable by providing a deployment mechanism 160 that is associated with the upper endplate 110. A similar mechanism may be used on the lower endplate 120. The deployment mechanism includes a slider 161 that slides within a channel 162 formed in the upper endplate 110. The channel 162 includes a threaded region 163, and the slider 161 includes matching threads 164, thereby providing a mechanism for advancing the slider 161 within the channel 162. As the slider 161 is advanced within the channel 162, a tapered region 165 engages the bottom surface of a deployable fin 166. Further advancement of the slider 161 causes the deployable fin 166 to be raised upward within a slot 167 on the upper surface of the upper endplate 110. Reversing the deployment mechanism 160 causes the fin 166 to retract. The deployment mechanism 160 may also be used in conjunction with spikes, serrations, or other anchoring devices. In an alternative embodiment, the threaded slider 161 of the deployment mechanism may be replaced with a dowel pin that is advanced to deploy the fin 166. Other advancement mechanisms are also possible.

Returning to FIG. 18, the upper endplate 210 contains a plurality of slots 214 through which the fibers 240 may be passed through or wound, as shown. The actual number of slots 214 contained on the endplate is variable. Increasing the number of slots will result in an increase in the circumferential density of the fibers holding the endplates together. Additionally, the fibers may be wound multiple times within the same slot, thereby increasing the radial density of the fibers. In each case, this improves the wear resistance and increases the torsional and flexural stiffness of the prosthetic disc, thereby further approximating natural disc stiffness. In addition, the fibers 240 may be passed through or wound on each slot, or only on selected slots, as needed.

As described above, the purpose of the fibers 240 is to hold the upper endplate 210 and lower endplate 220 together and to limit the range-of-motion to mimic the range-of-motion of a natural disc. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 240 are generally elongate fibers having a diameter that ranges from about 100 µm to about 500 µm, and preferably about 200 µm to about 400 µm. Optionally, the fibers may be injection molded with an elastomer to encapsulate the fibers, thereby providing protection from tissue ingrowth and improving torsional and flexural stiffness.

The fibers 240 may be fabricated from any suitable material. Examples of suitable materials include polyester (e.g., Dacron®), polyethylene, polyaramid, poly-paraphenylene terephthalamide (e.g., Kevlar®), carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers 240 may be terminated on an endplate by tying a knot in the fiber on the superior surface of an endplate. Alternatively, the fibers 240 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

The core member 230 is intended to provide support to and to maintain the relative spacing between the upper endplate 210 and inner lower endplate 220a. The core member 230 is made of a relatively compliant material, for example, polyurethane or silicone, and is typically fabricated by injection molding. A preferred construction for the core member 230 includes a nucleus formed of a hydrogel and an elastomer reinforced fiber annulus. For example, the nucleus, the central portion of the core member 230, may comprise a hydrogel material such as a water-absorbing polyurethane (e.g. Tecophilic,) polyvinyl alcohol (PVA), polyethylene oxide (PEO), polyvinylpyrrolidone (PVP), polyacrylamide, silicone, or PEO based polyurethane. The annulus may comprise an elastomer, such as silicone, polyurethane or polyester (e.g., Hytrel®), reinforced with a fiber, such as polyethylene, polyethylene terephthalate, or poly-paraphenylene terephthalamide (e.g., Kevlar®).

The shape of the core member 230 is typically generally cylindrical or bean-shaped, although the shape (as well as the materials making up the core member and the core member size) may be varied to obtain desired physical or performance properties. For example, the core member 230 shape, size, and materials will directly affect the degree of flexion, extension, lateral bending, and axial rotation of the prosthetic disc.

The annular capsule 250 is preferably made of polyurethane or silicone and may be fabricated by injection molding, two-part component mixing, or dipping the endplate-core-fiber assembly into a polymer solution. Alternatively, an outer ring or gasket (not shown in the drawings) may optionally be provided in place of the annular capsule 250.

The upper subassembly 205 is configured to be selectively attached to the outer lower endplate 220b. As shown, for example, in FIGS. 3 and 6, the edges 225 of the inner lower endplate 220a have a size and shape adapted to engage slots 226 formed on the upper surface of the outer lower endplate 220b. Accordingly, the upper subassembly 205 will slide onto the outer lower endplate 220b, with the inner lower endplate edges 225 engaging the outer lower endplate slots 226.

At this point, the differences between the constrained, semi-constrained and unconstrained embodiments of the two-piece prosthetic disc will be described. Turning first to the constrained embodiment shown in FIGS. 16-18, once the upper subassembly 205 is fully advanced onto the outer lower endplate 220b—i.e., once the leading edge 225 of the inner lower endplate 220a engages the back portion of the slot 226 of the outer lower endplate 220b—a tab 261 on the bottom surface of the inner lower endplate 220a engages a notch 262 on the top surface of the outer lower endplate 220b (see FIG. 18), thereby locking the upper subassembly 205 to the outer lower endplate 220b. The tab 261 and notch 262 are squared surfaces, thereby preventing relative rotation between the inner lower endplate 220a and outer lower endplate 220b. Additionally, the edges 225 of the inner lower endplate 220a and the mating slots 226 of the outer lower endplate 220b include mating straight portions 227 and 228, respectively, which also tend to inhibit rotation of the inner lower endplate 220a relative to the outer lower endplate 220b.

Figure 19:
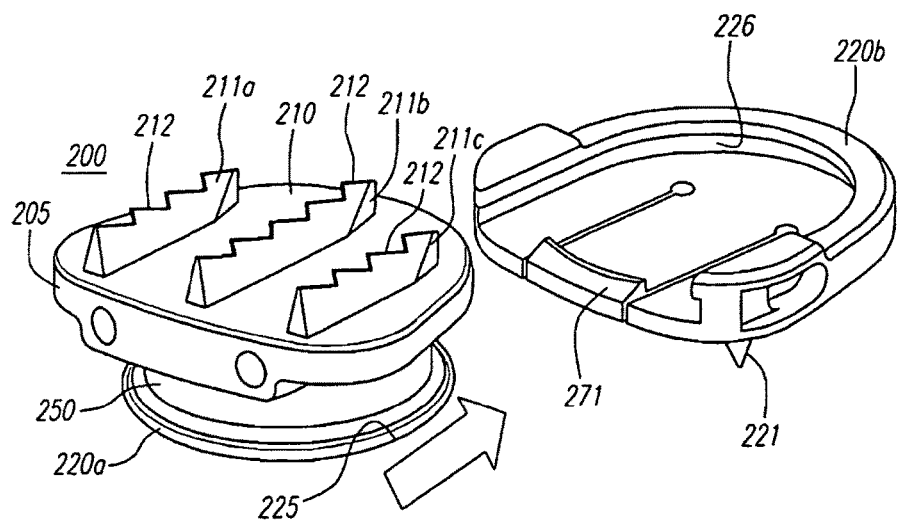
FIG. 19 provides a three-dimensional view of a prosthetic disc having a two-piece unconstrained structure.
Figure 20:
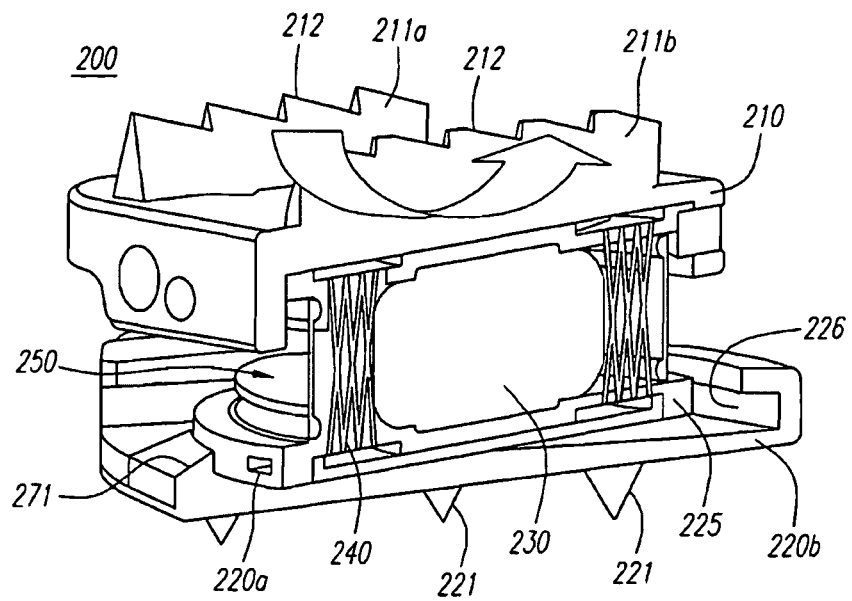
FIG. 20 provides a cross-sectional view of a prosthetic disc having a two-piece unconstrained structure.

Turning next to the unconstrained embodiment shown in FIGS. 19-20, the outer lower endplate 220b is provided with a raised lip 271. The raised lip 271 is slightly downwardly displaceable, i.e., the raised lip 271 will deflect downwardly when force is applied to it. Accordingly, when the upper subassembly is being attached to the outer lower endplate 220b, the raised lip will displace downwardly to allow the edges 225 of the inner lower endplate 220a to engage the slots 226 of the outer lower endplate 220b. Once the upper subassembly 205 is fully advanced onto the outer lower endplate 220b—i.e., once the leading edge 225 of the inner lower endplate 220a engages the back portion of the slot 226 of the outer lower endplate 220b—the raised lip 271 snaps back into place, as shown in FIG. 20, thereby locking the upper subassembly 205 to the outer lower endplate 220b. Notably, the raised lip 271 and inner lower endplate 220a include rounded surfaces, thereby allowing relative rotation between the inner lower endplate 220a and outer lower endplate 220b. Additionally, the edges 225 of the inner lower endplate 220a and the mating slots 226 of the outer lower endplate 220b do not include the mating straight portions 227, 228 of the constrained embodiment. Thus, in the unconstrained embodiment of the two-piece prosthetic disc, as shown in FIGS. 19 and 20, the upper subassembly 205 is capable of substantially free rotation relative to the outer lower endplate 220b.

The two-piece structure embodiment of the prosthetic disc is implanted by a surgical procedure. After removing the natural disc, the outer lower endplate 220b is placed onto and anchored into the inferior vertebral body within the void between the two adjacent vertebral bodies previously occupied by the natural disc. Next, grooves are formed in the superior vertebral body. The upper subassembly 205 of the prosthetic disc is then inserted into the void, while aligning the anchoring fins 211 with the grooves formed on the superior vertebral body, and while sliding the inner lower endplate 220a into the outer lower endplate 220b in a manner that the edges 225 of the inner endplate 220a engage the slots 226 of the outer endplate 220b. The anchoring fins cause the prosthetic disc to be secured in place between the adjacent vertebral bodies.

The two-piece prosthetic disc has several advantages over prior art artificial discs, as well as over alternative treatment procedures such as spinal fusion. For example, the two-piece prosthetic discs described herein provide compressive compliance similar to that of a natural spinal disc. In addition, the motions in flexion, extension, lateral bending, and axial rotation are also restricted in a manner near or identical to those associated with a natural disc.

C. Three-Piece Structure

Figure 21:
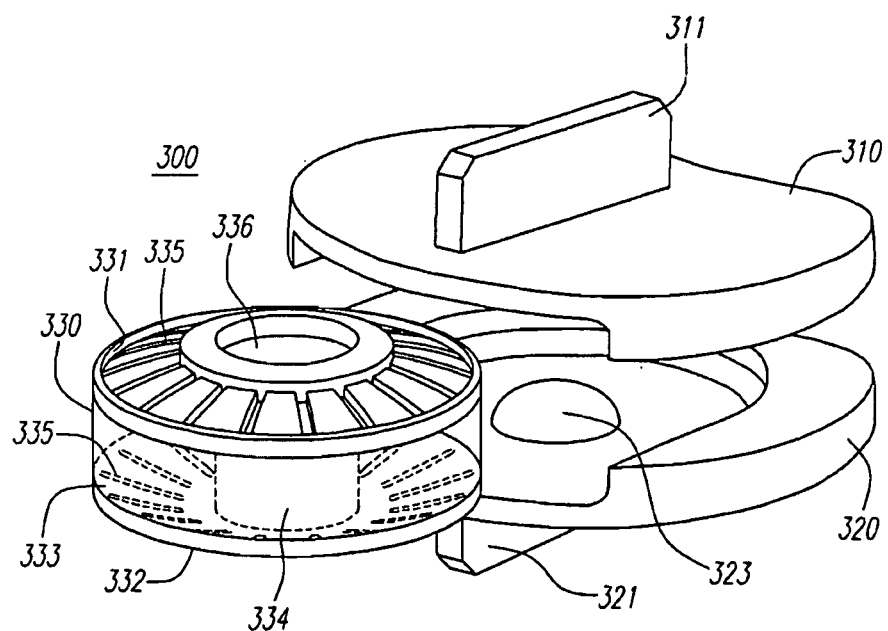
FIG. 21 provides a three-dimensional view of a prosthetic disc having a three-piece structure.
Figure 22:
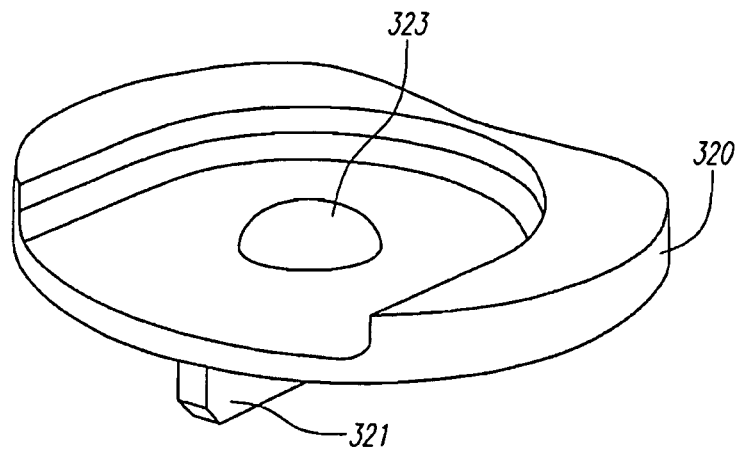
FIG. 22 provides a three-dimensional view of a lower endplate of the prosthetic disc shown in FIG. 21.
Figure 23:
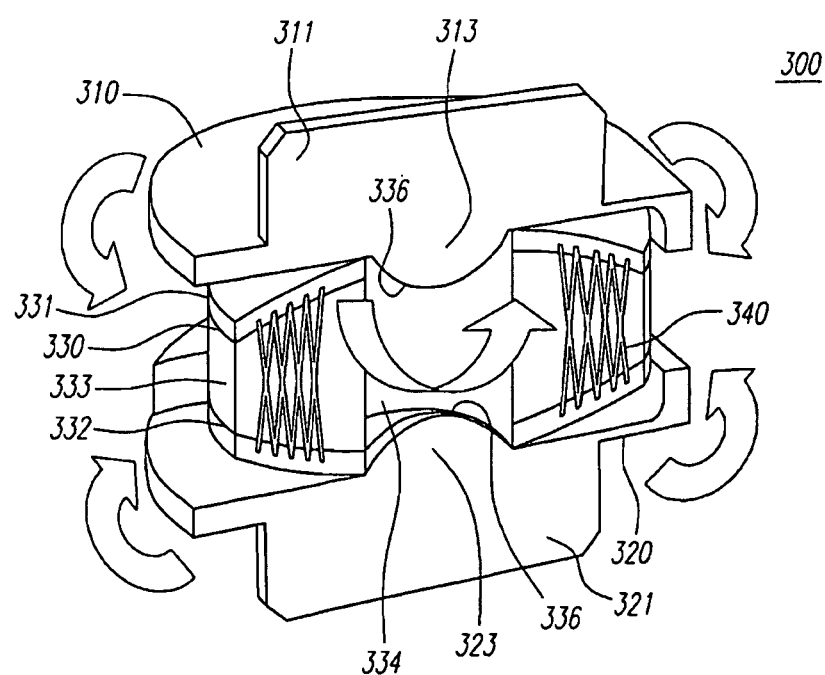
FIG. 23 provides a cross-sectional view of a prosthetic disc having a three-piece structure.

A representative prosthetic intervertebral disc 300 having a three-piece structure is shown in FIGS. 21 through 23. The prosthetic disc includes an upper endplate 310, a lower endplate 320, and a core assembly 330 retained between the upper endplate 310 and the lower endplate 320.

The upper endplate 310 and lower endplate 320 are generally flat, planar members, and are fabricated from a physiologically acceptable material that provides substantial rigidity. Examples of materials suitable for use in fabricating the upper endplate 310 and lower endplate 320 include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. Optionally, the endplates may be coated with hydroxylapatite, titanium plasma spray, or other coatings to enhance bony ingrowth.

As noted above, the upper and lower endplates typically have a length of from about 12 mm to about 45 mm, preferably from about 13 mm to about 44 mm, a width of from about 11 mm to about 28 mm, preferably from about 12 mm to about 25 mm, and a thickness of from about 0.5 mm to about 4 mm, preferably from about 1 mm to about 3 mm. The sizes of the upper and lower endplates are selected primarily based upon the size of the void between adjacent vertebral bodies to be occupied by the prosthetic disc. Accordingly, while endplate lengths and widths outside of the ranges listed above are possible, they are not typical. The upper surface of the upper endplate 310 and the lower surface of the lower endplate 320 are preferably each provided with a mechanism for securing the endplate to the respective opposed surfaces of the upper and lower vertebral bodies between which the prosthetic disc is to be implanted. For example, in FIGS. 21 and 23, the upper endplate 310 includes an anchoring fin 311. The anchoring fin 311 is intended to engage a mating groove that is formed on the surface of the upper vertebral body to thereby secure the endplate to the vertebral body. The anchoring fin 311 extends generally perpendicularly from the generally planar external surface of the upper endplate 310, i.e., upward from the upper side of the endplate as shown in FIGS. 21 and 23. As shown in the Figures, the anchoring fin 311 is disposed at the center of external surface of the upper endplate 310 and has a length that is slightly shorter than the width of the upper endplate 310. Although not shown in the Figures, the anchoring fin 311 may be provided with a plurality of serrations located on the top edge of the anchoring fin. The serrations are intended to enhance the ability of the anchoring fin to engage the vertebral body and to thereby secure the upper endplate 310 to the spine.

Similarly, the lower surface of the lower endplate 320 includes an anchoring fin 321. The anchoring fin 321 on the lower surface of the lower endplate 320 is identical in structure and function to the anchoring fin 311 on the upper surface of the upper endplate 310, with the exception of its location on the prosthetic disc. The anchoring fin 321 on the lower endplate 320 is intended to engage a mating groove formed on the lower vertebral body, whereas the anchoring fin 311 on the upper endplate 310 is intended to engage a mating groove on the upper vertebral body. Thus, the prosthetic disc 300 is held in place between the adjacent vertebral bodies.

Alternatively, the upper endplate 310 and lower endplate 320 of the three-piece prosthetic disc may employ one of the alternative securing mechanisms shown in FIGS. 13A-C. As described above in relation to the one-piece prosthetic device shown in FIG. 13A, each of the upper endplate 110 and lower endplate 120 is provided with a single anchoring fin 111, 121. The anchoring fins 111, 121 are located along a center line of the respective endplates, and each is provided with a plurality of serrations 112, 122 on its upper edge. The single anchoring fins 111, 121 are intended to engage grooves formed on the opposed surface of the upper and lower vertebral bodies, as described above. In FIG. 13B, each of the upper endplate 110 and lower endplate 120 is provided with three anchoring fins 111a-c, 121a-c. The FIG. 13B prosthetic disc is the same as the prosthetic disc shown in FIG. 12, but it is shown in perspective rather than cross-section. Thus, the structure and function of the anchoring fins 111a-c and 121a-c are as described above in relation to FIG. 12. Finally, in FIG. 13C, each of the upper endplate 110 and lower endplate 120 is provided with a plurality of serrations 113, 123 over a portion of the exposed external surface of the respective endplate. The serrations 113, 123 are intended to engage the opposed surfaces of the adjacent vertebral bodies to thereby secure the endplates in place between the vertebral bodies. The serrations 113, 123 may be provided over the entire external surface of each of the upper and lower endplates, or they may be provided over only a portion of those surfaces. For example, in FIG. 13C, the serrations 113 on the upper surface of the upper endplate 110 are provided over three major areas, a first area 113a near a first edge of the upper endplate 110, a second area 113b near the center of the upper endplate 110, and a third area near a second edge of the endplate 113c.

Turning to FIG. 54, in an optional embodiment, the anchoring fins 111 are selectively retractable and extendable by providing a deployment mechanism 160 that is associated with the upper endplate 110. A similar mechanism may be used on the lower endplate 120. The deployment mechanism includes a slider 161 that slides within a channel 162 formed in the upper endplate 110. The channel 162 includes a threaded region 163, and the slider 161 includes matching threads 164, thereby providing a mechanism for advancing the slider 161 within the channel 162. As the slider 161 is advanced within the channel 162, a tapered region 165 engages the bottom surface of a deployable fin 166. Further advancement of the slider 161 causes the deployable fin 166 to be raised upward within a slot 167 on the upper surface of the upper endplate 110. Reversing the deployment mechanism 160 causes the fin 166 to retract. The deployment mechanism 160 may also be used in conjunction with spikes, serrations, or other anchoring devices. In an alternative embodiment, the threaded slider 161 of the deployment mechanism may be replaced with a dowel pin that is advanced to deploy the fin 166. Other advancement mechanisms are also possible.

The core assembly 330 is intended to provide support to and to maintain the relative spacing between the upper endplate 310 and lower endplate 320. The core assembly 330 provides compressive compliance to the three-piece prosthetic disc, as well as providing limited translation, flexion, extension, and lateral bending by and between the upper endplate 310 and lower endplate 320. The core assembly 330 further provides substantially unlimited rotation by and between the upper endplate 310 and the lower endplate 320.

The core assembly 330 includes a top cap 331, a bottom cap 332, a sidewall 333, and a core center 334 held by and retained between the top cap 331, bottom cap 332, and sidewall 333. The top cap 331 and bottom cap 332 are generally planar, and are fabricated from a physiologically acceptable material that provides substantial rigidity. Examples of materials suitable for use in fabricating the top cap 331 and bottom cap 332 include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. The core center 334 is made of a relatively compliant material, for example, polyurethane or silicone, and is typically fabricated by injection molding. The shape of the core center 334 is typically generally cylindrical or bean-shaped, although the shape (as well as the materials making up the core center and the core member size) may be varied to obtain desired physical or performance properties. For example, the core member 334 shape, size, and materials will directly affect the degree of flexion, extension, lateral bending, and axial rotation of the prosthetic disc.

The top cap 331 and bottom cap 332 each preferably includes a generally concave indentation 336 formed at a center point of the cap. The indentations 336 are intended to cooperate with a pair of retainers formed on the internal surfaces of the endplates to retain the core assembly 330 in place between the retainers, as described more fully below.

The top cap 331 and bottom cap 332 preferably contain a plurality of slots 335 spaced radially about the surface of each of the caps. One or more fibers 340 are wound around the top cap 331 and bottom cap 332 through the slots 335 to attach the endplates to one another. The fibers 340 preferably are not tightly wound, thereby allowing a degree of axial rotation, bending, flexion, and extension by and between the top cap 331 and bottom cap 332. The core center 334 is preferably pre-compressed. The actual number of slots 335 contained on each of the top cap 331 and bottom cap 332 is variable. Increasing the number of slots will result in an increase in the circumferential density of the fibers holding the endplates together. Additionally, the fibers may be wound multiple times within the same slot, thereby increasing the radial density of the fibers. In each case, this improves the wear resistance and increases the torsional and flexural stiffness of the prosthetic disc, thereby further approximating natural disc stiffness. In addition, the fibers 340 may be passed through or wound on each slot, or only on selected slots, as needed.

The purpose of the fibers 340 is to hold the top cap 331 and bottom cap 332 together and to limit the range-of-motion to mimic the range-of-motion of a natural disc. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 140 are generally elongate fibers having a diameter that ranges from about 100 µm to about 500 µm, and preferably about 200 µm to about 400 µm. Optionally, the fibers may be injection molded with an elastomer to encapsulate the fibers, thereby providing protection from tissue ingrowth and improving torsional and flexural stiffness.

The fibers 340 may be fabricated from any suitable material. Examples of suitable materials include polyester (e.g., Dacron®), polyethylene, polyaramid, poly-paraphenylene terephthalamide (e.g., Kevlar®), carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers 340 may be terminated on an endplate by tying a knot in the fiber on the superior surface of an endplate. Alternatively, the fibers 340 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

The sidewall 333 is preferably made of polyurethane or silicone and may be fabricated by injection molding, two-part component mixing, or dipping the core assembly into a polymer solution. Alternatively, an outer ring or gasket (not shown in the drawings) may optionally be provided in place of the sidewall 333.

As noted above, the core assembly 330 is selectively retained between the upper endplate 310 and the lower endplate 320. A preferred mechanism for retaining the core assembly 330 between the two endplates is illustrated in FIGS. 21 through 23. For example, the upper endplate 310 is provided with a retainer 313 formed on the interior surface of the upper endplate 310. The retainer 313 is a convex body formed at the center of the internal surface of the upper endplate 310 that extends into the space between the upper endplate 310 and lower endplate 320 when the endplates are implanted into the patient. A similar retainer 323 is formed on the opposed internal surface of the lower endplate 320. Each of the retainers 313, 323 is preferably of generally semi-spherical shape, and each is preferably formed from the same material used to fabricate the upper and lower endplates 310, 320.

As shown, for example, in FIG. 23, the retainers 313, 323 formed on the internal surfaces of the endplates cooperate with the indentations 336 formed on the external surfaces of the top cap 331 and bottom 332 of the core assembly 330 to hold the core assembly in place between the endplates. The amount of retaining force holding the core assembly 330 in place will depend on several factors, including the materials used to form the endplates and the core assembly, the size and shape of the core assembly, the distance separating the two endplates, the size and shape of each of the retainers and indentations, and other factors. Any one or all of these factors may be varied to obtain desired results. Typically, the retaining force will be sufficient to hold the core assembly in place, while still allowing each of the endplates to rotate substantially freely relative to the core assembly.

Figure 24A:
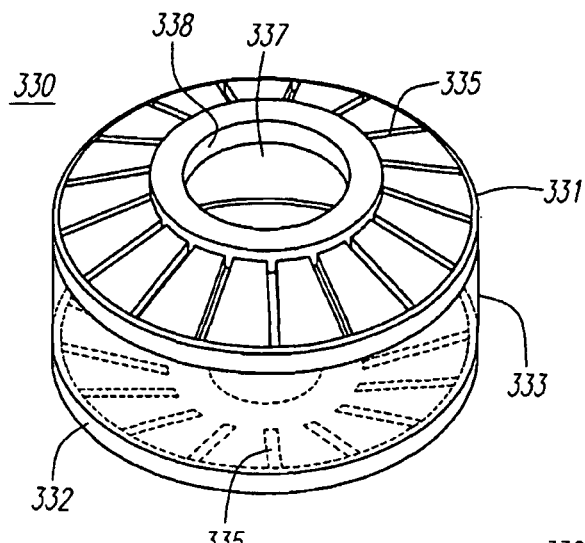
FIG. 24A provides a three-dimensional view of a core assembly for a prosthetic disc having a three-piece structure.
Figure 24B:
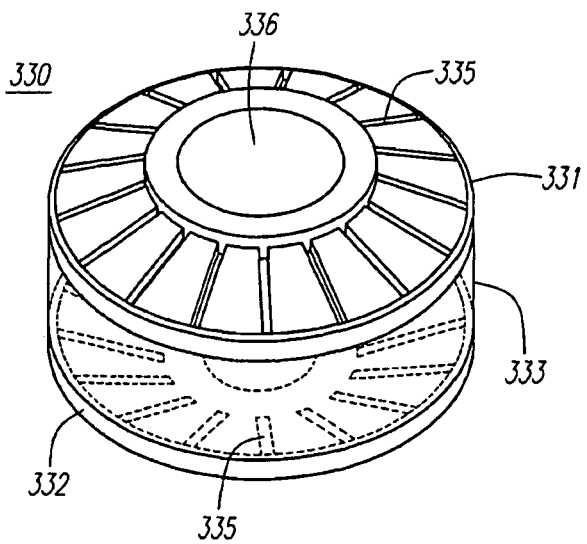
FIG. 24B provides a three-dimensional view of another core assembly for a prosthetic disc having a three-piece structure.
Figure 24C:
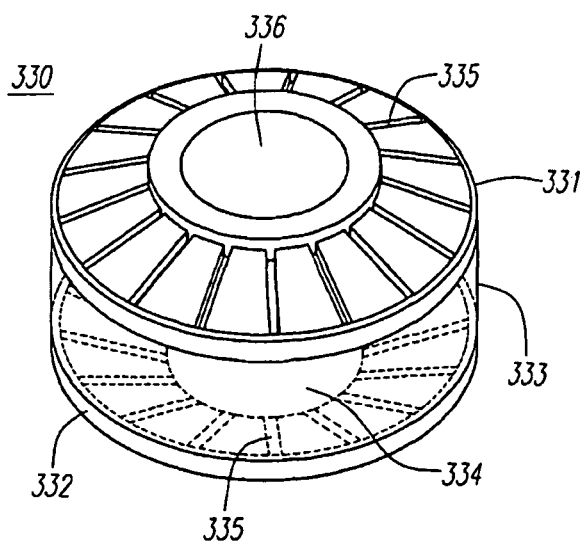
FIG. 24C provides a three-dimensional view of another core assembly for a prosthetic disc having a three-piece structure.

Turning to FIGS. 24A-C, three embodiments of the core assembly 330 are illustrated. In a first embodiment, shown in FIG. 24A, the core assembly 330 is provided with a through hole 337, i.e., the central portion of the core assembly 330 is hollow. In this embodiment, although there are no indentations 336, the through hole 337 creates a shoulder 338 on each of the top cap 331 and bottom cap 332. The shoulders 338 have a size selected to suitably engage the retainers 313, 323 formed on the endplates. In a second embodiment, the core assembly 330 is provided with indentations 336 and the core center 334 extends throughout the internal volume of the core assembly. Finally, in a third embodiment, the core assembly 330 is provided with indentations 336, but the core center 334 occupies only a central portion of the internal volume of the core assembly 330.

Figure 25A:
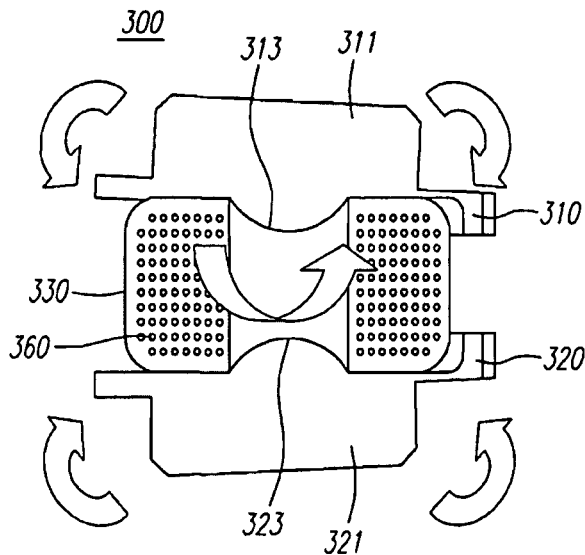
FIG. 25A provides a cross-section view of a fiber reinforced core assembly.
Figure 25B:
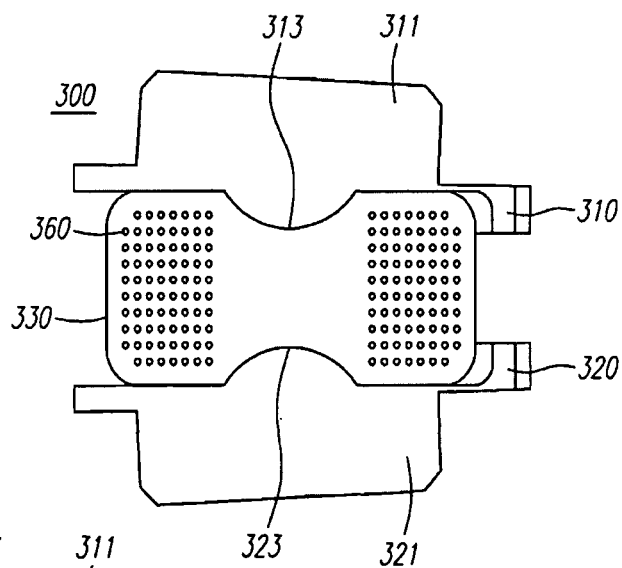
FIG. 25B provides a cross-section view of another fiber reinforced core assembly.
Figure 25C:
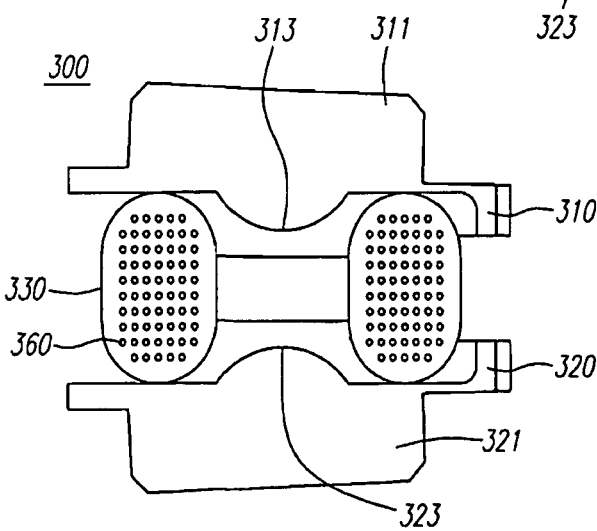
FIG. 25C provides a cross-section view of another fiber reinforced core assembly.

Turning to FIGS. 25A-C, the core assembly may optionally include a plurality of reinforcing fibers 360 distributed throughout the body of the core assembly. The fibers 360 may be fabricated from any suitable material. Examples of suitable materials include polyester (e.g., Dacron), polyethylene, polyaramid, carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like. The reinforcing fibers 360 provide additional strength to the core assembly. The fiber reinforcement is made by injecting core center material around the fibers formed in the shape of the core center. Exemplary core shapes are shown in FIGS. 25A-C, and include a core assembly 330 having a through hole 337 (FIG. 25A), a core assembly 330 having indentations 336 on each of the top and bottom surfaces (FIG. 25B), and a core assembly 330 having a toroidal shape (FIG. 25C).

The fibers 360 may be terminated on an endplate by tying a knot in the fiber on the superior surface of an endplate. Alternatively, the fibers 360 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

Figure 26:
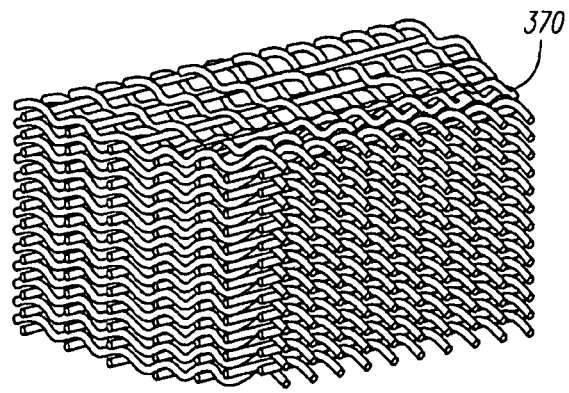
FIG. 26 provides a three-dimensional view of a stacked fabric core assembly.
Figure 27:
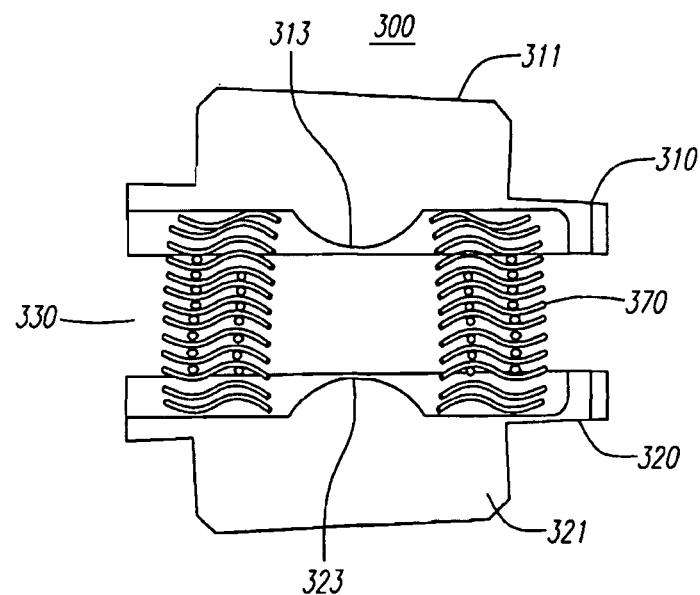
FIG. 27 provides a cross-sectional view of a stacked fabric core assembly.
Figure 28A:
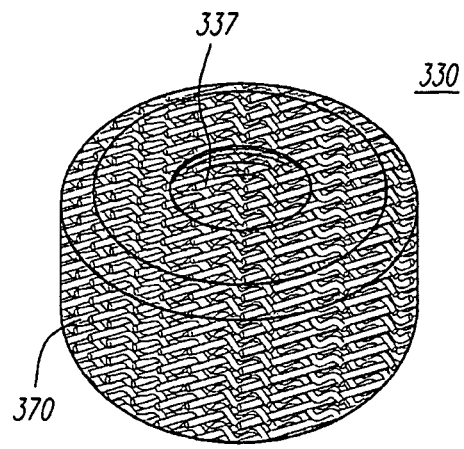
FIG. 28A provides a three-dimensional view of a stacked fabric core assembly.
Figure 28B:
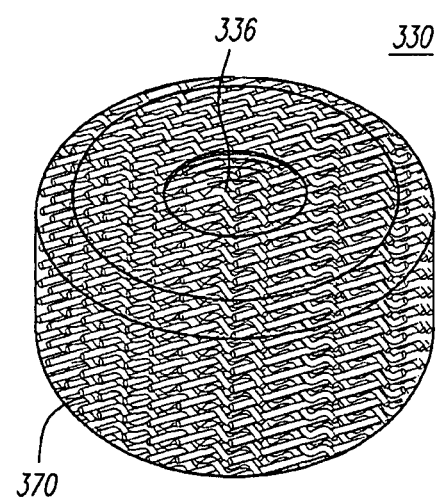
FIG. 28B provides a three-dimensional view of another stacked fabric core assembly.
Figure 28C:
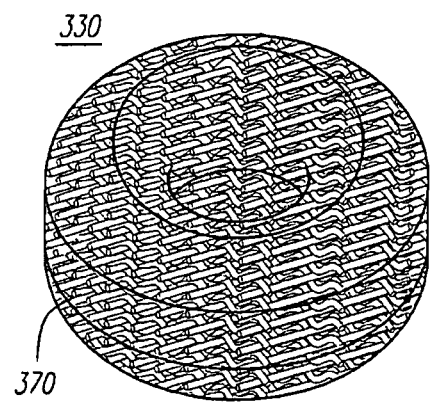
FIG. 28C provides a three-dimensional view of another stacked fabric core assembly.

Turning next to FIGS. 26, 27, and 28A-C, the core assembly may optionally be formed of stacks of reinforcing fabric having no silicone, polyurethane, or other polymeric component. As shown in FIG. 26, woven fibers 370 are formed into sheets of fabric that are compressed into a stack to form a core body. The woven fibers 370 may be formed of materials such as polyester (e.g., Dacron), polyethylene, polyaramid, carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like. FIG. 27 is a cross-sectional view of a woven fiber core body. FIG. 28A illustrates a woven fiber core body 330 having a through hole 337 similar to the structure described previously. Similarly, FIG. 28B illustrates a woven fiber core body 330 having indentations 336 on its upper and lower surfaces. Finally, FIG. 28C illustrates a woven fiber core body 330 having a toroidal shape.

The three-piece structure embodiment of the prosthetic disc is implanted by a surgical procedure. After removing the natural disc, grooves are formed in the superior and inferior vertebrae between which the prosthetic disc is to be implanted. The upper endplate 310 and lower endplate 320 are then each implanted into the void, while aligning the anchoring fins 311 321 with the grooves formed on the vertebral bodies. The anchoring fins cause the prosthetic disc to be secured in place between the adjacent vertebral bodies. After the upper endplate 310 and lower endplate 320 are implanted, the core assembly 330 is engaged between the endplates to complete the implantation.

The three-piece prosthetic disc has several advantages over prior art artificial discs, as well as over alternative treatment procedures such as spinal fusion. For example, the prosthetic discs described herein provide compressive compliance similar to that of a natural spinal disc. In addition, the motions in flexion, extension, lateral bending, and axial rotation are also restricted in a manner near or identical to those associated with a natural disc.

D. Four-Piece Structure

Representative prosthetic intervertebral discs 400 having four-piece structures are shown in FIGS. 29 through 35. The prosthetic discs include an upper endplate 410, a lower endplate 420, and a two-piece core assembly 430 retained between the upper endplate 410 and the lower endplate 420.

The upper endplate 410 and lower endplate 420 are generally flat, planar members, and are fabricated from a physiologically acceptable material that provides substantial rigidity. Examples of materials suitable for use in fabricating the upper endplate 410 and lower endplate 420 include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. Optionally, the endplates may be coated with hydroxylapatite, titanium plasma spray, or other coatings to enhance bony ingrowth.

Figure 30:
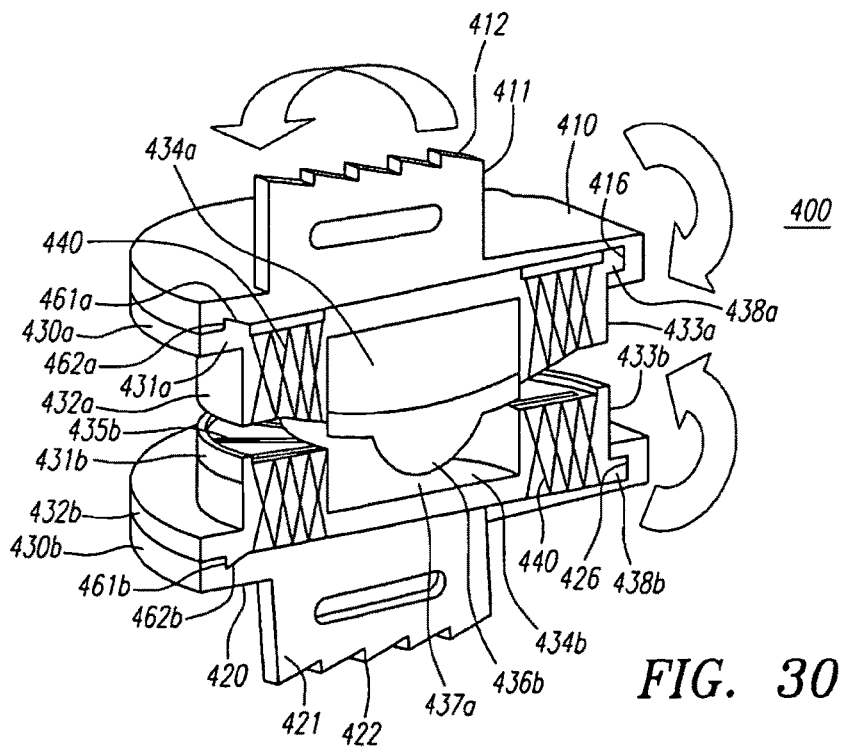
FIG. 30 provides a cross-sectional view of a prosthetic disc having a four-piece structure.
Figure 31:
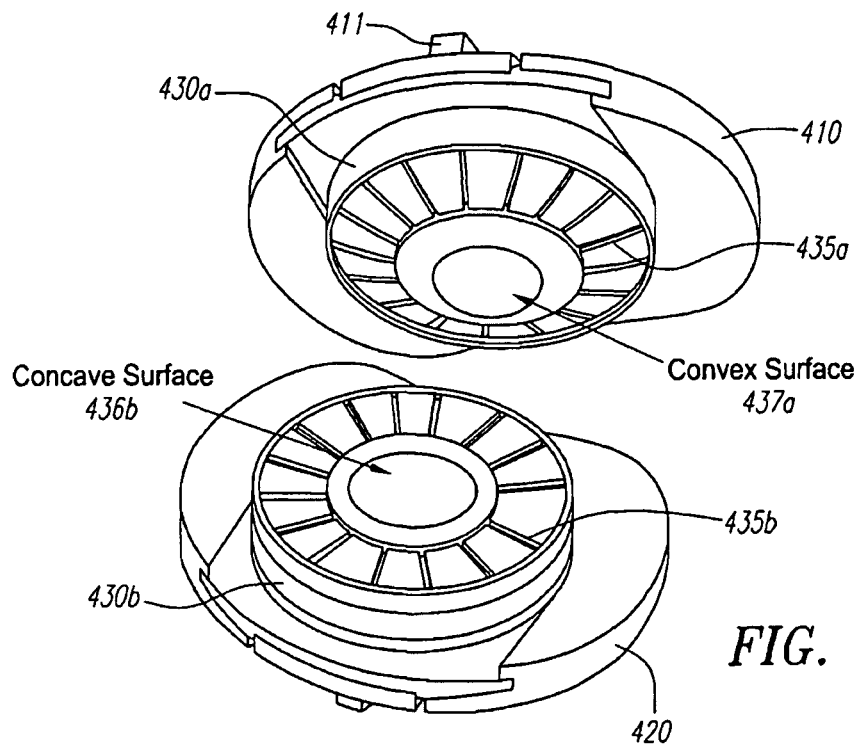
FIG. 31 provides an expanded view of a core assembly for a prosthetic disc having a four-piece structure.
Figure 32:
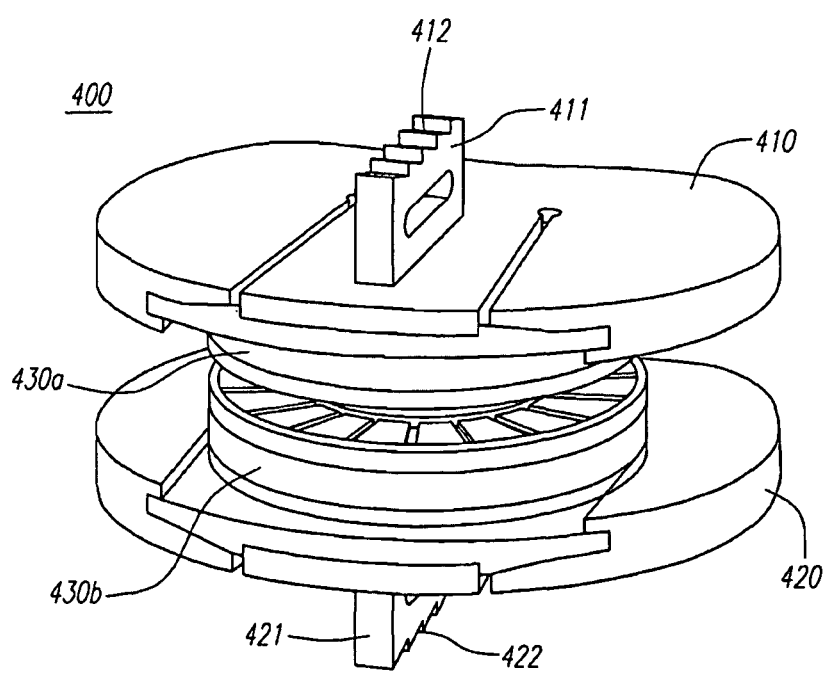
FIG. 32 provides a three-dimensional view of a prosthetic disc having a four-piece structure.

As noted above, the upper and lower endplates typically have a length of from about 12 mm to about 45 mm, preferably from about 13 mm to about 44 mm, a width of from about 11 mm to about 28 mm, preferably from about 12 mm to about 25 mm, and a thickness of from about 0.5 mm to about 4 mm, preferably from about 1 mm to about 3 mm. The sizes of the upper and lower endplates are selected primarily based upon the size of the void between adjacent vertebral bodies to be occupied by the prosthetic disc. Accordingly, while endplate lengths and widths outside of the ranges listed above are possible, they are not typical The upper surface of the upper endplate 410 and the lower surface of the lower endplate 420 are preferably each provided with a mechanism for securing the endplate to the respective opposed surfaces of the upper and lower vertebral bodies between which the prosthetic disc is to be implanted. For example, as shown in FIGS. 30 and 32, the upper endplate 410 includes an anchoring fin 411. The anchoring fin 411 is intended to engage a mating groove that is formed on the surface of the upper vertebral body to thereby secure the endplate to the vertebral body. The anchoring fin 411 extends generally perpendicularly from the generally planar external surface of the upper endplate 410, i.e., upward from the upper side of the endplate as shown in FIGS. 30 and 32. As shown in the Figures, the anchoring fin 411 is disposed at the center of external surface of the upper endplate 410 and has a length that is slightly less than the width of the upper endplate 410. Although not shown in the Figures, the anchoring fin 411 may be provided with a plurality of serrations located on its top edge. The serrations are intended to enhance the ability of the anchoring fin to engage the vertebral body and to thereby secure the upper endplate 410 to the spine.

Similarly, the lower surface of the lower endplate 420 includes an anchoring fin 421. The anchoring fin 421 on the lower surface of the lower endplate 420 is identical in structure and function to the anchoring fin 411 on the upper surface of the upper endplate 410, with the exception of its location on the prosthetic disc. The anchoring fin 421 on the lower endplate 420 is intended to engage a mating groove formed on the lower vertebral body, whereas the anchoring fin 411 on the upper endplate 410 is intended to engage a mating groove on the upper vertebral body. Thus, the prosthetic disc 400 is held in place between the adjacent vertebral bodies.

Alternatively, the upper endplate 410 and lower endplate 420 of the three-piece prosthetic disc may employ one of the alternative securing mechanisms shown in FIGS. 13A-C. As described above in relation to the one-piece prosthetic device shown in FIG. 13A, each of the upper endplate 110 and lower endplate 120 is provided with a single anchoring fin 111, 121. The anchoring fins 111, 121 are located along a centerline of the respective endplates, and each is provided with a plurality of serrations 112, 122 on its upper edge. The single anchoring fins 111, 121 are intended to engage grooves formed on the opposed surface of the upper and lower vertebral bodies, as described above. In FIG. 13B, each of the upper endplate 110 and lower endplate 120 is provided with three anchoring fins 111*a-c*, 121*a-c*. The FIG. 13B prosthetic disc is the same as the prosthetic disc shown in FIG. 12, but it is shown in perspective rather than cross-section. Thus, the structure and function of the anchoring fins 111*a-c* and 121*a-c* are as described above in relation to FIG. 12. Finally, in FIG. 13C, each of the upper endplate 110 and lower endplate 120 is provided with a plurality of serrations 113, 123 over a portion of the exposed external surface of the respective endplate. The serrations 113, 123 are intended to engage the opposed surfaces of the adjacent vertebral bodies to thereby secure the endplates in place between the vertebral bodies. The serrations 113, 123 may be provided over the entire external surface of each of the upper and lower endplates, or they may be provided over only a portion of those surfaces. For example, in FIG. 13C, the serrations 113 on the upper surface of the upper endplate 110 are provided over three major areas, a first area 113*a* near a first edge of the upper endplate 110, a second area 113*b* near the center of the upper endplate 110, and a third area near a second edge of the endplate 113*c*.

Turning to FIG. 54, in an optional embodiment, the anchoring fins 111 are selectively retractable and extendable by providing a deployment mechanism 160 that is associated with the upper endplate 110. A similar mechanism may be used on the lower endplate 120. The deployment mechanism includes a slider 161 that slides within a channel 162 formed in the upper endplate 110. The channel 162 includes a threaded region 163, and the slider 161 includes matching threads 164, thereby providing a mechanism for advancing the slider 161 within the channel 162. As the slider 161 is advanced within the channel 162, a tapered region 165 engages the bottom surface of a deployable fin 166. Further advancement of the slider 161 causes the deployable fin 166 to be raised upward within a slot 167 on the upper surface of the upper endplate 110. Reversing the deployment mechanism 160 causes the fin 166 to retract. The deployment mechanism 160 may also be used in conjunction with spikes, serrations, or other anchoring devices. In an alternative embodiment, the threaded slider 161 of the deployment mechanism may be replaced with a dowel pin that is advanced to deploy the fin 166. Other advancement mechanisms are also possible.

Figure 29:
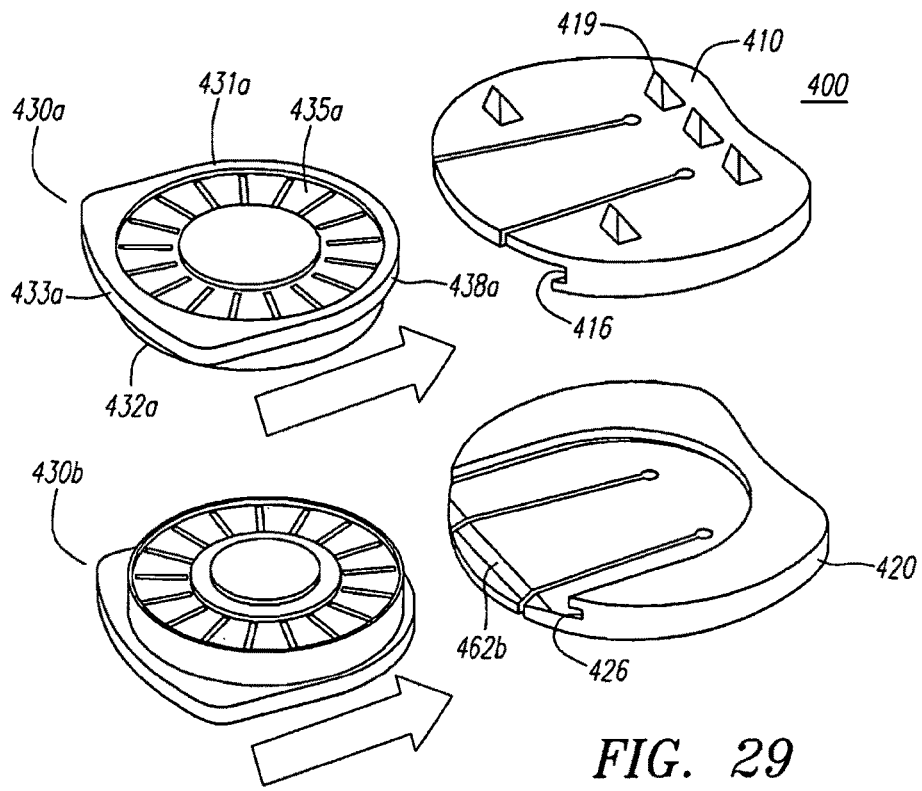
FIG. 29 provides a three-dimensional view of a prosthetic disc having a four-piece structure.

FIG. 29 illustrates yet another alternative mechanism for securing the upper and lower endplates to the vertebral bodies. As shown in the Figure, the upper endplate 410 may be provided with a plurality of anchoring spikes 419 spaced over the external surface of the endplate. The anchoring spikes 419 are adapted to engage the internal surface of the vertebral body. Although not shown in FIG. 29, the external surface of the lower endplate 420 may optionally be provided with similar anchoring spikes to secure the lower endplate to the internal surface of the inferior vertebral body.

The core assembly 430 is intended to provide support to and to maintain the relative spacing between the upper endplate 410 and lower endplate 420. The core assembly 430 provides compressive compliance to the four-piece prosthetic disc, as well as providing limited translation, flexion, extension, and lateral bending by and between the upper endplate 410 and lower endplate 420. The core assembly 430 further provides substantially unlimited rotation by and between the upper endplate 410 and the lower endplate 420.

The core assembly 430 includes an upper core member 430*a* and a lower core member 430*b*, 430*c*. Two embodiments of the core assembly 430 of the four-piece prosthetic disc are shown in FIGS. 29 through 35. In the first embodiment, shown in FIGS. 29 through 32, both the upper core member 430*a* and the lower core member 430*b* include a core structure having top and bottom caps, slots, fibers, a core center, and an annular capsule. In the second embodiment, shown in FIGS. 33 through 35, the upper core member 430*a* is identical to that of the first embodiment, but the lower core member 430*c* is, instead, a solid structure. These structures are described more fully below.

The upper core member 430*a* includes a top cap 431*a*, a bottom cap 432*a*, a sidewall 433*a*, and a core center 434*a* held by and retained between the top cap 431*a*, bottom cap 432*a*, and sidewall 433*a*. The top cap 431*a* and bottom cap 432*a* are generally planar, and are fabricated from a physiologically acceptable material that provides substantial rigidity. Examples of materials suitable for use in fabricating the top cap 431*a* and bottom cap 432*a* include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. The core center 434*a* is made of a relatively compliant material, for example, polyurethane or silicone, and is typically fabricated by injection molding. The shape of the core center 434*a* is typically generally cylindrical or bean-shaped, although the shape (as well as the materials making up the core center and the core member size) may be varied to obtain desired physical or performance properties. For example, the core member 434*a* shape, size, and materials will directly affect the degree of flexion, extension, lateral bending, and axial rotation of the prosthetic disc.

The bottom cap 432*a* preferably includes a generally convex retainer 437*a* formed at a center point of the bottom cap 432*a*. The retainer 437*a* is intended to cooperate with an indentation 436*b*, 436*c* formed on the upper surface of the lower core member 430*b*, 430*c* to create an engagement between the upper core member 430*a* and the lower core member 430*b*, 430*c*, as described more fully below.

The top cap 431*a* and bottom cap 432*a* preferably contain a plurality of slots 435*a* spaced radially about the surface of each of the caps. One or more fibers 440 are wound around the top cap 431*a* and bottom cap 432*a* through the slots 435*a* to attach the top and bottom caps to one another. The fibers 440 preferably are not tightly wound, thereby allowing a degree of axial rotation, bending, flexion, and extension by and between the top cap 431*a* and bottom cap 432*a*. The core center 434*a* is preferably pre-compressed. The actual number of slots 435*a* contained on each of the top cap 431*a* and bottom cap 432*a* is variable. Increasing the number of slots will result in an increase in the circumferential density of the fibers holding the endplates together. Additionally, the fibers may be wound multiple times within the same slot, thereby increasing the radial density of the fibers. In each case, this improves the wear resistance and increases the torsional and flexural stiffness of the prosthetic disc, thereby further approximating natural disc stiffness. In addition, the fibers 440 may be passed through or wound on each slot, or only on selected slots, as needed.

The purpose of the fibers 440 is to hold the top cap 431*a* and bottom cap 432*a* together and to limit the range-of-motion to mimic the range-of-motion of a natural disc. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 440 are generally elongate fibers having a diameter that ranges from about 100 µm to about 500 µm, and preferably about 200 µm to about 400 µm. Optionally, the fibers may be injection molded with an elastomer to encapsulate the fibers, thereby providing protection from tissue ingrowth and improving torsional and flexural stiffness.

The fibers 440 may be fabricated from any suitable material. Examples of suitable materials include polyester (e.g., Dacron), polyethylene, polyaramid, poly-paraphenylene terephthalamide (e.g., Kevlar) carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers 440 may be terminated on an endplate by tying a knot in the fiber on the superior surface of an endplate. Alternatively, the fibers 440 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

The sidewall 433a is preferably made of polyurethane or silicone and may be fabricated by injection molding, two-part component mixing, or dipping the core assembly into a polymer solution. Alternatively, an outer ring or gasket (not shown in the drawings) may optionally be provided in place of the sidewall 433a.

As shown, for example, in FIGS. 29 through 35, the top cap 431a of the upper core member 430a includes an edge member 438a that is adapted to engage a groove 416 formed on the perimeter of the internal surface of the upper endplate 410 to provide an engagement mechanism for attaching the upper core member 430a to the upper endplate 410. For example, the upper core member 430a is slid into the upper endplate 410, as shown by the arrows in FIG. 29. After the upper endplate 430a is fully advanced, i.e., once the leading edge of the edge member 438a contacts the interior of the groove 416 on the upper endplate 410, a tab 461a on the upper surface of the top cap 431a engages a slot 462a on the lower surface of the upper endplate 410 (see FIGS. 30 and 33), thereby locking the upper core member 430a in place within the upper endplate 410.

Turning to the first embodiment of the lower core member 430b, shown in FIGS. 29 through 32, the lower core member 430b includes a top cap 431b, a bottom cap 432b, a sidewall 433b, and a core center 434b held by and retained between the top cap 431b, bottom cap 432b, and sidewall 433b. The top cap 431b and bottom cap 432b are generally planar, and are fabricated from a physiologically acceptable material that provides substantial rigidity. Examples of materials suitable for use in fabricating the top cap 431b and bottom cap 432b include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others. The core center 434b is made of a relatively compliant material, for example, polyurethane or silicone, and is typically fabricated by injection molding. The shape of the core center 434b is typically generally cylindrical or bean-shaped, although the shape (as well as the materials making up the core center and the core member size) may be varied to obtain desired physical or performance properties. For example, the core member 434b shape, size, and materials will directly affect the degree of flexion, extension, lateral bending, and axial rotation of the prosthetic disc.

The top cap 431b preferably includes a generally concave indentation 436b formed at a center-point of the top cap 431b. The indentation 436b is intended to cooperate with the retainer 437a formed on the lower surface of the upper core member 430a to create an engagement between the upper core member 430a and the lower core member 430b, as described more fully below.

The top cap 431b and bottom cap 432b preferably contain a plurality of slots 435b spaced radially about the surface of each of the caps. One or more fibers 440 are wound around the top cap 431b and bottom cap 432b through the slots 435b to attach the top and bottom caps to one another. The fibers 440 preferably are not tightly wound, thereby allowing a degree of axial rotation, bending, flexion, and extension by and between the top cap 431b and bottom cap 432b. The core center 434b is preferably pre-compressed. The actual number of slots 435b contained on each of the top cap 431b and bottom cap 432b is variable. In addition, the fibers 440 may be passed through or wound on each slot, or only on selected slots, as needed.

The purpose of the fibers 440 is to hold the top cap 431b and bottom cap 432b together. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 440 are generally elongate fibers having a diameter that ranges from about 100 μm to about 500 μm, and preferably about 200 μm to about 400 μm.

The fibers 440 may be fabricated from any suitable material. Examples of suitable materials include polyester (e.g., Dacron), polyethylene, polyaramid, carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The sidewall 433b is preferably made of polyurethane or silicone and may be fabricated by injection molding, two-part component mixing, or dipping the core assembly into a polymer solution. Alternatively, an outer ring or gasket (not shown in the drawings) may optionally be provided in place of the sidewall 433b.

As shown, for example, in FIGS. 29 through 32, the bottom cap 432b of the lower core member 430b includes an edge member 438b that is adapted to engage a groove 426 formed on the perimeter of the internal surface of the lower endplate 420 to provide an engagement mechanism for attaching the lower core member 430b to the lower endplate 420. For example, the lower core member 430b is slid into the lower endplate 420, as shown by the arrow in FIG. 16. After the lower endplate 430b is fully advanced, i.e., once the leading edge of the edge member 438b contacts the interior of the groove 426 on the lower endplate 420, a tab 461b on the lower surface of the bottom cap 432b engages a slot 462b on the upper surface of the lower endplate 420 (see FIG. 30), thereby locking the lower core member 430b in place within the lower endplate 420.

Figure 33:
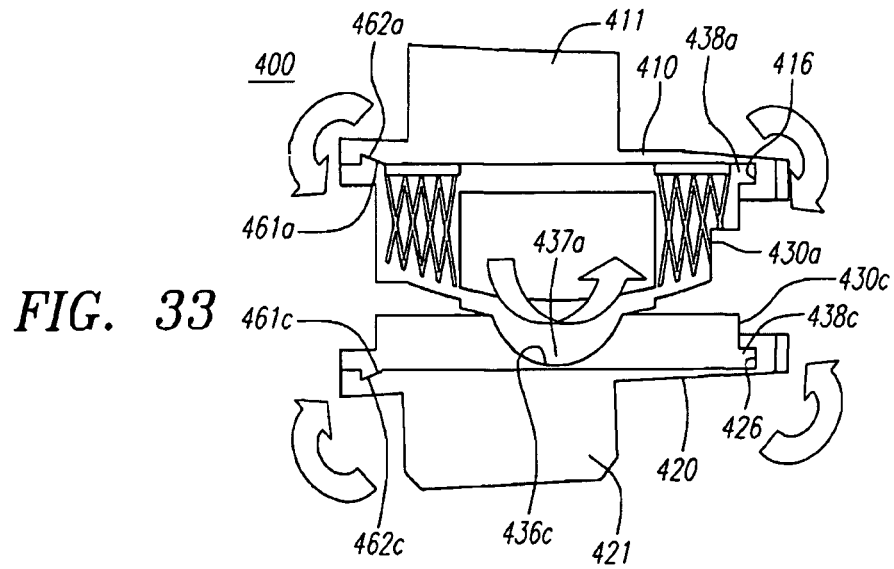
FIG. 33 provides a cross-sectional view of a prosthetic disc having a four-piece structure.
Figure 34:
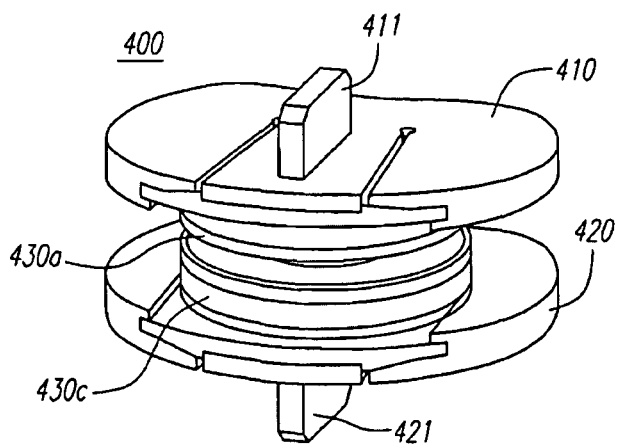
FIG. 34 provides a three-dimensional view of a prosthetic disc having a four-piece structure.
Figure 35:
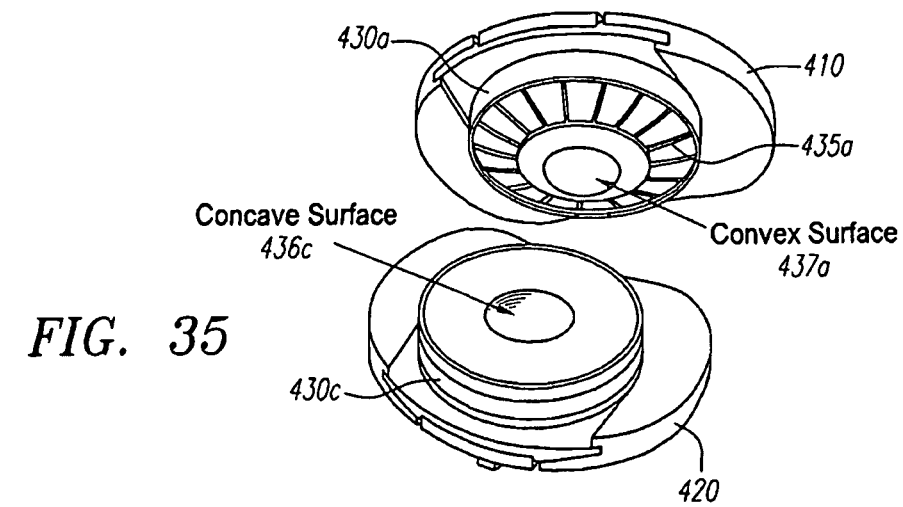
FIG. 35 provides an expanded view of a core assembly for a prosthetic disc having a four-piece structure.

Turning to the second embodiment of the lower core member 430c, shown in FIGS. 33 through 35, the lower core member 430c is formed of a solid structure having none of the top and bottom caps, sidewall, core center, or fibers that are included in the first embodiment of the lower core member 430b. The second embodiment of the lower core member 430c has an identical external shape and size to that of the first embodiment of the lower core member 430b, including having an edge member 438c that engages the groove 426 on the internal surface of the lower endplate 420. A tab 461c is configured to selectively engage the notch 462c formed on the upper internal surface of the lower endplate 420. An indentation 436c is formed on the central upper surface of the lower core member 430c, and is adapted to engage the retainer 437a formed on the upper core member 430a.

Examples of materials suitable for use in fabricating the second embodiment of the lower core member 430c include titanium, titanium alloys, stainless steel, cobalt/chromium, etc., which are manufactured by machining or metal injection molding; plastics such as polyethylene with ultra high molar mass (molecular weight) (UHMWPE), polyether ether ketone (PEEK), etc., which are manufactured by injection molding or compression molding; ceramics; graphite; and others.

The four-piece structure embodiment of the prosthetic disc is implanted by a surgical procedure. After removing the natural disc, grooves are formed in the superior and inferior vertebrae between which the prosthetic disc is to be implanted (only in the situation where the endplates are provided with anchoring fins). The upper endplate 410 and lower endplate 420 are then each implanted into the void, while aligning the anchoring fins 411, 421 with the grooves formed on the vertebral bodies. The anchoring fins cause the prosthetic disc to be secured in place between the adjacent vertebral bodies. After the upper endplate 410 and lower endplate 420 are put in position, the core assembly 430 is engaged between the endplates to complete the implantation.

The four-piece prosthetic disc has several advantages over prior art artificial discs, as well as over alternative treatment procedures such as spinal fusion. For example, the prosthetic discs described herein provide compressive compliance similar to that of a natural spinal disc. In addition, the motions in flexion, extension, lateral bending, and axial rotation are also restricted in a manner near or identical to those associated with a natural disc.

E. Fabric Tubes

The one-piece, two-piece, three-piece, and four-piece structures of the prosthetic discs described above include upper and lower endplates that are attached to each other by fibers wound around the endplates. In an alternative embodiment, the fiber component is provided in a fabric cylinder or tubing of woven or knitted form, rather than as individual fibers. The fabric tubing extends between and structurally connects the upper and lower endplates.

In a first example, a single fabric tube may be provided in place of the wound fibers. The fabric tube may be attached at its upper edge to the upper endplate, and at its lower edge to the lower endplate. For example, through-holes may be provided in each of the endplates to allow the fabric tubing (or individually woven fibers) to pass through and to be secured by knots or crimping on the external surfaces of the endplates. Alternatively, the fabric tube may be attached to each endplate by a peripheral metal or plastic ring that is fixed to the interior surfaces of the endplates.

In another example, two or more tubes of fabric may be provided between and interconnecting the upper and lower endplates. The two or more fabric tubes may be attached to the endplates by through-holes, as described above, or by press-fit, adhesion, weld, or injection molding integration to a progressively smaller metal or plastic ring with tubing circumferentially affixed to it. This structure creates an assembly of two or more concentric layers of fabric tubing. Alternatively, the concentric tubes may be terminated by collecting each tubing end together and crimping or sewing them together, then fixing the collected ends to the upper and lower endplates. As a still further alternative, an injection molded lid may be fabricated in a manner in which the lid captures the terminal ends of each of the fabric tubes during the injection molding process.

In a particularly preferred embodiment, multiple concentric fabric tubes are provided. Each of the fabric tubes may be formed from a fabric of material different from the other tubes (e.g., PET, PE, PTFE, Polyamide, etc.), or from a fabric having different material properties. This provides the ability to construct prosthetic discs having a range of performance characteristics.

As an alternative, the tubing may be comprised of a fiber reinforced elastomeric material rather than a fabric alone. For example, a polyurethane, PDMS, polyester, or other elastomer may be integrated with a fabric or with individual fibers to create a tubing that attaches and interconnects the upper and lower endplates.

F. Anti-Creep Compression Member

Figure 53:
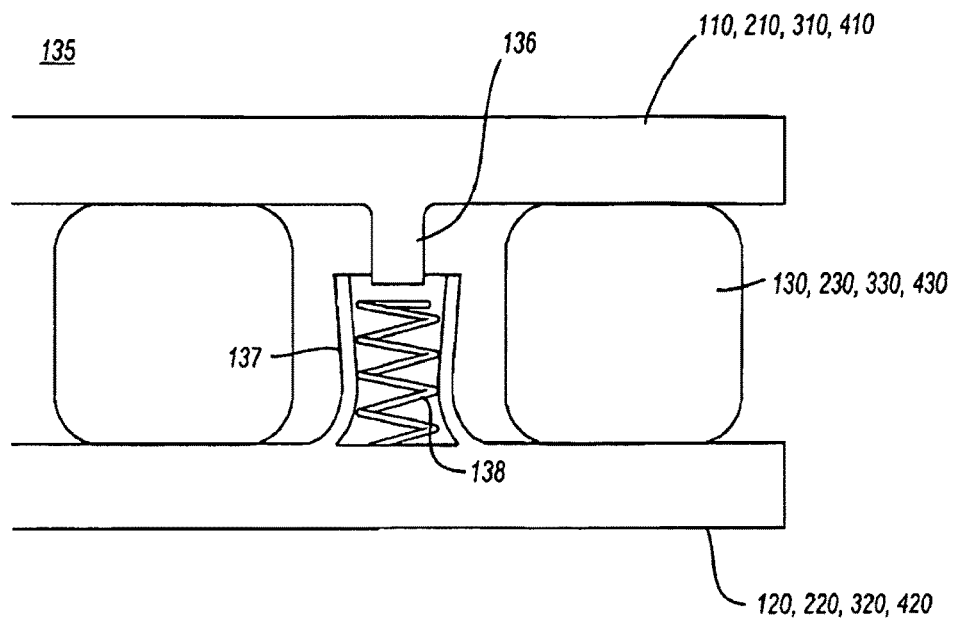
FIG. 53 provides a cross-sectional schematic illustration of an anti-creep compression member.

Turning to FIG. 53, an optional anti-creep compression member 135 is shown. The anti-creep member 135 is intended to prevent "creeping" of the core due to vertical compression and lateral expansion of the core, which occurs due to extended from wear. The anti-creep member 135 is preferably used in connection with a toroidal shaped core member 130, 230, 330, 430 of any of the one-, two-, three-, or four-piece structures of the prosthetic disc. The anti-creep element 135 includes a post 136 extending downward from the upper endplate 110, 210, 310, 410 and a mating receptacle or cup 137 extending upward from the lower endplate 120, 220, 320, 420. Alternatively, the post 136 may extend upward from the lower endplate and the receptacle 137 may extend downward from the upper endplate. A spring 138 is located within the receptacle 138. The post 136 is slightly conical in shape, and the receptacle 137 has a slightly larger diameter than the post 136 in order to receive the post 136 within the receptacle 137. The slightly conical shapes of the post 136 and cup 137 are preferred in order to accommodate lateral bending (side-to-side), flexion (forward), and extension (backward) of the upper and lower endplates relative to one another. The spring is pre-loaded to provide a force biasing the two endplates apart.

G. Advantages of the Present Prosthetic Intervertebral Discs

It is evident from the above discussion and results that the present invention provides significantly improved prosthetic intervertebral discs. Significantly, the subject discs closely imitate the mechanical properties of the fully functional natural discs that they are intended to replace.

More specifically, the modes of spinal motion may be characterized as compression, shock absorption (i.e., very rapid-compressive loading and unloading), flexion (forward) and extension (backward), lateral bending (side-to-side), torsion (twisting), and translation and subluxation (motion of axis). The prosthetic discs described herein semi-constrain each mode of motion, rather than completely constrain or allow a mode to be unconstrained. In this manner, the present prosthetic discs closely mimic the performance of natural discs. The tables below provide data that illustrates this performance.

TABLE 1

One-Piece Structure Lumbar Prosthetic Disc Compared to Natural Human Disc and Ball & Socket Design Prosthetic Disc Compressive Mode of Motion

| Properties | Human Spine | Ball & Socket Design | Prosthetic Disc Core Only | Prosthetic Disc Core & Fiber |
|---|---|---|---|---|
| Stiffness (N/mm) | ≈1288 | Very large | 800-1600 | 850-1650 |
| ROM (mm) | 0.50 | ≈0 | 0.61 | 0.50 |
| Ult. Load (N) | 3952 | >5900 | >5900 | >5900 |

TABLE 2

One-Piece Structure Cervical Prosthetic Disc Compared to
Natural Human Disc and Ball & Socket Design Prosthetic Disc
Compressive Mode of Motion

| Properties | Human Spine | Ball & Socket Design | Prosthetic Disc Core Only | Prosthetic Disc Core & Fiber |
|---|---|---|---|---|
| Stiffness (N/mm) | ≈737 | Very large | 100-950 | 150-1000 |
| ROM (mm) | 0.70 +/− 0.03 | ≈0 | ≈0.87 | ≈0.60 |
| Ult. Load (N) | ≈1600 | >5900 | >9000 | >9000 |

The subject discs exhibit stiffness in the axial direction, torsional stiffness, bending stiffness in the sagittal plane, and bending stiffness in the front plane, where the degree of these features can be controlled independently by adjusting the components of the discs. The interface mechanism between the endplates and the core members of several embodiments of the described prosthetic discs enables a very easy surgical operation. In view of the above and other benefits and features provided by the subject inventions, it is clear that the subject inventions represent a significant contribution to the art.

II. Implantation Apparatus and Methods

A. Conventional (Non-Minimally Invasive Method)

The prosthetic intervertebral discs may be implanted into a patient's spine using the apparatus and methods described herein. This description will focus on use of apparatus to implant one- and two-piece prosthetic discs, although the apparatus may also be used to implant other embodiments of the prosthetic disc with little or no modification, as will be appreciated by a person of skill in the art. In addition, and as described below, the method may incorporate less than all of the apparatus components described below.

The prosthetic discs are implanted surgically between two adjacent vertebrae, an upper vertebra and a lower vertebra, in a patient's spinal column. The vertebrae to be treated are exposed using conventional surgical procedures. After exposure, the natural vertebral disc is removed, leaving a void space between the two adjacent vertebrae. The prosthetic intervertebral disc is then implanted using the apparatus and methods described below.

1. Implantation Tools

In a first embodiment, and in reference to FIGS. 36-38, the implantation tools include a spacer 810, a two-sided chisel 830, and a holder 850.

Turning first to FIGS. 36A-B, the spacer 810 includes a proximal handle 812, a shaft 814, and a head portion 816. The handle 812 is adapted to be easily grasped by the user during the implantation procedure. The shaft 814 is preferably cylindrical and smaller in cross-section than the handle. The head portion 816 has a size and shape adapted to perform its function of being inserted between and separating two adjacent vertebral bodies. In the embodiment shown in the Figures, the head portion 816 has a generally trapezoidal shape when viewed from above or below, with a leading edge 817 being generally parallel to, but having a shorter length than the trailing edge 818. Other shapes may be used. The head portion has a thickness "h". The thickness "h" may be varied according to need, i.e., the thickness "h" will impact the ability of the user to insert the head portion 816 between the two vertebral bodies, and also the amount by which the head portion 816 will be able to separate the two bodies. Thus, a spacer 810 with a head portion 816 of relatively large or small thickness "h" may be used depending on the need. The edges 819 of the head portion 816 are generally rounded to allow the head portion 816 to be more easily inserted between the two vertebral bodies.

Figures 37A, 37B:
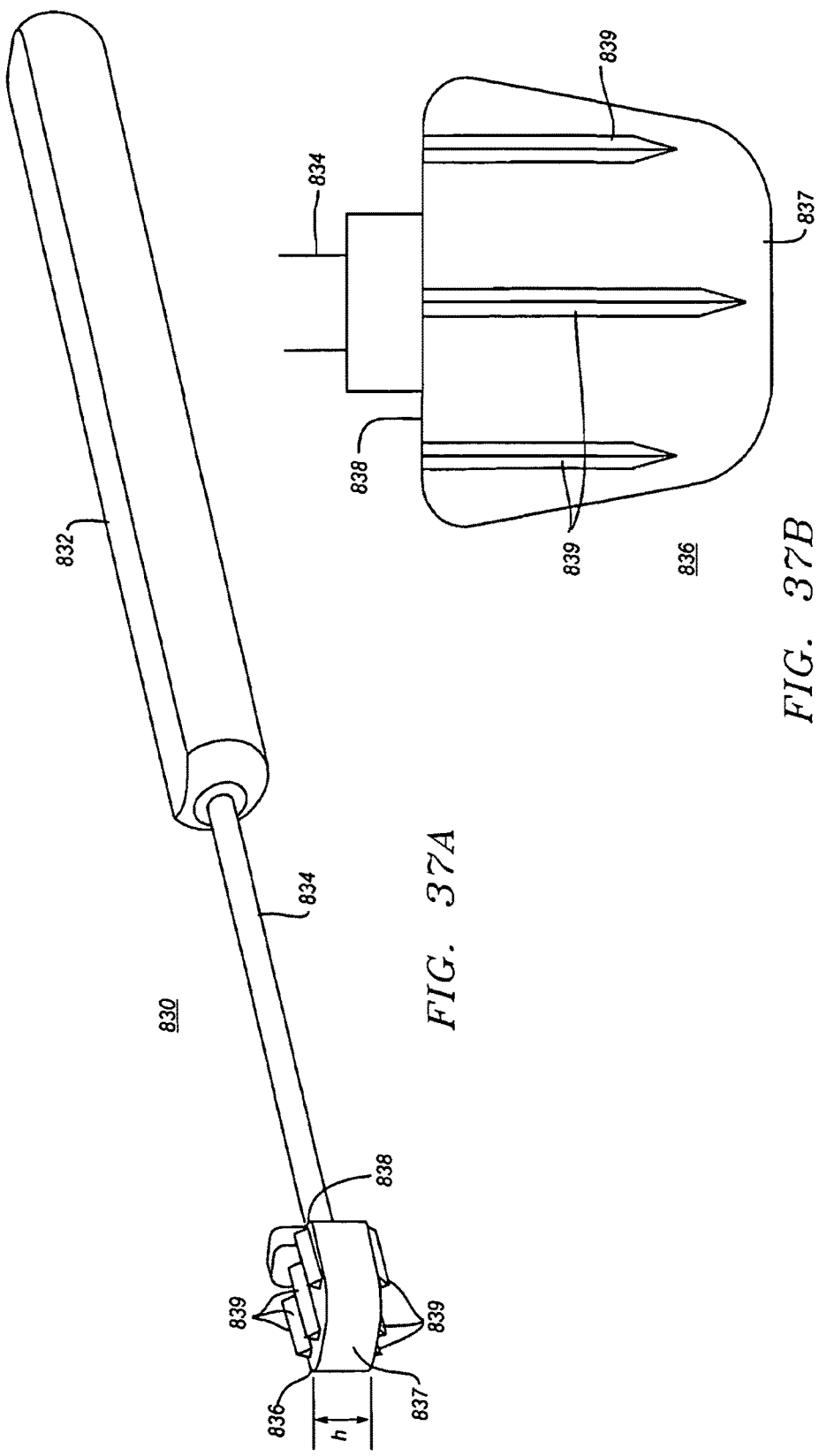
FIG. 37A provides a perspective view of a double-sided chisel.
FIG. 37B provides a top view of the head portion of the double-sided chisel shown in FIG. 37A.

Turning next to FIGS. 37A-B, the two-sided chisel 830 includes a handle 832, a shaft 834, and a head portion 836. The handle 832 is adapted to be easily grasped by the user during the implantation procedure. The shaft 834 is preferably cylindrical and smaller in cross-section than the handle. The head portion 836 has a size and shape adapted to perform its function of being inserted between and creating grooves on the two adjacent vertebral bodies. In the embodiment shown in the Figures, the head portion 836 has a generally trapezoidal shape when viewed from above or below, with a leading edge 837 being generally parallel to, but having a shorter length than the trailing edge 838. Other shapes may be used. The head portion has a thickness "h". The thickness "h" may be varied according to need, i.e., the thickness "h" will impact the ability of the user to be able to insert the head portion 836 between the two vertebral bodies and to cut grooves on the two bodies. Thus, a chisel 830 with a head portion 836 of relatively large or small thickness "h" may be used depending on the need.

The chisel 830 includes a plurality of wedge-shaped blades 839 formed on the upper and lower surfaces of the head portion 836. The blades 839 of the chisel 830 are adapted to create grooves in the lower surface of the upper vertebra and on the upper surface of the lower vertebra being treated. In the embodiment shown in the Figures, the chisel 830 includes three blades 839 on each of the upper and lower surfaces. More or fewer blades may be provided. Optimally, the number, shape, and orientation of the blades 839 on the surfaces of the chisel 830 are selected to match those of the anchoring fins provided on the surfaces of the prosthetic disc to be implanted.

Turning next to FIGS. 38A-B, the holder 850 includes a handle 852, a shaft 854, and a head portion 856. The handle 852 is adapted to be easily grasped by the user during the implantation procedure. The shaft 854 is preferably cylindrical and smaller in cross-section than the handle. The head portion 856 has a size and shape adapted to perform its function of retaining the prosthetic disc on an end thereof in order to implant the disc between the two adjacent vertebral bodies.

The head portion 856 of the holder 850 includes a proximal body portion 857 and two arms 858a-b extending distally from the body portion 857. The body portion 857 has a generally square shape, and its distal end includes a slightly concave section 859 at its center that provides a space for receiving a portion of the prosthetic disc. Each of the arms 858a-b also includes a slightly recessed portion 860a-b that is adapted to engage the side surfaces of the prosthetic disc in order to facilitate holding the disc in place during the implantation procedure. The body portion also includes engagement pins 861 on its distal surface, which engagement pins 861 are adapted to engage mating holes provided on the prosthetic disc.

In an alternative embodiment, and in reference to FIGS. 39-42, the implantation tools include a guide 500, a lower pusher 520 connected to a first chisel 540, an upper endplate holder 560, and a second chisel 580.

Figure 39:
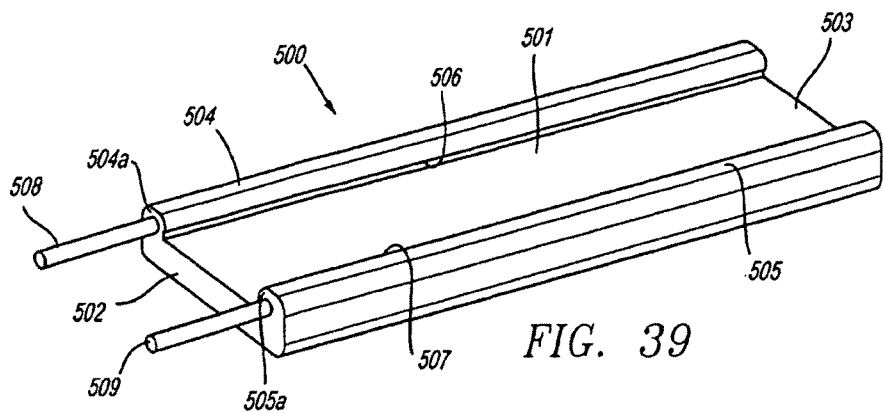
FIG. 39 provides a perspective view of a guide member.

Turning first to FIG. 39, the guide 500 serves the purposes of, first, positioning and retaining the lower endplate 220*b* in place on the lower of the two adjacent vertebrae being treated, and, second, guiding one or more of the other implantation tools to their proper locations for performing their functions. In the preferred embodiment, the guide 500 comprises a generally flat, elongated member 501 having a first end 502, a second end 503, and a pair of raised sides 504, 505. Each of the raised sides 504, 505 includes an inwardly facing portion 504*a*, 505*a* that extends back over the elongated member 501 on a plane slightly above that of the elongated member. Each of the inwardly facing portions 504*a*, 505*a* of the pair of raised sides 504, 505 thereby forms a groove 506, 507 that extends along the length of the guide 500. As described below, the grooves 506, 507 may be used to guide one or more of the other implantation tools in cooperation with a flange provided on those other tools.

Extending from the first end 502 of the guide 500 are a pair of lower endplate rods 508, 509. Each of the lower endplate rods 508, 509 is a generally cylindrical rod that extends outward from the first end 502 of the guide 500 in the plane of the elongate member 501 or parallel to that plane. The sizes of the lower endplate rods 508, 509—e.g., lengths, cylindrical diameters—are not critical, provided that the rods are of sufficient size to be capable of performing the function of engaging and retaining the lower endplate 220*b*, as described more fully below.

Figure 40:
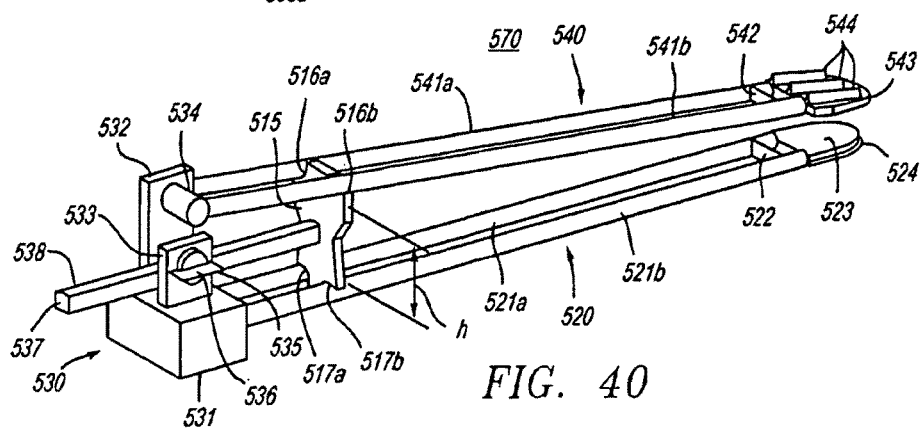
FIG. 40 provides a perspective view of a first chisel and lower endplate insert apparatus.

Turning to FIG. 40, in the preferred embodiment, a spacer tool 570 includes a combination of a lower pusher 520 and a first chisel 540 attached to a base member 530. The lower pusher 520 includes a pair of lower pusher rods 521*a*, 521*b*. Each of the lower pusher rods 521*a*, 521*b* is connected at a first end to the base 530. At a second end, a cross-member 522 extends between and connects to each of the pair of lower pusher rods 521*a*, 521*b*. The two lower pusher rods 521*a*, 521*b* are thus held in a generally parallel relation to one another and extend outward from the base 530. At the end opposite the base 530, each of the lower pusher rods 521*a*, 521*b* is attached to a lower endplate insert 523. The lower endplate insert 523 includes a flange 524 along its edge that is adapted to engage the matching slot 226 found on an outer lower endplate 220*b* of a two-piece prosthetic disc, such as those described herein.

In the preferred embodiment, each of the lower pusher rods 521*a*, 521*b* and the cross-member 522 are generally cylindrical rods. The cross-sectional shape and size of the rods are not critical, such that the lower pusher rods 521*a*, 521*b* are capable of advancing the lower endplate during the implantation procedure, as described more fully below.

In the preferred embodiment illustrated in FIG. 40, the base 530 includes a block-shaped bottom portion 531. The bottom portion 531 of the base 530 is the portion of the base to which the pusher rods 521*a*, 521*b* of the lower pusher 520 are attached. The bottom portion 531 shown in FIG. 40 has a generally block-shaped body, although the size and shape of the bottom portion 531 are not critical.

Extending upward from the top surface of the bottom portion are two flanges, a tall flange 532 and a short flange 533. A pivot pin 534 is located at the upper end of the tall flange 532. The pivot pin 534 extends through a hole in the upper end of the tall flange 532, and is able to rotate around its pivot axis. A pair of upper pusher rods 541*a*, 541*b* are attached to the pivot pin 534, with one of the two upper pusher rods 541*a* attached to a first end of the pivot pin 534, and the other upper pusher rod 541*b* attached to the opposite end of the pivot pin 534. At the end of the upper pusher rods 541*a*, 541*b* opposite the pivot pin 534, the upper pusher rods 541*a*, 541*b* are attached to a first chisel 540. In addition, a cross-member 542 attaches to and interconnects the pair of upper pusher rods 541*a*, 541*b* near the end to which the first chisel 540 is attached.

A ratchet key 535 is extends through a hole in the short flange 533. The ratchet key 535 is able to rotate around its longitudinal axis within the hole in the short flange. The ratchet key 535 includes a grasping portion 536 extending from one side of the short flange 533, and a gear portion (not shown in the Figures) extending from the opposite side of the short flange 533. An elongated guide rail 537 extends beneath the gear portion of the ratchet key 535 and generally between the pair of upper pusher rods 541*a*, 541*b* and the pair of lower pusher rods 521*a*, 521*b*. The guide rail 537 includes a plurality of teeth 538 formed on its upper side, which teeth are adapted to engage the gear portion of the ratchet key 535. Thus, by rotating the ratchet key 535, a user is able to advance or withdraw the guide rail 537.

A separator 515 is attached to an end of the guide rail 537. The separator 515 is a generally flat member that is disposed generally transversely to the guide rail 537. A pair of upper grooves 516*a*, 516*b* are formed on the top edge of the separator 515. The upper grooves 516*a*, 516*b* have a size and are located so as to slidably engage the upper pusher rods 541*a*, 541*b*. Similarly, a pair of lower grooves 517*a*, 517*b* are formed on the bottom edge of the separator 515. The lower grooves 517*a*, 517*b* have a size and are located so as to slidably engage the lower pusher rods 521*a*, 521*b*. Thus, as shown in FIG. 40, the separator is able to be advanced or withdrawn along the lengths of the upper pusher rods 541*a*, 541*b* and lower pusher rods 521*a*, 521*b* by turning the ratchet key 535. Turning the ratchet key 535 causes the gear portion of the ratchet key 535 to engage the teeth 538 on the guide rail 537. With reference to the perspective illustrated in FIG. 40, rotating the ratchet key clockwise will cause the guide rail 537 and the separator 515 to withdraw, i.e., to draw nearer to the base 530. Alternatively, rotating the ratchet key 535 counter-clockwise will cause the guide rail 537 and the separator to advance, i.e., to move away from the base 530.

As best seen in the illustration in FIG. 40, the separator 515 has a partial height, h, that is defined as the distance between the bottom edge of the upper grooves 516*a*, 516*b* and the top edge of the lower grooves 517*a*, 517*b*. The partial height h of the separator 515 is less than the distance separating the upper pusher rods 541*a*, 541*b* and lower pusher rods 521*a*, 521*b* at the point that they attach to the base 530. The partial height h of the separator is greater than the height of the prosthetic disc or, stated otherwise, the partial height h of the spacer is greater than the post-operative distance separating the two adjacent vertebrae being treated. Thus, as explained more fully below, the separator 515 has a partial height h that is suitable for expanding the distance separating the first chisel 540 and the lower endplate insert 523 as the separator 515 is advanced during the implantation procedure.

The first chisel 540 is attached to the ends of each of the upper pusher rods 541*a*, 541*b* opposite the tall flange 532. The first chisel 540 includes a generally flat plate portion 543 and one or more wedge-shaped blades 544 extending upward from the flat plate portion 543. The blades 544 of the first chisel are adapted to create grooves in the lower surface of the upper vertebra being treated. The flat plate portion 543 of the first chisel is preferably relatively thin in relation to the height of the prosthetic disc, thereby allowing the first chisel to be inserted between the two adjacent vertebrae after the natural disc has been removed.

Figure 41:
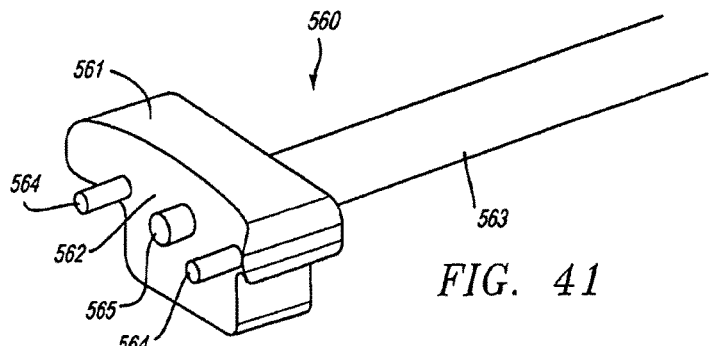
FIG. 41 provides a perspective view of an upper endplate holder.

Turning to FIG. 41, the upper endplate holder 560 includes a pusher block 561 attached to the end of a push rod 563. The pusher block 561 has a generally flat front surface 562 that is adapted to engage the trailing surface of the upper endplate of the prosthetic disc, as described more fully below. In addition, the upper endplate holder 560 includes a pair of outer engagement pins 564 extending outward from the front surface 562, and a center engagement pin 565 also extending outward from the front surface. The outer engagement pins 564 and center engagement pin 565 are each generally cylindrical in shape, and relatively short in length relative to the size of the push rod 563. The engagement pins 564, 565 are intended to engage and retain the upper endplate of the prosthetic disc during the implantation procedure, as explained more fully below.

Figure 42:
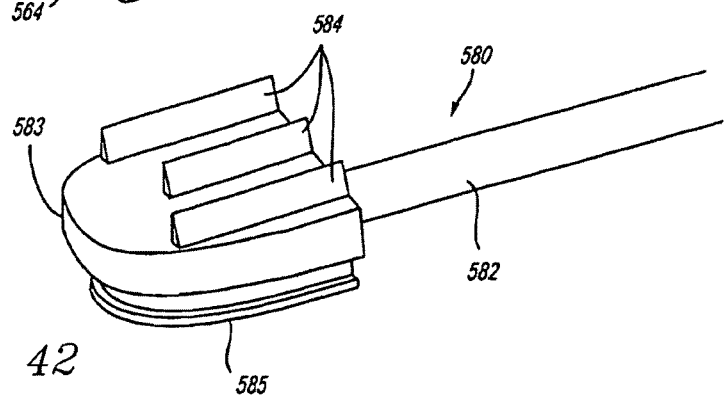
FIG. 42 provides a perspective view of a second chisel.

Turning to FIG. 42, the second chisel 580 includes a generally flat plate portion 583 attached to the end of a push rod 582. One or more wedge-shaped blades 584 attach to and extend upward from the top surface of the flat plate portion 583. Similar to the blade 544 of the first chisel 540, the blades 584 of the second chisel are adapted to create grooves in the lower surface of the upper vertebra being treated. The flat plate portion 583 of the second chisel is preferably thicker than the flat plate portion 543 of the first chisel 540, and is generally about the same thickness as the height of the prosthetic disc. A flange 585 extends outward from the bottom of the second chisel 580. The flange 585 has a size and is oriented such that it will engage the grooves 506, 507 on the guide member 500 during the implantation procedure.

2. Implantation Procedures a. First Embodiment

A preferred implantation procedure utilizes the spacer 810, chisel 830, and holder 850 shown in FIGS. 36-38. As discussed above, the procedure described herein is in relation to implantation of a one-piece prosthetic disc. This description is intended to illustrate the apparatus and methods described herein, however, and is not intended to be limiting.

A first step of the procedure is to expose the two adjacent vertebrae to be treated by conventional surgical procedures and to remove the natural disc. Once the natural disc has been removed, the spacer 810 is advanced and its head portion 816 is placed between the two adjacent vertebrae in order to separate them. After the vertebrae are adequately separated, the spacer 810 is withdrawn.

The two-sided chisel 830 is then advanced and its head portion 836 is placed between the vertebral bodies. Because of the size of the head portion 836 relative to the axial space between the vertebrae, the wedge-shaped blades 839 engage the inward-facing surfaces of the vertebrae, creating grooves on those surfaces simultaneously. After the grooves are formed as needed, the two-sided chisel is withdrawn.

A prosthetic disc is then installed on the distal end of the holder 850. Optimally, the arms 858a-b of the holder 850 engage the side surfaces of the prosthetic disc, and the proximal side of the disc butts up against the distal face of the body portion 857 of the holder 850. In this position, the holder is able to retain the prosthetic disc and hold it in place. The prosthetic disc is then advanced by the holder into the disc space between the two vertebrae. Optimally, the anchoring fins on the external surfaces of the prosthetic disc are aligned with the grooves formed in the upper and lower vertebrae as the disc is implanted. Once the disc has been satisfactorily located, the holder 850 is withdrawn, leaving the disc in place.

b. Second Embodiment

An alternative implantation procedure is illustrated in FIGS. 43 through 49. The preferred procedure utilizes the implantation tools described above in relation to FIGS. 39-42. As discussed above, the procedure described herein is in relation to implantation of a two-piece prosthetic disc. This description is intended to illustrate the apparatus and methods described herein, however, and is not intended to be limiting.

Figure 43A:
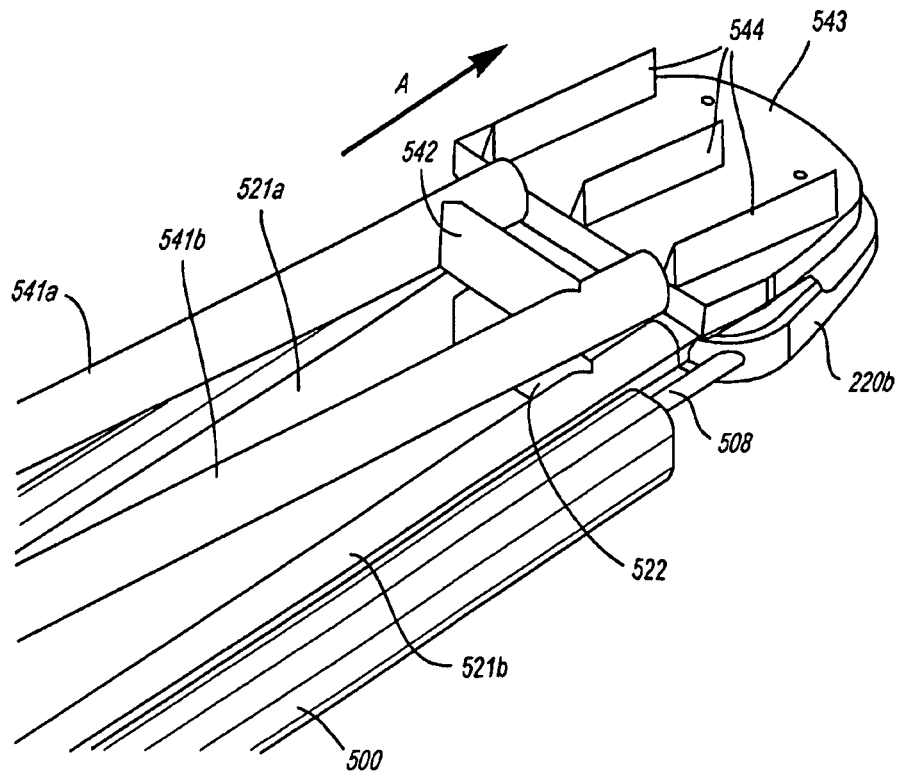
FIG. 43A provides an illustration of a method step of advancing a first chisel and outer lower endplate.
Figure 43B:
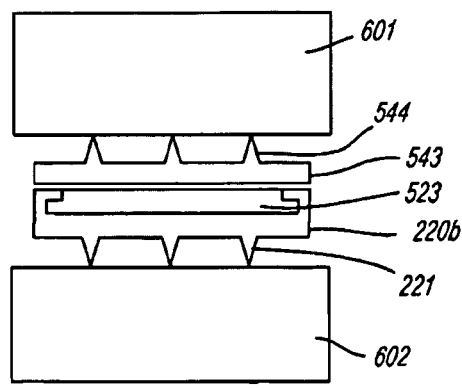
FIG. 43B provides an illustration showing a pair of adjacent vertebrae during an implantation procedure.

Turning first to FIGS. 43A-B, after the two adjacent vertebrae to be treated are exposed by conventional surgical procedures and the natural disc is removed, the guide member 500, lower pusher 520, and upper pusher rods 541a, 541b are advanced in the direction of arrow "A" toward the void space between the two adjacent vertebrae 601, 602 until the outer lower endplate 220b and first chisel 540 are located between the two adjacent vertebrae 601, 602 (see FIG. 43B).

Figure 44A:
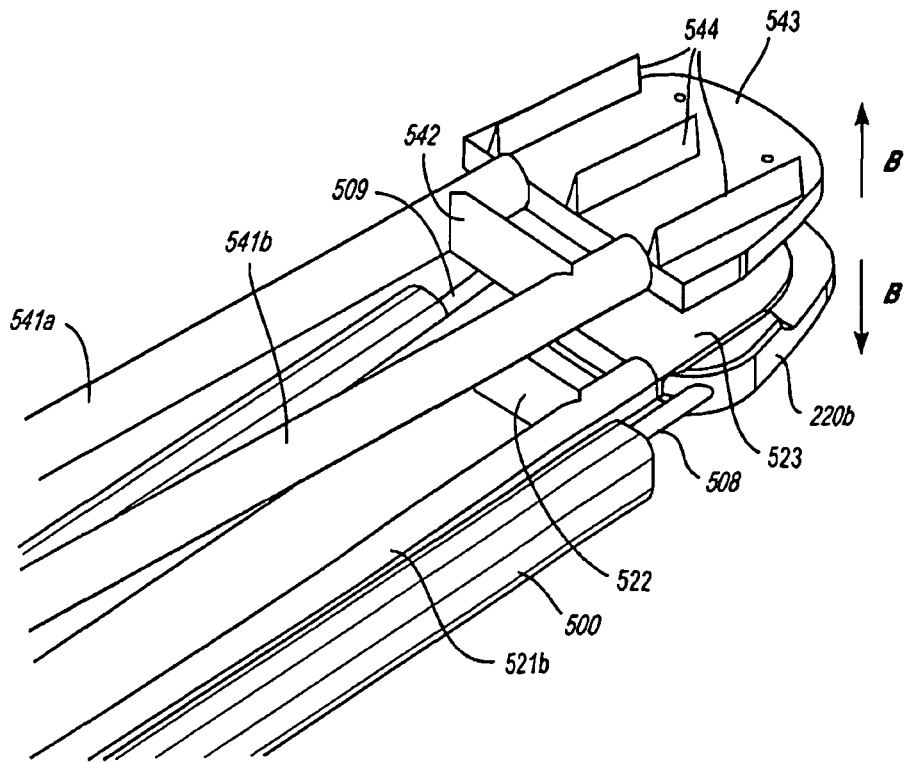
FIG. 44A provides an illustration of a method step of providing a force separating a first chisel and an outer lower endplate.
Figure 44B:
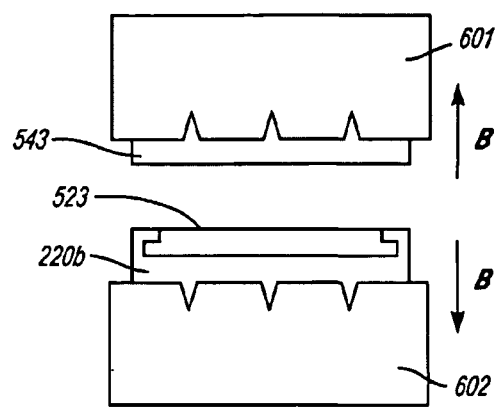
FIG. 44B provides an illustration of a pair of adjacent vertebrae during the method step shown in FIG. 44A.

At this point in the procedure, the distance "d" between the vertebrae 601, 602 is insufficient to accommodate the prosthetic disc. Accordingly, as shown in FIGS. 44A-B, a force is applied to separate the first chisel 540 and the outer lower endplate 220b, e.g., as represented by arrows "B" in FIGS. 44A-B. The separating force is applied by advancing the separator 515 away from the base member in the apparatus shown in FIG. 40 by the method described above. The upward force by the first chisel 540 causes the wedge-shaped blades 544 of the first chisel to embed in the lower surface of the upper vertebra 601, creating grooves in that surface. Similarly, the downward force by the lower endplate insert 523 and outer lower endplate 220b cause the anchor fins 221 on the lower surface of the outer lower endplate 220b to embed in the upper surface of the lower vertebra 602. Thus, by advancing the separator 515 between the upper pusher rods 541a, 541b and lower pusher rods 521a, 521b, the user is able to implant the outer lower endplate 220b onto the lower vertebra 602 and to create a set of grooves in the upper vertebra 601 that will accommodate the anchoring fins 211 on the upper endplate of the prosthetic disc.

Figure 45A:
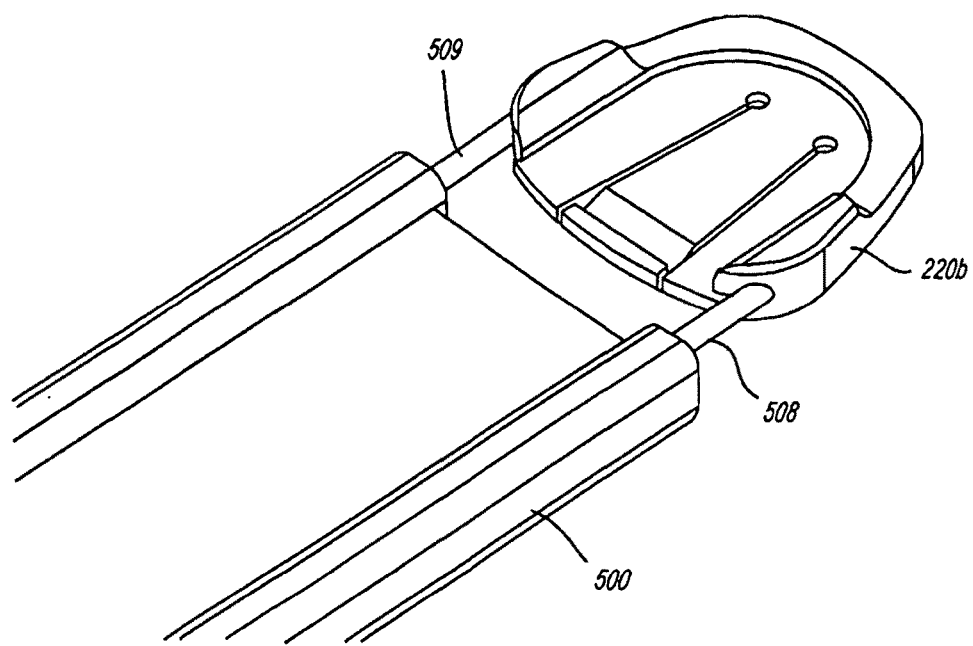
FIG. 45A provides an illustration of a guide member and outer lower endplate.
Figure 45B:
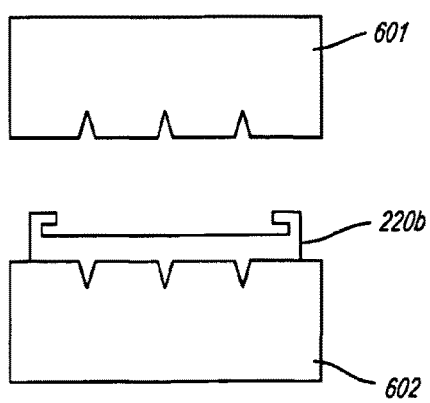
FIG. 45B provides an illustration of a pair of vertebrae with an outer lower endplate implanted onto the lower vertebra.

After the separating forces are applied as described above, the first chisel apparatus is withdrawn, as shown in FIGS. 45A-B. More particularly, the lower pusher 520 is withdrawn, thereby withdrawing the lower endplate insert 523 from the outer lower endplate 220b, leaving the outer lower endplate 220b implanted onto the lower vertebra 602. Also, the upper pusher rods 541a, 541b are withdrawn, thereby withdrawing the first chisel 540, leaving one or more grooves formed on the upper vertebra 601 (see FIG. 45B). The guide member 500 remains in place to facilitate additional procedures described below.

Figure 46A:
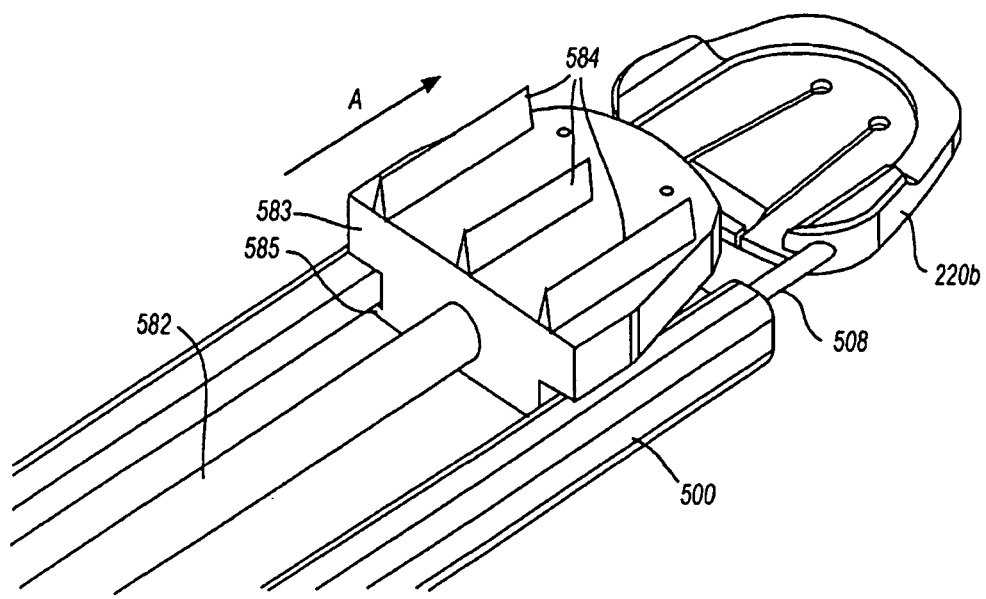
FIG. 46A provides an illustration of a method step of advancing a second chisel.
Figure 46B:
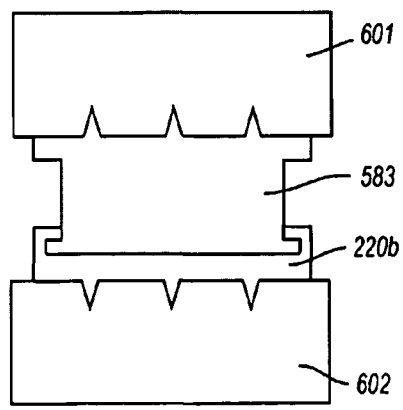
FIG. 46B provides an illustration of a pair of adjacent vertebrae during the method step shown in FIG. 46A.
Figure 47A:
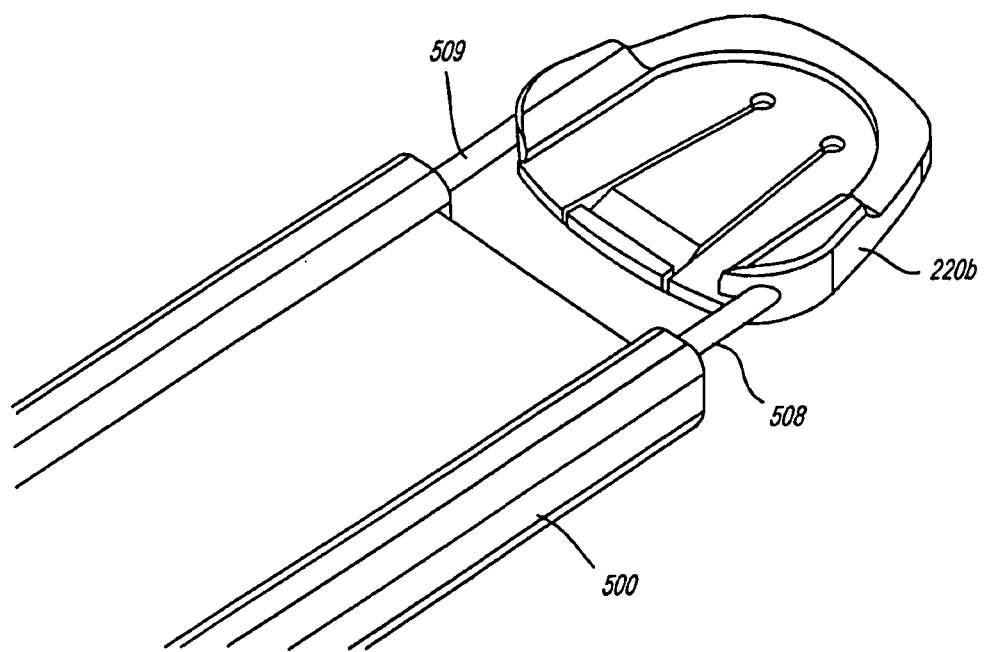
FIG. 47A provides an illustration of a guide member and outer lower endplate.
Figure 47B:
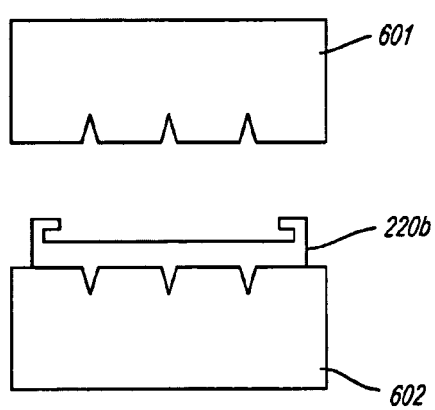
FIG. 47B provides an illustration of a pair of vertebrae with an outer lower endplate implanted onto the lower vertebra.
Figure 48A:
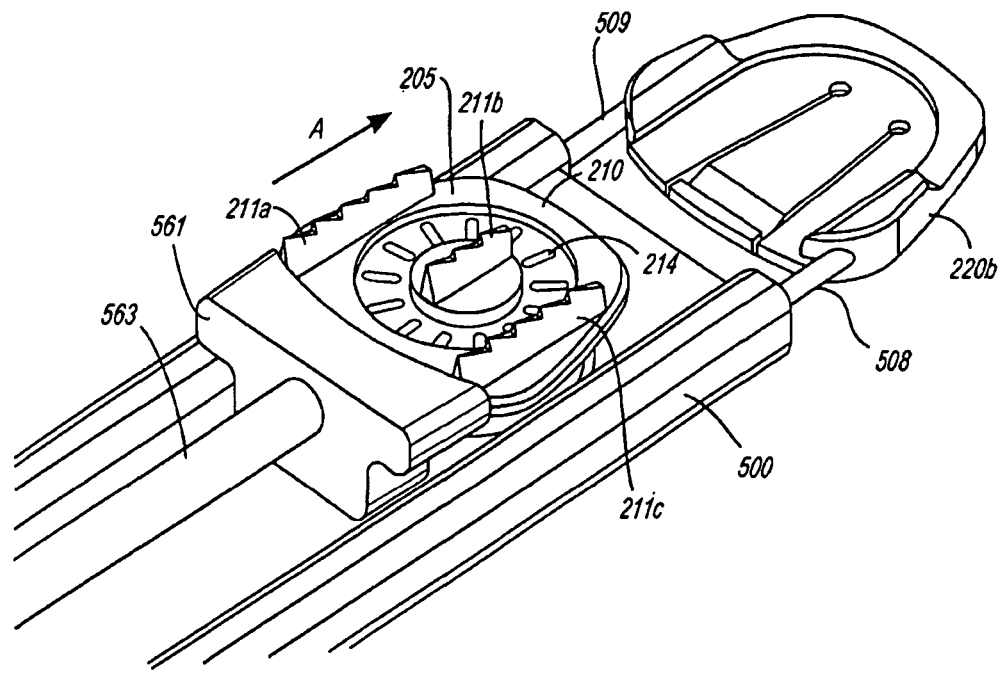
FIG. 48A provides an illustration of a method step of advancing a prosthetic disc upper subassembly.
Figure 48B:
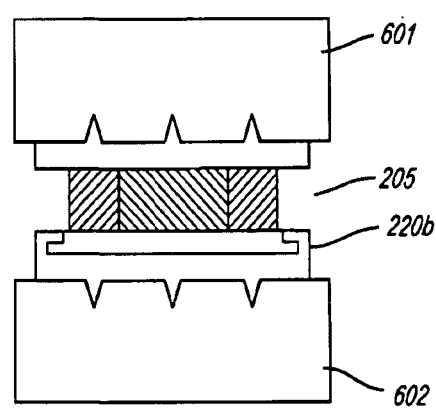
FIG. 48B provides an illustration of a pair of adjacent vertebrae during the method step shown in FIG. 48A.

After the first chisel apparatus is withdrawn, the second chisel 580 is advanced into the space between the two vertebrae 601, 602, as shown in FIGS. 46A-B. Preferably, the second chisel is advanced (see arrows "A") into the void space by advancing the push rod 583. Upon entry into the void space, the wedge-shaped blades 584 on the top surface of the second chisel engage the grooves formed in the lower surface of the upper vertebra 601 by the first chisel 540. Advantageously, the flange 585 on the bottom surface of the second chisel 580 engages and rides in the grooves 506, 507 on the guide member 500 as the second chisel is being advanced, thereby guiding the second chisel 580 into place.

As noted above, the second chisel 580 preferably has a thickness that is similar to the height of the upper endplate assembly of the two-piece prosthetic disc. Thus, advancing the second chisel 580 into the void space between the two adjacent vertebrae 601, 602 ensures that the void space is adequately prepared for implanting the remaining portion of the prosthetic disc. In addition, if the second chisel 580 has a snug fit within the void space, this will further confirm that a prosthetic disc of the appropriate size and shape is being used.

After the second chisel 580 has been advanced and engages the lower surface of the upper vertebra 601, it is withdrawn, once again leaving behind the outer lower endplate 220b implanted onto the lower vertebra 601 and the guide member 500 engaged with the outer lower endplate 220b. (See FIGS. 47A-B).

Figure 49A:
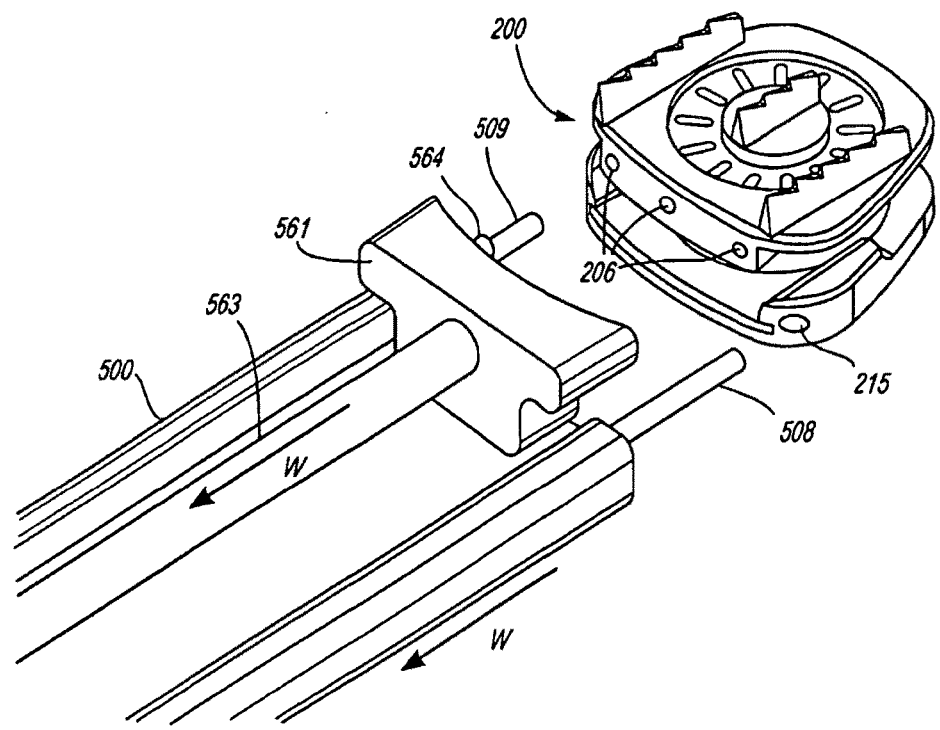
FIG. 49A provides an illustration of a method step of withdrawing an upper endplate holder and guide member.
Figure 49B:
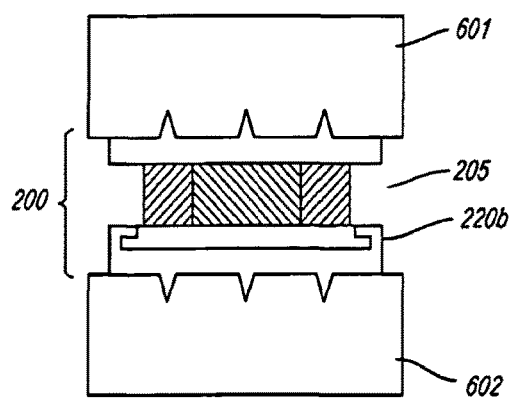
FIG. 49B provides an illustration of a pair of vertebrae with a prosthetic disc having been implanted therebetween.

Once the pair of vertebrae 601, 602 have been adequately prepared for implantation of the remaining portions of the prosthetic disc, the upper subassembly 205 of the prosthetic disc is implanted using the upper endplate holder 560. (See FIGS. 48A-B). The upper endplate holder 560 is advanced in the direction "A" by the push rod 563 until the upper subassembly 205 engages the outer lower endplate 220b and is locked in place by the tab 261 and notch (not shown). At this point, the anchoring fins 211 on the upper subassembly engage the grooves formed on the lower surface of the upper vertebra 601, thereby helping to retain the prosthetic disc in place between the two adjacent vertebrae 601, 602. Turning to FIGS. 49A-B, the upper endplate holder 560 and the guide member 500 are then withdrawn, leaving the prosthetic disc in place. FIG. 49A provides additional detail showing the manner by which the engagement pins 564, 565 of the upper endplate holder engages a set of mating holes 206 formed in the trailing edge of the upper subassembly 205. Similarly, FIG. 49A shows the manner by which the lower endplate rods 508, 509 engage the mating holes 215 formed on the trailing edge of the outer lower endplate 220b.

In an alternative method particularly adapted for implanting the one-piece structure prosthetic discs 100 described herein, implantation of the prosthetic disc is achieved without using the guide member 500, through use of only the second chisel 580, the spacer tool 570, and a modified upper endplate holder 560'. The spacer tool 570 is used, as described above, to separate the adjacent vertebral bodies to provide space for the prosthetic disc. The second chisel 580 is also used in the manner described above to provide grooves on the internal surface of the vertebral bodies to accommodate the fins on the prosthetic disc. The modified upper endplate holder 560' has a similar structure to the endplate holder 560 shown in FIG. 41, but is provided with an additional set of engagement pins 564', 565' for engaging mating holes provided on the lower endplate 120 of the one-piece prosthetic disc 100. The modified upper endplate holder 560' is used to advance the prosthetic disc 100 into place between the adjacent vertebrae, then is withdrawn.

B. Minimally Invasive Implantation

Figure 51:
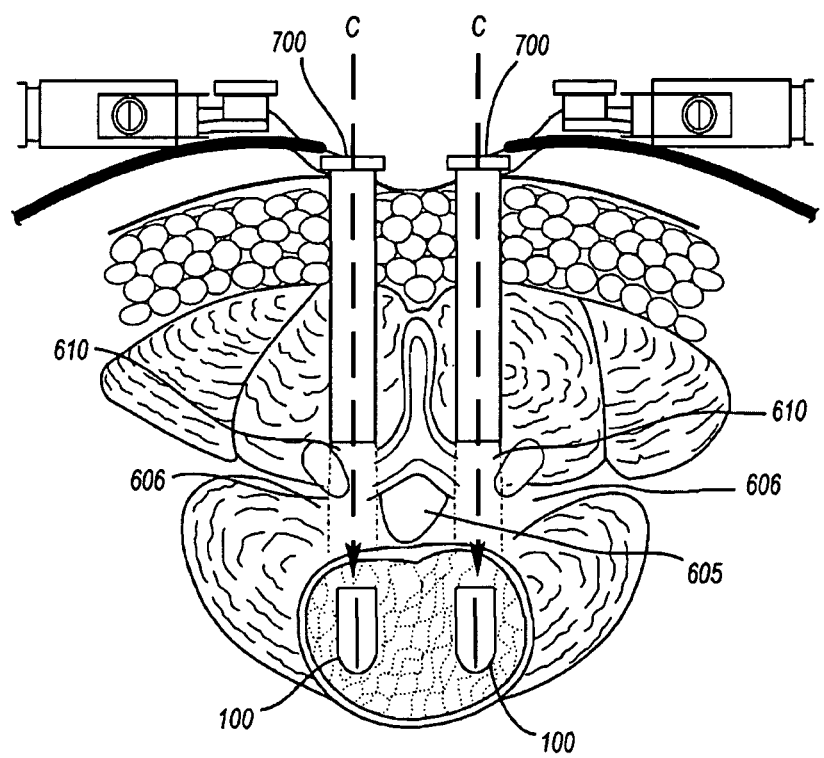
FIG. 51 provides an illustration of a minimally invasive surgical procedure for implanting a pair of prosthetic discs.

A minimally invasive surgical implantation method is illustrated in FIG. 51. The minimally invasive surgical implantation method may be performed using a posterior approach, rather than the anterior approach used for conventional lumbar disc replacement surgery.

Turning to FIG. 51, the a pair of cannulas 700 are inserted posteriorly to provide access to the spinal column. More particularly, an small incision is made and a pair of access windows are created through the lamina 610 of one of the vertebrae on each side of the vertebral canal to access the natural vertebral disc to be replaced. The spinal cord 605 and nerve roots 606 are avoided or mobilized to provide access. Once access is obtained, each of the cannulas 700 is inserted. The cannulas 700 may be used to remove the natural disc by conventional means. Alternatively, the natural disc may have already been removed by other means prior to insertion of the cannulas.

Once the natural disc has been removed and the cannulas 700 located in place, a pair of prosthetic discs are implanted between adjacent vertebral bodies. In the preferred embodiment, the prosthetic discs have a shape and size adapted for the minimally invasive procedure, such as the elongated one-piece prosthetic discs 100 described above in relation to FIGS. 50A-B. A prosthetic disc 100 is guided through each of the two cannulas 700 (see arrows "C" in FIG. 51) such that each of the prosthetic discs is implanted between the two adjacent vertebral bodies. In the preferred method, the two prosthetic discs 100 are located side by side and spaced slightly apart between the two vertebrae. Optionally, prior to implantation, grooves are created on the internal surfaces of one or both of the vertebral bodies in order to engage anchoring fins located on the prosthetic discs 100. The grooves may be created using a chisel tool adapted for use with the minimally invasive procedure.

Optionally, a third prosthetic disc may be implanted using the methods described above. The third prosthetic disc is preferably implanted at a center point, between the two prosthetic discs 100 shown in FIG. 51. The third disc would be implanted prior to the two discs shown in the Figure. Preferably, the disc would be implanted by way of either one of the cannulas, then rotated by 90.degree. to its final load bearing position between the other two prosthetic discs. The first two prosthetic discs 100 would then be implanted using the method described above.

Figure 52A:
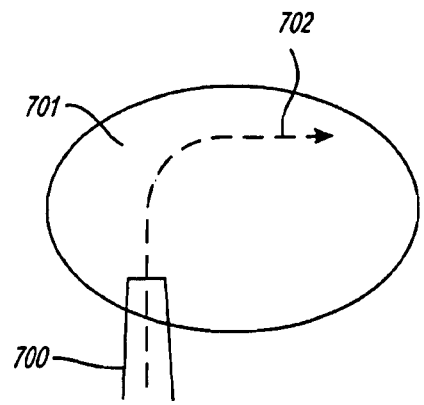
FIG. 52A provides an illustration of an alternative minimally invasive surgical procedure for implanting a prosthetic disc.
Figure 52B:
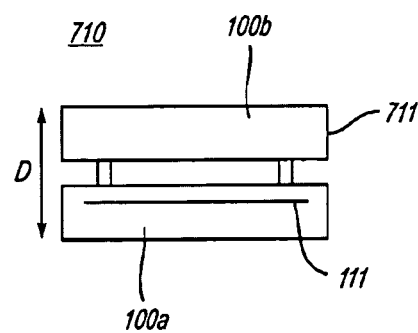
FIG. 52B provides a schematic illustration of a dual prosthetic disc having a mechanism for separating the discs after implantation.

An alternative minimally invasive implantation method and apparatus is illustrated schematically in FIGS. 52A-B. In this alternative implantation method, a single cannula 700 is used. The cannula is inserted on one side of the vertebral canal in the manner described above. Once the cannula is inserted, a chisel is used to create a groove 701 having a 90.degree. bend on the interior surfaces of the two adjacent vertebral bodies. Thus, the terminal portion of the groove 702 is perpendicular to the axis defined by the insertion cannula 700.

Turning to FIG. 52B, a dual prosthetic disc 710 structure is shown. The dual disc 710 includes a pair of one-piece structure prosthetic discs 100a-b identical in structure to those described above in relation to FIGS. 50A-B. The two prosthetic discs 100a-b of the dual disc 710 are joined by a separating mechanism 711. The separating mechanism 711 is accessed remotely by the surgeon after the dual disc 710 has been implanted into a patient's spinal column, and is adapted to drive the two prosthetic discs 100a-b apart once they are implanted. The separating mechanism 711 may be a screw device such as a worm screw, a ratcheting mechanism, a spring, or any other mechanism suitable for providing the capability of applying a separating force between the two prosthetic discs 100a-b of the dual disc 710. Preferably, an anchoring fin 111 is provided on only one of the prosthetic discs 100a. Thus, when the dual disc 710 is implanted, the anchoring fin 111 of the first prosthetic disc 100a will retain the first disc 100a in place while the ratcheting mechanism 711 causes the second disc 100b to be separated spatially from the first disc 100a, as shown by the arrow "D".

The subject devices and systems may be provided in the form of a kit for performing the methods of the present invention. The kits may include instructions for using the various devices and systems.

Part C

I. Information Concerning the Descriptions Contained Herein

It is to be understood that the inventions that are the subject of this patent application are not limited to the particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are herein described.

All patents, patent applications, and other publications mentioned herein are hereby incorporated herein by reference in their entireties. The patents, applications, and publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim as our invention:

1. A prosthetic intervertebral disc, comprising:
    an upper plate including an upper surface, a lower surface, and a peripheral edge, wherein a first plurality of slots extend between the upper surface and the lower surface of the upper plate, and wherein the entirety of each of the first plurality of slots is positioned in an interior of the upper plate a distance away from the peripheral edge of the upper plate,
    a lower plate including an upper surface, a lower surface, and a peripheral edge, wherein a second plurality of slots extend between the upper surface and the lower surface of the lower plate, and wherein the entirety of each of the second plurality of slots is positioned in an interior of the lower plate a distance away from the peripheral edge of the lower plate;
    a core member positioned between the upper and lower plates; and
    a fibrous component extending through at least one slot of the first plurality of slots in a first direction from the lower surface to the upper surface of the upper plate, through at least a second slot of the first plurality of slots in a second direction from the upper surface to the lower surface of the upper plate, and through at least one of the second plurality of slots such that the upper plate is held to the lower plate.

2. The prosthetic intervertebral disc of claim 1, wherein each of the first plurality of slots includes a length, a depth, and a width with an outer end, a tapered portion, and an inner end narrower than the outer end, and
    wherein each of the second plurality of slots includes a length, a depth, and a width.

3. The prosthetic intervertebral disc of claim 1, wherein each of the first plurality of slots includes a length, a depth, and a width that is constant along a first part of the length of each slot and varies along a second part of the length of each slot, and
    wherein each of the second plurality of slots includes a length, a depth, and a width that is constant along a first part of the length of each slot and varies along a second part of the length of each slot.

4. The prosthetic intervertebral disc of claim 1, wherein there are thirteen slots in the first plurality of slots and thirteen slots in the second plurality of slots.

5. The prosthetic intervertebral disc of claim 1, wherein there are seventeen slots in the first plurality of slots and seventeen slots in the second plurality of slots.

6. The prosthetic intervertebral disc of claim 1, wherein the fibrous component is at least one fiber.

7. The prosthetic intervertebral disc of claim 6, wherein the at least one fiber is a multifilament fiber.

8. The prosthetic intervertebral disc of claim 1, wherein the first plurality of slots each extend vertically between the upper surface and the lower surface of the upper plate, each of the first plurality of slots being enclosed horizontally by the upper plate, and
    wherein the second plurality of slots each extend vertically between the upper surface and the lower surface of the lower plate, each of the second plurality of slots being enclosed horizontally by the lower plate.

9. The prosthetic intervertebral disc of claim 1, wherein the core member is polymeric.

10. The prosthetic intervertebral disc of claim 1, wherein the core member is elastomeric.

11. The prosthetic intervertebral disc of claim 1, wherein the first plurality of slots includes every slot in the upper plate through which the fibrous component extends, and wherein the second plurality of slots includes every slot in the lower plate through which the fibrous component extends.

12. A prosthetic intervertebral disc, comprising:
    an upper plate including a first plurality of slots extending vertically between an upper surface and a lower surface of the upper plate, each of the first plurality of slots being enclosed horizontally by the upper plate;

a lower plate including a second plurality of slots extending vertically between an upper surface and a lower surface of the lower plate, each of the second plurality of slots being enclosed horizontally by the lower plate;

a core member positioned between the upper and lower plates; and a fibrous component extending through at least one slot of the first plurality of slots in the upper plate in a first direction from the lower surface to the upper surface of the upper plate, through at least a second slot of the first plurality of slots in a second direction from the upper surface to the lower surface of the upper plate, and through at least one of the second plurality of slots in the lower plate such that the upper plate is held to the lower plate.

13. The prosthetic intervertebral disc of claim 12, wherein each of the first plurality of slots includes a length, a depth, and a width that is constant along a first part of the length of each slot and varies along a second part of the length of each slot, and wherein each of the second plurality of slots includes a length, a depth, and a width that is constant along a first part of the length of each slot and varies along a second part of the length of each slot.

14. The prosthetic intervertebral disc of claim 12, wherein there are thirteen slots in the first plurality of slots and thirteen slots in the second plurality of slots.

15. The prosthetic intervertebral disc of claim 12, wherein there are seventeen slots in the first plurality of slots and seventeen slots in the second plurality of slots.

16. The prosthetic intervertebral disc of claim 12, wherein the fibrous component is at least one fiber.

17. The prosthetic intervertebral disc of claim 16, wherein the at least one fiber is a multifilament fiber.

18. The prosthetic intervertebral disc of claim 12, wherein the core member is polymeric.

19. The prosthetic intervertebral disc of claim 12, wherein the core member is elastomeric.

20. The prosthetic intervertebral disc of claim 12, wherein the first plurality of slots includes every slot in the upper plate through which the fibrous component extends, and wherein the second plurality of slots includes every slot in the lower plate through which the fibrous component extends.

21. A prosthetic intervertebral disc, comprising:

a first plate including a first plurality of slots, each of the first plurality of slots including a length, a depth, and a width that is constant along a first part of the length of each slot and varies along a second part of the length of each slot a second plate including a second plurality of slots, each of the second plurality of slots including a length, a depth, and a width that is constant along a first part of the length of each slot and varies along a second part of the length of each slot;

a core member located between the first plate and the second plate; and a fibrous component extending through at least one slot of the first plurality of slots in a first direction extending from a lower surface to an upper surface of the first plate along the depth of the at least one slot of the first plurality of slots, through at least a second slot of the first plurality of slots in a second direction extending from the upper surface to the lower surface of the first plate along the depth of the second slot of the first plurality of slots, and through at least one slot of the second plurality of slots along the depth of the at least one of the second plurality of slots, such that the first plate is held to the second plate.

22. The prosthetic intervertebral disc of claim 21, wherein the width of each of the first plurality of slots varies along a third part of the length of each slot, wherein, for each of the first plurality of slots, the first part is located between the second and third parts, and wherein the width of each of the second plurality of slots varies along a third part of the length of each slot, wherein, for each of the second plurality of slots, the first part is located between the second and third parts.

23. The prosthetic intervertebral disc of claim 21, wherein there are thirteen slots in the first plurality of slots and thirteen slots in the second plurality of slots.

24. The prosthetic intervertebral disc of claim 21, wherein the fibrous component is at least one fiber.

25. The prosthetic intervertebral disc of claim 24, wherein the at least one fiber is a multifilament fiber.

26. The prosthetic intervertebral disc of claim 21, wherein the first plate is an upper plate and the second plate is a lower plate, wherein the first plurality of slots extend between the upper surface and the lower surface of the first plate, and wherein the entirety of each of the first plurality of slots is positioned in an interior of the first plate a distance away from a peripheral edge of the first plate, and wherein the second plurality of slots extend between an upper surface and a lower surface of the second plate, and wherein the entirety of each of the second plurality of slots is positioned in an interior of the second plate a distance away from the peripheral edge of the second plate.

27. The prosthetic intervertebral disc of claim 21, wherein the first plate is an upper plate and the second plate is a lower plate, wherein the first plurality of slots extend vertically between an upper surface and a lower surface of the upper plate, each of the first plurality of slots being enclosed horizontally by the upper plate, and wherein the second plurality of slots extend vertically between an upper surface and a lower surface of the lower plate, each of the second plurality of slots being enclosed horizontally by the lower plate.

28. The prosthetic intervertebral disc of claim 21, wherein the core member is polymeric.

29. The prosthetic intervertebral disc of claim 21, wherein the first plurality of slots includes every slot in the first plate through which the fibrous component extends, and wherein the second plurality of slots includes every slot in the second plate through which the fibrous component extends.

* * * * *